(12) United States Patent
Flohr et al.

(10) Patent No.: US 9,617,271 B2
(45) Date of Patent: Apr. 11, 2017

(54) TRIAZOLO COMPOUNDS

(71) Applicant: Hoffmann-La Roche Inc., Little Falls, NJ (US)

(72) Inventors: Alexander Flohr, Loerrach (DE); Katrin Groebke Zbinden, Liestal (CH); Christian Lerner, Binningen (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/705,140

(22) Filed: May 6, 2015

(65) Prior Publication Data

US 2015/0232472 A1 Aug. 20, 2015

Related U.S. Application Data

(63) Continuation of application No. PCT/EP2013/072966, filed on Nov. 4, 2013.

(30) Foreign Application Priority Data

Nov. 7, 2012 (EP) .................................... 12191607

(51) Int. Cl.
    *C07D 487/04* (2006.01)
    *C07D 249/14* (2006.01)
    *A61K 31/5025* (2006.01)
    *A61K 31/4196* (2006.01)

(52) U.S. Cl.
    CPC ........ *C07D 487/04* (2013.01); *A61K 31/4196* (2013.01); *A61K 31/5025* (2013.01); *C07D 249/14* (2013.01)

(58) Field of Classification Search
    CPC ...................... A61K 31/519; A61K 31/4196
    USPC ........................................... 544/236; 514/248
    See application file for complete search history.

(56) References Cited

U.S. PATENT DOCUMENTS

2011/0237564 A1    9/2011   Alvarez Sanchez et al.

FOREIGN PATENT DOCUMENTS

WO    2006/017409 A2    2/2006
WO    2012/147890 A1    11/2012

OTHER PUBLICATIONS

Kehler et al., Curr Pharm Des 17(2): 137-50, 2011, PubMed Abstract provided.*
Freshney et al., Culture of Animal Cells, A Manual of Basic Technique, Alan R. Liss, Inc., 1983, New York, p. 4.*
Dermer et al., Bio/Technology, 1994, 12:320.*
ISR for PCT/EP2013/072966.

* cited by examiner

*Primary Examiner* — Venka Taraman Balasubramanian

(57) ABSTRACT

The present invention relates to compounds of formula (I) and its use for the treatment of neurological disorders.

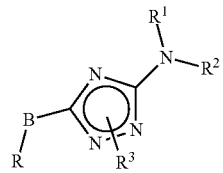

(I)

14 Claims, No Drawings

TRIAZOLO COMPOUNDS

FIELD OF INVENTION

The present invention relates to compounds of formula (I)

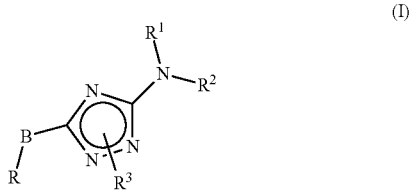

wherein

B is $C_1$-$C_4$-alkylene, $C_2$-$C_4$-alkenylene, $C_2$-$C_4$-alkynylene, $C_1$-$C_4$ alkoxy, —S—$C_1$-$C_4$ alkyl;

R is selected from the group consisting of:

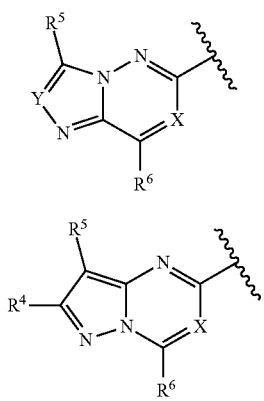

$R^1$ and $R^2$ together with the nitrogen atom to which they are attached, form a bicyclic ring system or heterocycloalkyl which can be substituted by 1 to 3 substituents independently selected from the group consisting of halogen, $C_1$-$C_7$-alkyl, $C_1$-$C_7$-hydroxyalkyl, $C_1$-$C_7$ alkoxy, $C_1$-$C_7$-haloalkyl, hydroxyl and oxo;

$R^3$ is selected from hydrogen, $C_1$-$C_7$-alkyl, $C_1$-$C_7$-alkoxyalkyl, $C_1$-$C_7$-haloalkyl, $(CH_2)_{1,2}$—$C_3$-$C_5$-cycloalkyl, —$(CH_2)_{1,2}$-aryl optionally substituted by $C_1$-$C_7$ alkoxy;

$R^4$ and $R^5$ are independently selected from hydrogen, halogen, $C_1$-$C_7$-alkyl, $C_1$-$C_7$ haloalkyl, $C_1$-$C_7$-hydroxyalkyl, cyano, or $R^4$ and $R^5$ together form a $C_3$-$C_8$ cycloalkyl $R^6$ is selected from hydrogen, $C_1$-$C_7$-alkyl, $C_1$-$C_7$-haloalkoxy, $C_3$-$C_8$ cycloalkyl, $C_1$-$C_7$ alkoxy, hydroxyl, halogen, $S(O)_2$—$C_1$-$C_7$-alkyl, —C(O)NR'R", NR'R" wherein R' and R" are independently selected from hydrogen, $C_1$-$C_7$-alkyl or R' and R" together with the nitrogen atom to which they are attached from a heterocycloalkyl or $R^6$ and $R^7$ together form a $C_3$-$C_8$ cycloalkyl, X is N or C—$R^7$ wherein $R^7$ is selected from hydrogen, $C_1$-$C_7$-alkyl, $C_1$-$C_7$ alkoxy, $C_1$-$C_7$-haloalkyl, $C_3$-$C_8$ cycloalkyl, —C(O)NR'R" wherein R' and R" are independently selected from hydrogen and $C_1$-$C_7$-alkyl, Y is N or C—$R^4$.

Further, the invention is concerned with a process for the manufacture of the above compounds, pharmaceutical preparations which contain such compounds as well as the use of these compounds for the production of pharmaceutical preparations.

SUMMARY OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 28:325-33, 2000). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 5(4): 507-518, 2001; Nakazato A and Okuyama S, et al., Exp. Opin. Ther. Patents, 10(1): 75-98, 2000). This pharmacological approach, besides ameliorating positive symptoms in schizophrenic patients, poorly addresses negative and cognitive symptoms which are the best predictors of functional outcome (Sharma T., Br. J. Psychiatry, 174 (suppl. 28): 44-51, 1999). In addition, current antipsychotic treatment is associated with adverse effects like weight gain, extrapyramidal symptoms or effects on glucose and lipid metabolism, related to their unspecific pharmacology.

In conclusion there is still a need for developing new antipsychotics with improved efficacy and safety profile. A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly, in healthy volunteers PCP-induced psychotomimetic action incorporates positive and negative symptoms as well as cognitive dysfunction, thus closely resembling schizophrenia in patients (Javitt D C et al., Biol. Psychiatry, 45: 668-679, 1999).

Cyclic nucleotides cyclic adenosine monophosphate (cAMP) and cyclic guanosine monophosphate (cGMP) are ubiquitous second messengers responsible for mediating the biological response of a variety of extracellular signals, including neurotransmitters, light and hormones. cAMP and cGMP regulate a variety of intracellular processes particularly in neurons of the central nervous system by activating cAMP- and cGMP-dependent kinases which then phosphorylate proteins involved in the regulation of synaptic transmission, neuronal differentiation and survival.

A crucial mechanism for controlling intracellular cyclic nucleotide levels and therefore cyclic nucleotide signaling is via hydrolysis of the 3',5'-phosphodiester bond by phosphodiesterases. Phosphodiesterases (PDEs) are a family of widely expressed enzymes encoded by 21 different genes in humans, with each gene encoding several splice variants (Beavo, J., Physiol. Rev. 1995, 75, 725-748; Conti, M., Jin, S. L., Prog. Nucleic Acid Res. Mol. Biol. 1999, 63, 1-38; Soderling, S. H., Beavo, J. A., Curr. Opin. Cell Biol. 2000, 12, 174-179, Manallack, D. T. et al. J. Med. Chem. 2005, 48 (10), 3449-3462).

The PDE families differ in their substrate specificity for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is a dual substrate PDE encoded by a single gene as reported in 1999 by three separate research groups (Fujishige K., et al., Eur J Biochem (1999) 266(3):1118-1127, Soderling S. H., et al., Proc Natl Acad Sci USA (1999) 96(12):7071-7076, Loughney K., et al., Gene (1999) 234 (1):109-117). PDE10A is unique from other members of the multigene family with respect to amino acid sequence (779 aa), tissue-specific pattern of expression, affinity for cAMP and cGMP and the effect on PDE activity by specific and general inhibitors.

PDE10A has one of the most restricted distribution of any PDE family being primarily expressed in the brain particularly in the nucleus accumbens and the caudate putamen. Additionally thalamus, olfactory bulb, hippocampus and frontal cortex show moderate levels of PDE10A expression. All these brain areas have been suggested to be involved in the pathophysiology of schizophrenia and psychosis, suggesting a central role of PDE10A in this devastating mental illness. Outside the central nervous system PDE10A transcript expression is also observed in peripheral tissues like thyroid gland, pituitary gland, insulin secreting pancreatic cells and testes (Fujishige, K. et al., J. Biol. Chem. 1999, 274, 18438-18445, Sweet, L. (2005) WO 2005/012485). On the other hand expression of PDE10A protein has been observed only in enteric ganglia, in testis and epididymal sperm (Coskran T. M, et al., J. Histochem. Cytochem. 2006, 54 (11), 1205-1213).

In the striatum both mRNA and protein are expressed only in the GABA (γ-aminobutyric acid)-containing medium spiny projection neurons making it an intriguing target for the treatment of diseases of the central nervous system (Fujishige, K. et al., Eur. J. Biochem. 1999, 266, 1118-1127; Seeger, T. F. et al., Brain Res. 2003, 985, 113-126). The striatal medium spiny neurons are the principal input site and first site for information integration in the basal ganglia circuit of the mammalian brain. The basal ganglia are a series of interconnected subcortical nuclei that integrate widespread cortical input with dopaminergic signaling to plan and execute relevant motor and cognitive patterns while suppressing unwanted or irrelevant patterns (Graybiel, A. M. Curr. Biol. 2000, 10, R509-R511 (2000).

Papaverine, a relatively specific PDE10A inhibitor, and PDE10A-knockout mice have been used to explore the physiology of this enzyme and the possible therapeutic utility of PDE10A inhibition. Inhibition of this enzyme pharmacologically or through gene disruption causes a reduction in activity and a reduced response to psychomotor stimulants. Inhibition also reduces the conditioned avoidance response, a behavioural response that is predictive of clinical antipsychotic activity (Siuciak, J. A.; et al., Neuropharmacology 2006, 51 (2), 386-396; Siuciak, J. A.; et al., Neuropharmacology 2006, 51 (2), 374-385).

In addition PDE10A inhibition bears the potential to improve the negative and cognitive symptoms associated to schizophrenia. Indeed papaverine have been shown to attenuate the deficits in the extra-dimensional shift learning induced in rats by sub-chronic treatment with PCP, an animal paradigm of NMDA receptor hypofunction (Rodefer, J. S., et al., Eur. J. Neuroscience 2005, 2: 1070-1076). In addition increased social interaction in PDE10A2-deficient mice have been observed (Sano, H. J. Neurochem. 2008, 105, 546-556).

Diseases that can be treated with PDE10A inhibitors include, but are not limited to, diseases thought to be mediated in part by dysfunction of the basal ganglia, of other parts of the central nervous system and of other PDE10A expressing tissues. In particular, diseases can be treated, where inhibition of PDE10A can have therapeutic effects.

These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

The compounds of the present invention are also suitable for the treatment of diabetes and related disorders such as obesity by regulating the cAMP signaling system.

PDE10A inhibitors might also be useful in preventing neurons from undergoing apoptosis by raising cAMP and cGMP levels and, thus, might possess anti-inflammatory properties. Neurodegenerative disorders treatable with PDE10A inhibitors include, but are not limited to, as Alzheimer's disease, Huntington's disease, Parkinson's disease, multiple sclerosis, stroke or spinal cord injury.

The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

DETAILED DESCRIPTION OF THE INVENTION

Definitions

Unless otherwise indicated, the following definitions are set forth to illustrate and define the meaning and scope of the various terms used to describe the invention herein.

The terms "compound(s) of the formula (I)", "compound(s) of formula (I)", "compound(s) of this invention" or "compound(s) of the present invention" refer to any compound selected from the genus of compounds as defined by the formula (I) including stereoisomers, tautomers, solvates, and salts (e.g. pharmaceutically acceptable salts) thereof.

It must be noted that, as used in the specification and the claims, the singular forms "a", "an" and "the" include plural referents unless the context clearly dictates otherwise.

When indicating the number of, the term "one or more" means from one substituent to the highest possible number of substitution, i.e. replacement of one hydrogen up to replacement of all hydrogens by substituents.

The term "optional" or "optionally" denotes that a subsequently described event or circumstance may but need not occur, and that the description includes instances where the event or circumstance occurs and instances in which it does not.

The term "substituent" denotes an atom or a group of atoms replacing a hydrogen atom on the parent molecule.

The term "alkenyl" denotes a monovalent linear or branched hydrocarbon group of 2 to 7 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl, iso-butenyl, and tert-butenyl.

The term "alkenylene" denotes a linear divalent hydrocarbon chain of 2 to 7 carbon atoms or a branched divalent hydrocarbon chain of 3 to 7 carbon atoms with at least one double bond. Exemplary alkenylene include ethenylene, 2,2-dimethylethenylene, propenylene, 2-methylpropenylene, butenylene, and pentenylene.

The term "alkoxy" denotes a group of the formula —O—R', wherein R' is an alkyl group. Examples of alkoxy moieties include methoxy, ethoxy, isopropoxy, and tert-butoxy.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term "alkylene" denotes a linear saturated divalent hydrocarbon group of 1 to 7 carbon atoms or a divalent branched saturated divalent hydrocarbon group of 3 to 7 carbon atoms. Examples of alkylene groups include methylene, ethylene, propylene, 2-methylpropylene, butylene, 2-ethylbutylene, pentylene, hexylene.

The term "alkynylene" denotes a linear divalent hydrocarbon chain of 2-6 carbon atoms or a branched divalent hydrocarbon chain of 3-6 carbon atoms with at least one triple bond. Exemplary alkynylene include ethynylene, 2,2-dimethylethynylene, propynylene, 2-methylpropynylene, butynylene, and pentynylene.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "cyanoalkyl" denotes an alkyl group wherein at least one of the hydrogen atoms of the alkyl group has been replaced by a cyano group. Examples of cyanoalkyl include cyanomethyl, cyanoethyl, cyanopropyl, cyano-isopropyl, cyano-isobutyl, cyano-sec-butyl, cyanotert-butyl, cyanopentyl or cyanohexyl.

The term "cycloalkenyl" denotes a monovalent unsaturated non-aromatic monocyclic or bicyclic hydrocarbon group of 3 to 8 ring carbon atoms. Particular cycloalkenyl groups are monocyclic. Examples of cycloalkenyl groups include cyclobuten-1-yl, and cyclopenten-1-yl.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoro-methyl. The term "perhaloalkyl" denotes an alkyl group where all hydrogen atoms of the alkyl group have been replaced by the same or different halogen atoms.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

The term "hydroxyalkyl" denotes an alkyl group wherein at least one of the hydrogen atoms of the alkyl group has been replaced by a hydroxy group. Examples of hydroxyalky include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl.

The term "alkoxyalkyl" denotes an alkyl group wherein at least one of the hydrogen atoms of the alkyl group has been replaced by an alkoxy group. Exemplary alkoxyalkyl groups include 2-methoxyethyl, 3-methoxypropyl, 1-methyl-2- methoxyethyl, 1-(2-methoxyethyl)-3-methoxypropyl, and 1-(2-methoxyethyl)-3-methoxypropyl.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "buffer" denotes a pharmaceutically acceptable excipient, which stabilizes the pH of a pharmaceutical preparation. Suitable buffers are well known in the art and can be found in the literature. Particular pharmaceutically acceptable buffers comprise histidine-buffers, arginine-buffers, citrate-buffers, succinate-buffers, acetate-buffers and phosphate-buffers. Independently from the buffer used, the pH can be adjusted with an acid or a base known in the art, e.g. hydrochloric acid, acetic acid, phosphoric acid, sulfuric acid and citric acid, sodium hydroxide and potassium hydroxide.

The present invention relates to compounds of formula I

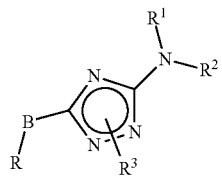
(I)

wherein
B is $C_1$-$C_4$-alkylene, $C_2$-$C_4$-alkenylene, $C_2$-$C_4$-alkynylene, $C_1$-$C_4$ alkoxy, —S—$C_1$-$C_4$ alkyl;
R is selected from the group consisting of:

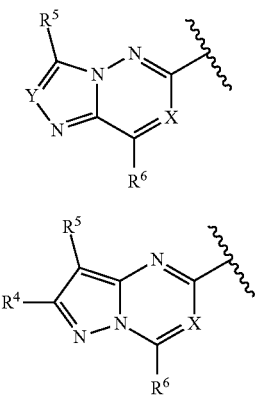

a)

b)

$R^1$ and $R^2$ together with the nitrogen atom to which they are attached, form a bicyclic ring system or heterocycloalkyl which can be substituted by 1 to 3 substituents independently selected from the group consisting of halogen, $C_1$-$C_7$-alkyl, $C_1$-$C_7$-hydroxyalkyl, $C_1$-$C_7$ alkoxy, $C_1$-$C_7$-haloalkyl, hydroxyl and oxo;

$R^3$ is selected from hydrogen, $C_1$-$C_7$-alkyl, $C_1$-$C_7$-alkoxyalkyl, $C_1$-$C_7$-haloalkyl, $(CH_2)_{1,2}$—$C_3$-$C_5$-cycloalkyl, —$(CH_2)_{1,2}$-aryl optionally substituted by $C_1$-$C_7$ alkoxy;

$R^4$ and $R^5$ are independently selected from hydrogen, halogen, $C_1$-$C_7$-alkyl, $C_1$-$C_7$ haloalkyl, $C_1$-$C_7$-hydroxyalkyl, cyano, or $R^4$ and $R^5$ together form a $C_3$-$C_8$ cycloalkyl $R^6$ is selected from hydrogen, $C_1$-$C_7$-alkyl, $C_1$-$C_7$-haloalkoxy, $C_3$-$C_8$ cycloalkyl, $C_1$-$C_7$ alkoxy, hydroxyl, halogen, $S(O)_2$—$C_1$-$C_7$-alkyl, —C(O)NR'R", NR'R" wherein R' and R" are independently selected from hydrogen, $C_1$-$C_7$-alkyl or R' and R" together with the nitrogen atom to which they are attached from a heterocycloalkyl or $R^6$ and $R^7$ together form a $C_3$-$C_8$ cycloalkyl, X is N or C—$R^7$ wherein $R^7$ is selected from hydrogen, $C_1$-$C_7$-alkyl, $C_1$-$C_7$ alkoxy, $C_1$-$C_7$-haloalkyl, $C_3$-$C_8$ cycloalkyl, —C(O)NR'R" wherein R' and R" are independently selected from hydrogen and $C_1$-$C_7$-alkyl, Y is N or C—$R^4$.

In a particular embodiment the invention relates to compounds of formula (Ig).

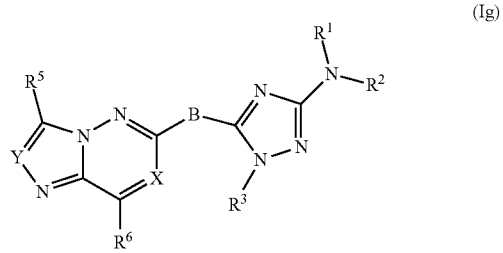
(Ig)

In a particular embodiment the invention relates to compounds of formula (Ih).

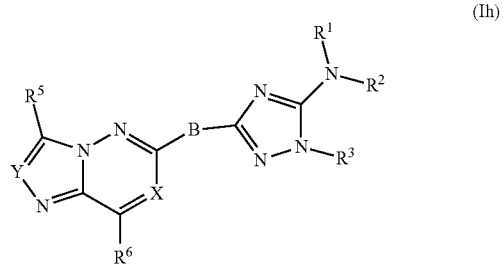
(Ih)

In a particular embodiment the invention relates to compounds of formula (I), wherein B is selected from ethylene, ethenylen, ethynylene, methoxy.

In a particular embodiment the invention relates to compounds of formula (I), wherein X is C—$R^7$ and $R^7$ is hydrogen, methyl, methoxy, cyclobutyl, cyclohexyl, C(O)NR'R" wherein R' and R" are independently selected from hydrogen and methyl.

In a particular embodiment the invention relates to compounds of formula (I), wherein X is N and $R^6$ is selected from hydroxyl, $C_1$-$C_7$ alkoxy, halogen, NR'R" wherein R' and R" are independently selected from hydrogen and $C_1$-$C_7$-alkyl.

In a particular embodiment the invention relates to compounds of formula (I), wherein $R^1$ and $R^2$ together with the nitrogen atom to which they are attached form pyrrolidinyl.

In a particular embodiment the invention relates to compounds of formula (I), wherein Y is C—$R^4$.

In a particular embodiment the invention relates to compounds of formula (I), wherein $R^3$ is selected from $C_1$-$C_7$-alkyl, preferably methyl.

In a particular embodiment the invention relates to compounds of formula (I), wherein $R^1$ and $R^2$ together with the nitrogen atom to which they are attached, form pyrrolidinyl.

In a particular embodiment the invention relates to compounds selected from the group consisting of:

3-methyl-6-(2-(1-methyl-3-(pyrrolidin-1-yl)-1H-1,2,4-triazol-5-yl)ethyl)-2-(trifluoromethyl)imidazo[1,2-b]pyridazine 2,3-dimethyl-6-(2-(1-methyl-3-(pyrrolidin-1-yl)-1H-1,2,4-triazol-5-yl)ethyl)imidazo[1,2-b]pyridazine 3-Methyl-6-[(E)-2-(2-methyl-5-pyrrolidin-1-yl-2H-[1,2,4]triazol-3-yl)-vinyl]-imidazo[1,2-b]pyridazine-2-carbonitrile 3-methyl-6-((1-methyl-5-(pyrrolidin-1-yl)-1H-1,2,4-triazol-3-yl)ethynyl)-2-(trifluoromethyl)imidazo[1,2-b]pyridazine 3-Methyl-6-[2-(2-methyl-5-pyrrolidin-1-yl-2#H!-[1,2,4]triazol-3-yl)-ethyl]-imidazo[1,2-b]pyridazine-2-carbonitrile 3-methyl-6-(2-(1-methyl-5-(pyrrolidin-1-yl)-1H-1,2,4-triazol-3-yl)ethyl)-2-(trifluoromethyl)imidazo[1,2-b]pyridazine 2-(difluoromethyl)-3-methyl-6-((1-methyl-3-(pyrrolidin-1-yl)-1H-1,2,4-triazol-5-yl)ethynyl)imidazo[1,2-b]pyridazine 2-(difluoromethyl)-3-methyl-6-(2-(1-methyl-3-(pyrrolidin-1-yl)-1H-1,2,4-triazol-5-yl)ethyl)imidazo[1,2-b]pyridazine (E)-8-methoxy-3-methyl-6-(2-(1-methyl-3-(pyrrolidin-1-yl)-1H-1,2,4-triazol-5-yl)vinyl)-2-(trifluoromethyl)imidazo[1,2-b]pyridazine 8-methoxy-3-methyl-6-(2-(1-methyl-3-(pyrrolidin-1-yl)-1H-1,2,4-triazol-5-yl)ethyl)-2-(trifluoromethyl)imidazo[1,2-b]pyridazine 6,7-dimethyl-2-(2-(1-methyl-3-(pyrrolidin-1-yl)-1H-1,2,4-triazol-5-yl)ethyl)imidazo[1,2-f][1,2,4]triazin-4-ol 8-methoxy-2,3-dimethyl-6-(2-(1-methyl-3-(pyrrolidin-1-yl)-1H-1,2,4-triazol-5-yl)ethyl)imidazo[1,2-b]pyridazine 4-methoxy-6,7-dimethyl-2-(2-(1-methyl-3-(pyrrolidin-1-yl)-1H-1,2,4-triazol-5-yl)ethyl)imidazo[1,2-f][1,2,4]triazine 5-[2-(2-Methyl-5-pyrrolidin-1-yl-2H-[1,2,4]triazol-3-yl)-ethyl]-2,3-dihydro-1H-3b,4,8-triaza-cyclopenta[a]indene 4-chloro-6,7-dimethyl-2-(2-(2-(1-methyl-3-(pyrrolidin-1-yl)-1H-1,2,4-triazol-5-yl)ethyl)imidazo[1,2-f][1,2,4]triazine 2,3,8-trimethyl-6-(2-(1-methyl-3-(pyrrolidin-1-yl)-1H-1,2,4-triazol-5-yl)ethyl)imidazo[1,2-b]pyridazine 2,3,7-trimethyl-6-((1-methyl-3-(pyrrolidin-1-yl)-1H-1,2,4-triazol-5-yl)ethynyl)imidazo[1,2-b]pyridazine 2,3,7-trimethyl-6-(2-(1-methyl-3-(pyrrolidin-1-yl)-1H-1,2,4-triazol-5-yl)ethyl)imidazo[1,2-b]pyridazine 2,3-dimethyl-6-(2-(1-methyl-3-(pyrrolidin-1-yl)-1H-1,2,4-triazol-5-yl)ethyl)-8-(pyrrolidin-1-yl)imidazo[1,2-b]pyridazine 4-chloro-6,7-dimethyl-2-(2-(2-(1-methyl-5-(pyrrolidin-1-yl)-1H-1,2,4-triazol-3-yl)ethyl)imidazo[1,2-f][1,2,4]triazine (2-methyl-6-(2-(1-methyl-3-(pyrrolidin-1-yl)-1H-1,2,4-triazol-5-yl)ethyl)imidazo[1,2-b]pyridazin-3-yl)methanol N,N,6,7-tetramethyl-2-(2-(1-methyl-3-(pyrrolidin-1-yl)-1H-1,2,4-triazol-5-yl)ethyl)imidazo[1,2-f][1,2,4]triazin-4-amine 3-methyl-6-((1-methyl-3-(pyrrolidin-1-yl)-1H-1,2,4-triazol-5-yl)methoxy)-2-(trifluoromethyl)imidazo[1,2-b]pyridazine 2,3-dimethyl-6-(2-(1-methyl-3-(pyrrolidin-1-yl)-1H-1,2,4-triazol-5-yl)ethyl)-7,8,9,10-tetrahydroimidazo[2,1-a]phthalazine 8-isopropoxy-2,3-dimethyl-6-((1-methyl-3-(pyrrolidin-1-yl)-1H-1,2,4-triazol-5-yl)ethynyl)imidazo[1,2-b]pyridazine (E)-8-isopropoxy-2,3-dimethyl-6-(2-(1-methyl-3-(pyrrolidin-1-yl)-1H-1,2,4-triazol-5-yl)vinyl)imidazo[1,2-b]pyridazine 8-isopropoxy-2,3-dimethyl-6-(2-(1-methyl-3-(pyrrolidin-1-yl)-1H-1,2,4-triazol-5-yl)ethyl)imidazo[1,2-b]pyridazine 2,3-dimethyl-6-((1-methyl-3-(pyrrolidin-1-yl)-1H-1,2,4-triazol-5-yl)methylthio)imidazo[1,2-b]pyridazine 2,3-dimethyl-6-((1-methyl-3-(pyrrolidin-1-yl)-1H-1,2,4-triazol-5-yl)ethynyl)-8-(methylsulfonyl)imidazo[1,2-b]pyridazine 2,3-dimethyl-6-((1-methyl-3-(pyrrolidin-1-yl)-1H-1,2,4-triazol-5-yl)methoxy)imidazo[1,2-b]pyridazine N-isopropyl-6,7-dimethyl-2-(2-(1-methyl-3-(pyrrolidin-1-yl)-1H-1,2,4-triazol-5-yl)ethyl)imidazo[1,2-f][1,2,4]triazin-4-amine N-ethyl-6,7-dimethyl-2-(2-(1-methyl-3-(pyrrolidin-1-yl)-1H-1,2,4-triazol-5-yl)ethyl)imidazo[1,2-f][1,2,4]triazin-4-amine 2,3-dimethyl-6-(2-(1-methyl-3-(pyrrolidin-1-yl)-1H-1,2,4-triazol-5-yl)ethyl)-8-(methylsulfonyl)imidazo[1,2-b]pyridazine N-ethyl-N,6,7-trimethyl-2-(2-(1-methyl-3-(pyrrolidin-1-yl)-1H-1,2,4-triazol-5-yl)ethyl)imidazo[1,2-f][1,2,4]triazin-4-amine N,N-diethyl-6,7-dimethyl-2-(2-(1-methyl-3-(pyrrolidin-1-yl)-1H-1,2,4-triazol-5-yl)ethyl)imidazo[1,2-f][1,2,4]triazin-4-amine 2-chloro-6-((1-methyl-3-(pyrrolidin-1-yl)-1H-1,2,4-triazol-5-yl)ethynyl)imidazo[1,2-b]pyridazine 2-chloro-6-(2-(1-methyl-3-(pyrrolidin-1-yl)-1H-1,2,4-triazol-5-yl)ethyl)imidazo[1,2-b]pyridazine 2-chloro-3-methyl-6-((1-methyl-3-(pyrrolidin-1-yl)-1H-1,2,4-triazol-5-yl)ethynyl)imidazo[1,2-b]pyridazine N,2,3-trimethyl-6-((1-methyl-3-(pyrrolidin-1-yl)-1H-1,2,4-triazol-5-yl)ethynyl)imidazo[1,2-b]pyridazine-7-carboxamide N,2,3-trimethyl-6-((1-methyl-3-(pyrrolidin-1-yl)-1H-1,2,4-triazol-5-yl)ethynyl)imidazo[1,2-b]pyridazine-8-carboxamide N,2,3-trimethyl-6-(2-(1-methyl-3-(pyrrolidin-1-yl)-1H-1,2,4-triazol-5-yl)ethyl)imidazo[1,2-b]pyridazine-8-carboxamide 2,3-dimethyl-6-((1-methyl-3-(pyrrolidin-1-yl)-1H-1,2,4-triazol-5-yl)ethynyl)-8-(trifluoromethyl)imidazo[1,2-b]pyridazine 2,3-dimethyl-6-(2-(1-methyl-3-(pyrrolidin-1-yl)-1H-1,2,4-triazol-5-yl)ethyl)-8-(trifluoromethyl)imidazo[1,2-b]pyridazine 8-isopropyl-2,3-dimethyl-6-((1-methyl-3-(pyrrolidin-1-yl)-1H-1,2,4-triazol-5-yl)ethynyl)imidazo[1,2-b]pyridazine 8-isopropyl-2,3-dimethyl-6-(2-(1-methyl-3-(pyrrolidin-1-yl)-1H-1,2,4-triazol-5-yl)ethyl)imidazo[1,2-b]pyridazine 8-cyclopropyl-2,3-dimethyl-6-((1-methyl-3-(pyrrolidin-1-yl)-1H-1,2,4-triazol-5-yl)ethynyl)imidazo[1,2-b]pyridazine 8-cyclobutyl-2,3-dimethyl-6-((1-methyl-3-(pyrrolidin-1-yl)-1H-1,2,4-triazol-5-yl)ethynyl)imidazo[1,2-b]pyridazine 8-cyclobutyl-2,3-dimethyl-6-(2-(1-methyl-3-(pyrrolidin-1-yl)-1H-1,2,4-triazol-5-yl)ethyl)imidazo[1,2-b]pyridazine
8-cyclopropyl-2,3-dimethyl-6-(2-(1-methyl-3-(pyrrolidin-1-yl)-1H-1,2,4-triazol-5-yl)ethyl)imidazo[1,2-b]pyridazine
7-isopropyl-2,3-dimethyl-6-((1-methyl-3-(pyrrolidin-1-yl)-1H-1,2,4-triazol-5-yl)ethynyl)imidazo[1,2-b]pyridazine
7-cyclobutyl-2,3-dimethyl-6-((1-methyl-3-(pyrrolidin-1-yl)-1H-1,2,4-triazol-5-yl)ethynyl)imidazo[1,2-b]pyridazine
2,3-dimethyl-5-((1-methyl-3-(pyrrolidin-1-yl)-1H-1,2,4-triazol-5-yl)ethynyl)pyrazolo[1,5-a]pyrimidine
2,3-dimethyl-5-(2-(1-methyl-3-(pyrrolidin-1-yl)-1H-1,2,4-triazol-5-yl)ethyl)pyrazolo[1,5-a]pyrimidine
3,8-dimethyl-6-((1-methyl-3-(pyrrolidin-1-yl)-1H-1,2,4-triazol-5-yl)ethynyl)-2-(trifluoromethyl)imidazo[1,2-b]pyridazine
3,8-dimethyl-6-(2-(1-methyl-3-(pyrrolidin-1-yl)-1H-1,2,4-triazol-5-yl)ethyl)-2-(trifluoromethyl)imidazo[1,2-b]pyridazine
3-methyl-6-((1-methyl-3-(pyrrolidin-1-yl)-1H-1,2,4-triazol-5-yl)ethynyl)[1,2,4]triazolo[4,3-b]pyridazine
3-methyl-6-(2-(1-methyl-3-(pyrrolidin-1-yl)-1H-1,2,4-triazol-5-yl)ethyl)[1,2,4]triazolo[4,3-b]pyridazine
7-cyclohexyl-2,3-dimethyl-6-(2-(1-methyl-3-(pyrrolidin-1-yl)-1H-1,2,4-triazol-5-yl)ethyl)imidazo[1,2-b]pyridazine
2,3,6-trimethyl-5-((1-methyl-3-(pyrrolidin-1-yl)-1H-1,2,4-triazol-5-yl)ethynyl)pyrazolo[1,5-a]pyrimidine
7-methoxy-2,3-dimethyl-6-((1-methyl-3-(pyrrolidin-1-yl)-1H-1,2,4-triazol-5-yl)ethynyl)imidazo[1,2-b]pyridazine
2,3,6-trimethyl-5-(2-(1-methyl-3-(pyrrolidin-1-yl)-1H-1,2,4-triazol-5-yl)ethyl)pyrazolo[1,5-a]pyrimidine
3-methyl-6-((1-methyl-3-(pyrrolidin-1-yl)-1H-1,2,4-triazol-5-yl)ethynyl)-8-(2,2,2-trifluoroethoxy)-2-(trifluoromethyl)imidazo[1,2-b]pyridazine
3-methyl-6-(2-(1-methyl-3-(pyrrolidin-1-yl)-1H-1,2,4-triazol-5-yl)ethyl)-8-(2,2,2-trifluoroethoxy)-2-(trifluoromethyl)imidazo[1,2-b]pyridazine
2-chloro-3-methyl-6-(2-(1-methyl-3-(pyrrolidin-1-yl)-1H-1,2,4-triazol-5-yl)ethyl)imidazo[1,2-b]pyridazine
3-chloro-2-methyl-6-((1-methyl-3-(pyrrolidin-1-yl)-1H-1,2,4-triazol-5-yl)ethynyl)imidazo[1,2-b]pyridazine
3-chloro-2-methyl-6-(2-(1-methyl-3-(pyrrolidin-1-yl)-1H-1,2,4-triazol-5-yl)ethyl)imidazo[1,2-b]pyridazine
2-methyl-6-((1-methyl-3-(pyrrolidin-1-yl)-1H-1,2,4-triazol-5-yl)ethynyl)imidazo[1,2-b]pyridazine
2-methyl-6-(2-(1-methyl-3-(pyrrolidin-1-yl)-1H-1,2,4-triazol-5-yl)ethyl)imidazo[1,2-b]pyridazine
N,3-dimethyl-6-((1-methyl-3-(pyrrolidin-1-yl)-1H-1,2,4-triazol-5-yl)ethynyl)-2-(trifluoromethyl)imidazo[1,2-b]pyridazine-8-carboxamide
N,3-dimethyl-6-(2-(1-methyl-3-(pyrrolidin-1-yl)-1H-1,2,4-triazol-5-yl)ethyl)-2-(trifluoromethyl)imidazo[1,2-b]pyridazine-8-carboxamide
3-methyl-5-[2-(2-methyl-5-pyrrolidin-1-yl-1,2,4-triazol-3-yl)ethynyl]-2-(trifluoromethyl)pyrazolo[1,5-a]pyrimidine
3-methyl-5-(2-(1-methyl-3-(pyrrolidin-1-yl)-1H-1,2,4-triazol-5-yl)ethyl)-2-(trifluoromethyl)pyrazolo[1,5-a]pyrimidine In another aspect the invention relates to the use of compounds of the invention for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

In another aspect the invention relates to the use of a compound of the invention for the preparation of a medicament for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

In another aspect the invention relates to a compound of the invention for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

In another aspect the invention relates to a method for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer, which method comprises administering an effective amount of a compound of the invention to a subject in need thereof.

In a further aspect the invention relates to a process for the manufacture of a compound of formula (I) wherein B is $C_2$-alkylen or $C_2$ alkenylen, Y is C—$R^4$ and X is C—$R^7$ comprising:

a) reacting a compound of formula (III)

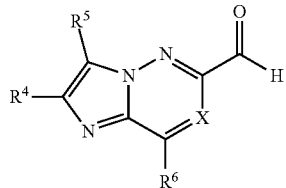
(III)

with b) a compound of formula (Ja)

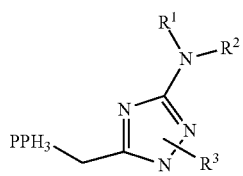
(Ja)

or c) reacting a compound of formula (F)

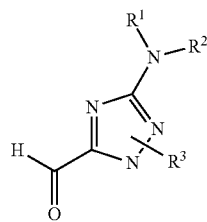
(F)

with d) a compound of formula (VI)

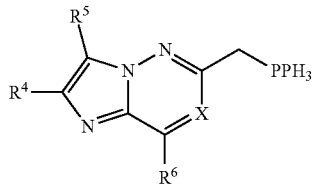
(VI)

to a compound of formula (Ij)

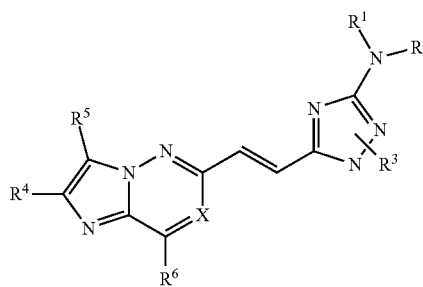
(Ij)

and optionally hydrogenation of compound of formula Ij to a compound of formula Ik

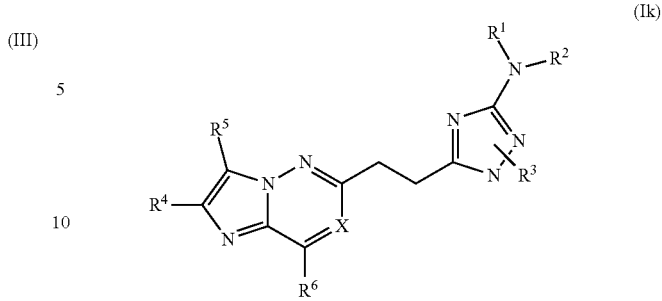
(Ik)

wherein $R^1$, $R^2$, $R^3$, $R^4$, $R^5$ and $R^6$ are as defined above.

In a further aspect the invention relates to a process for the manufacture of a compound of formula (I) wherein B is $C_2$-alkylen or $C_2$ alkynylene, Y is C—$R^4$ and X is C—$R^7$ comprising:

a) reacting a compound of formula (D)

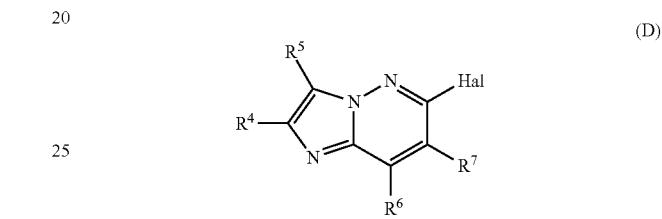
(D)

with b) a compound of formula (O) or (V)

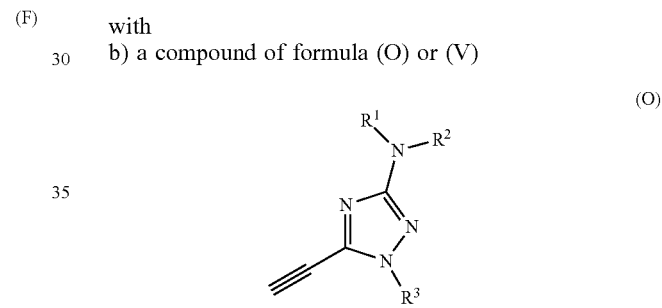
(O)

(V)

to a compound of formula (Im)

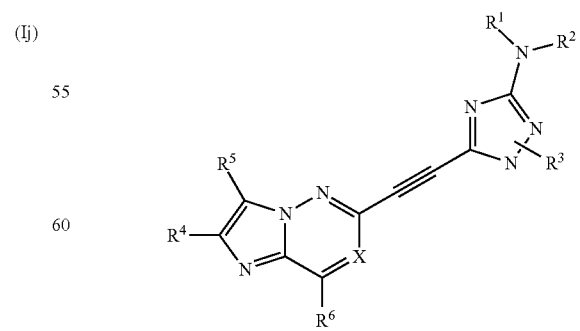

and optionally hydrogenation of compound of formula (Im) to a compound of formula (Ik)

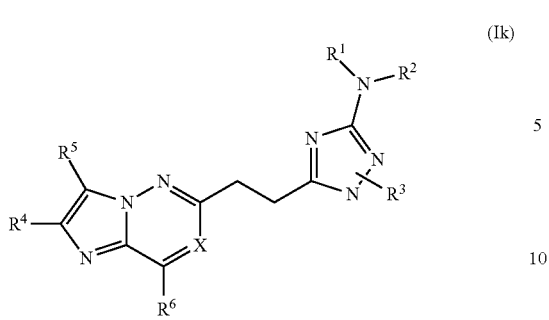
wherein $R^1$, $R^2$, $R^3$, $R^4$, $R^5$ and $R^6$ are as defined above.
General Procedures
Compounds of general formula (Ia) and (Ib) can be prepared as outlined in Scheme 1.
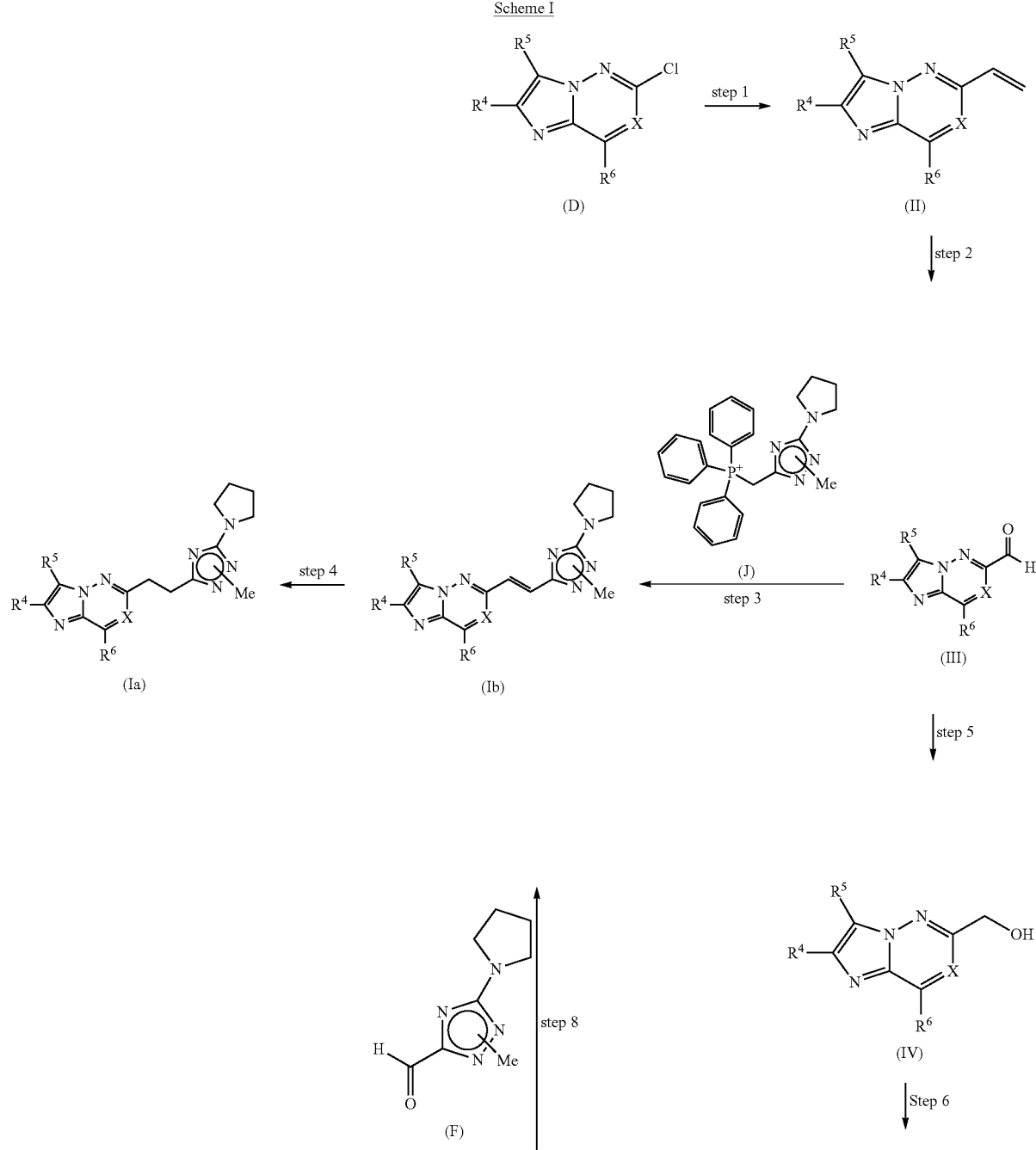

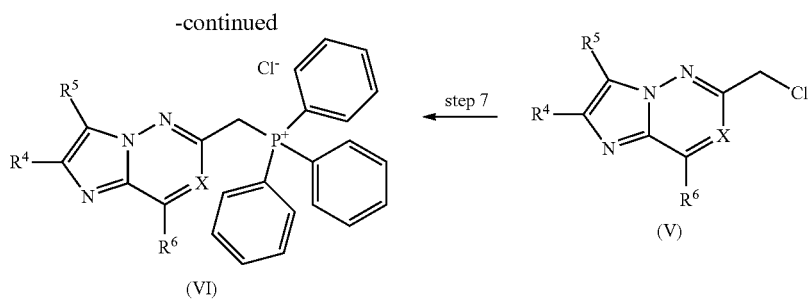

Compounds of general formula (Ib) can be prepared by Wittig reaction between aldehyde (III) and Wittig salt (L) (step 3) or alternatively between aldehyde (I) or aldehyde (N) and Wittig salt (VI) (step 8) in the presence of a suitable base such as DBU in a solvent such as THF, EtOH or mixtures thereof. Compounds of formula (Ia) are obtained by subsequent hydrogenation (step 4) at ambient pressure (balloon) using a catalyst such as Pd/C, Raney nickel or Lindlar in a solvent such as EtOH or MeOH (Scheme 1).

Compounds of formula (II), (III), (IV), (V) and (VI) can be prepared as described in the experimental part below or by literature-known methods familiar to those skilled in the art. Compounds of formula (Da) can be prepared as described in Scheme 5 and in the experimental part below as well as by literature-known methods. Building blocks (I) and (L) can be prepared as described in Scheme 6 and in the experimental part below as well as by literature-known methods.

Compounds of general formula (Ic) and (Id) can be prepared as outlined in Scheme 2.

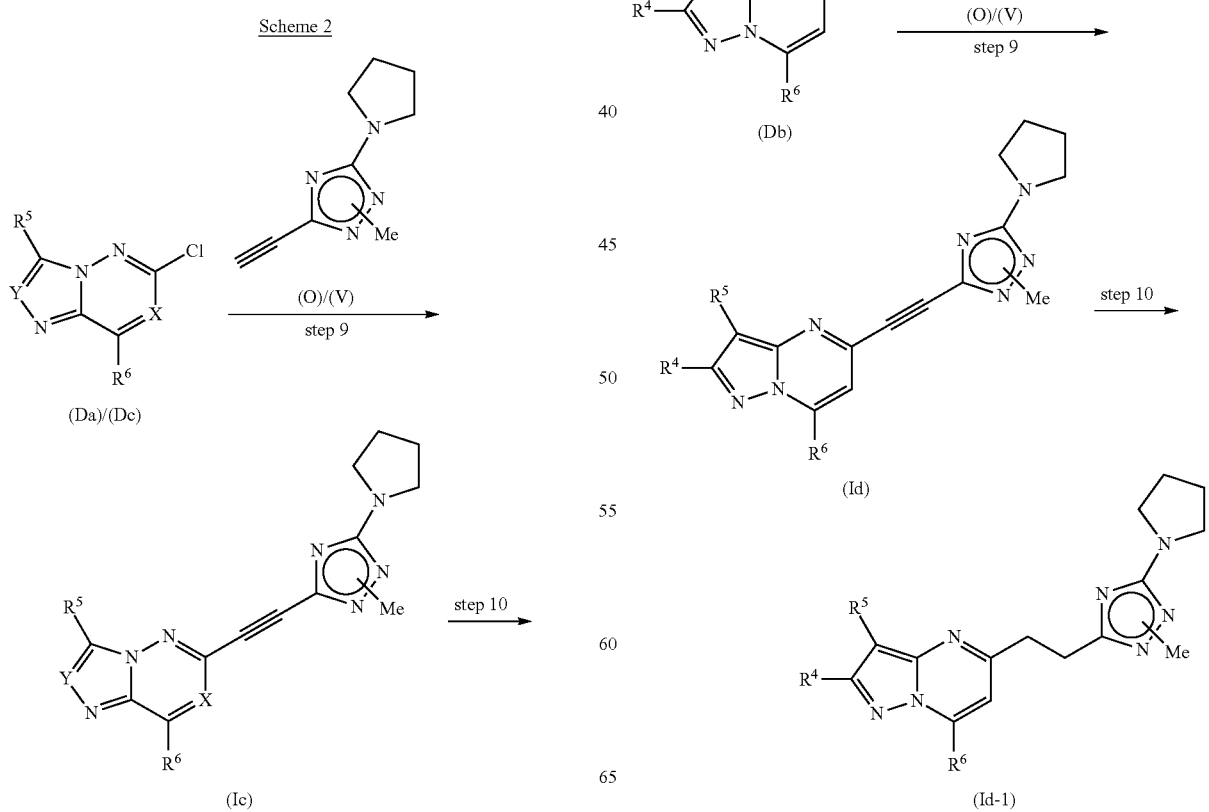

Compounds of general formula (Ic, Id) are obtained by Sonogashira reaction between an heteroaromatic halogenide (D) and alkyne (O)/(N) using a copper source such as Cu(I)I, a palladium catalyst such as bis(triphenylphosphine)palladium(II) chloride, a base such as triethylamine and a polar solvent such as DMF (steps 9). Elevated temperature and prolonged reaction time was required, especially, when chlorides were used as starting material. Compounds of formula (Ic-1)(If-1) are obtained by subsequent hydrogenation (steps 10) at ambient pressure (balloon) using a catalyst such as Pd/C or Raney nickel in a solvent such as EtOH or MeOH.

Compounds of formula (D) can be prepared as described in Scheme 5 and in the experimental part below as well as by literature-known methods.

Building block (O) can be prepared as described in Scheme 6 and in the experimental part below as well as by literature-known methods.

Compounds of general formula (Ie) can be prepared as outlined in Scheme 3.

Scheme 3

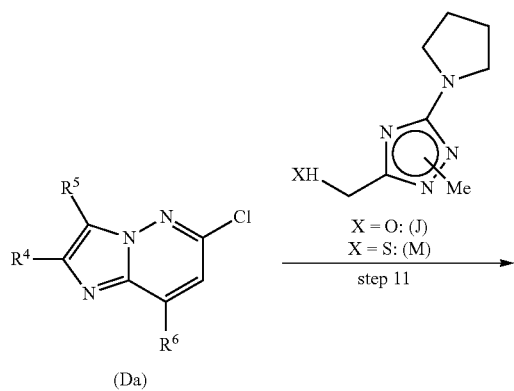

(Da)

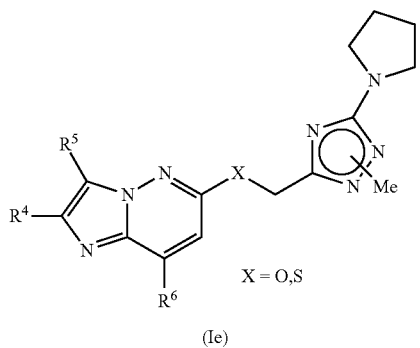

(Ie)

Compounds of general formula (Ie) are obtained by reaction heteroaromatic chloride (Da) with alcohol (J) or thiol (M) which are previously deprotonated by NaH (step 11).

Compounds of formula (D) can be prepared as described in Scheme 5 and in the experimental part below as well as by literature-known methods.

Building blocks (J) and (M) can be prepared as described in Scheme 6 and in the experimental part below as well as by literature-known methods.

Compounds of general formula (If) can be prepared as outlined in Scheme 4.

Scheme 4

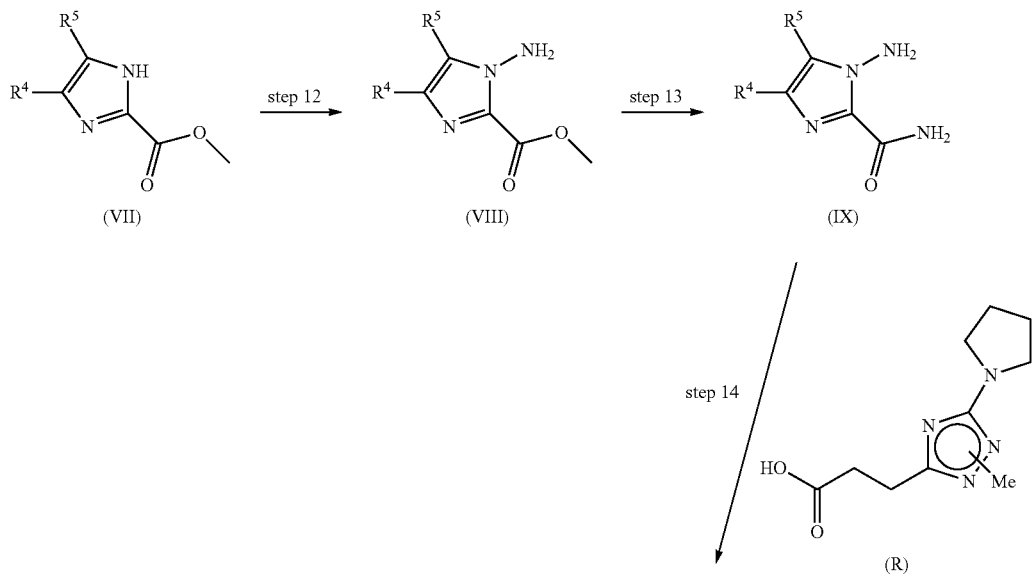

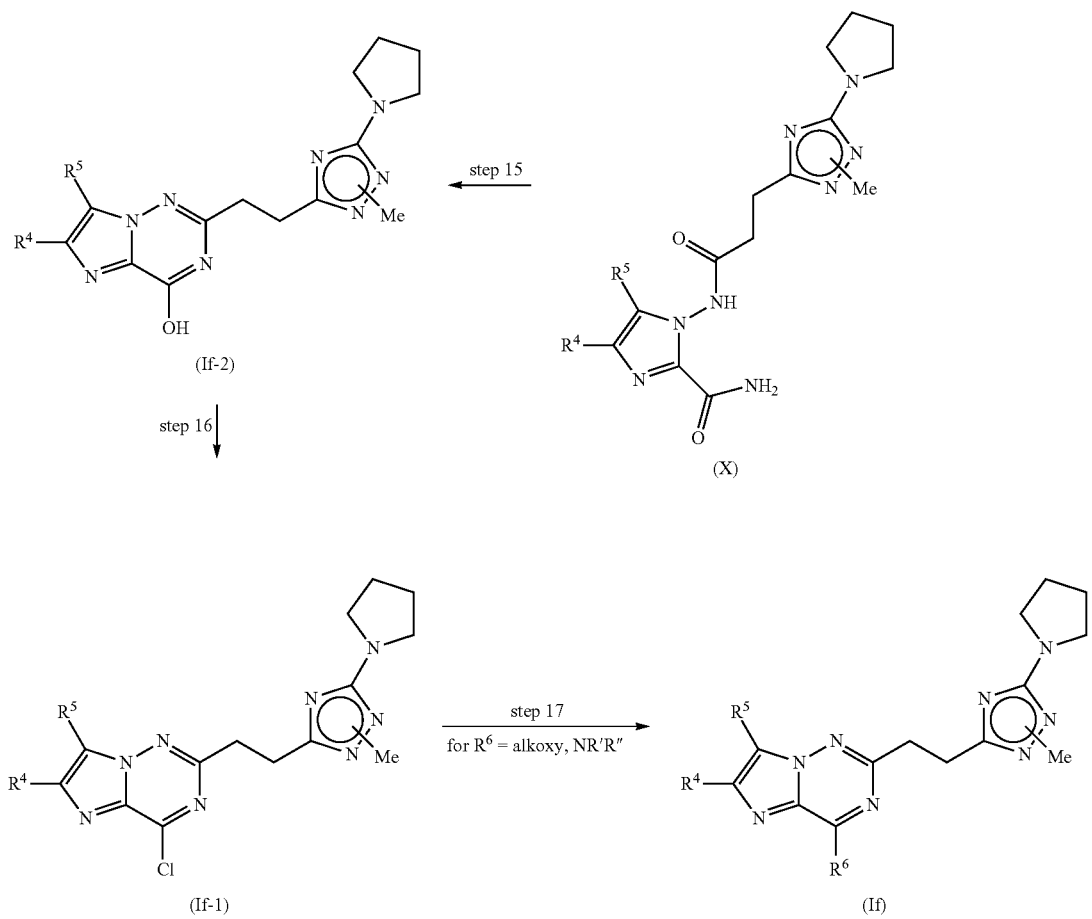

Compounds of formula (VII) are commercial or can be prepared by literature-known methods. Compounds of formula (VIII) are obtained by amination with an electrophilic ammonia reagent such as O-(diphenylphosphoryl) hydroxylamine in the presence of a base such as LiHMDS in a solvent such as DMF or THF or mixtures thereof (step 12). Compounds of formula (IX) are prepared by treatment with ammonia in MeOH at elevated temperature in an autoclave (step 13). Coupling with acid (R) in the presence of an amide coupling reagent such as 1,1'-carbonyldiimidazole in a solvent such as NMP provided compounds of formula (X) (step 14) which were then cyclized to compounds of formula (Ie-2) in the presence of a base such as $Na_2CO_3$ in a polar solvent such as EtOH, water or mixtures thereof (step 15). The corresponding chlorides (If-1) can be prepared by treatment with $POCl_3$ (step 16). Subsequent treatment with an alcoholate or an excess of an amine in a polar solvent provides compounds of formula (If) (step 17).

Intermediates of general formula (Da) can be prepared as outlined in Scheme 5.

Scheme 5

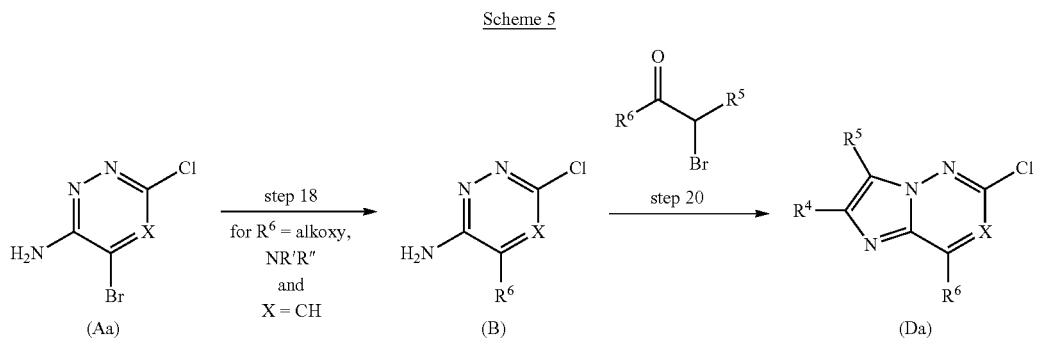

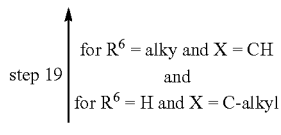

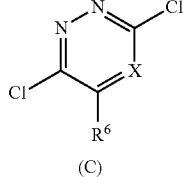

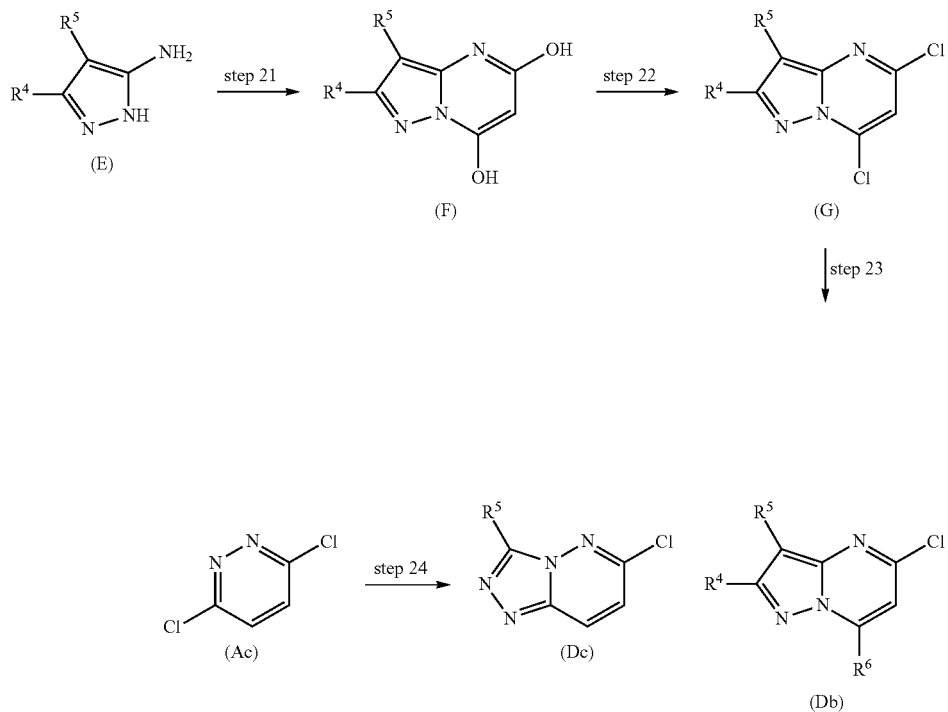

Starting material (Aa) which is commercial is treated with an alcoholate or an excess of an amine in a polar solvent to provide intermediates (B) (step 18). Intermediates of formula (B) can also be obtained by reaction starting materials of formula (C) in concentrated aqueous ammonia at elevated temperatures. Alternatively, a compound of formula (C) can be reacted with tert-butyl carbamate in the presence of a palladium catalyst such as Pd[II](OAc)$_2$, a ligand such as Xantphos, a base such as Cs$_2$CO$_3$ in a solvent such as dioxane. The Boc group can subsequently be cleaved by acid treatment, e.g. 4N HCl in dioxane. Regioisomers can in general be separated by chromatography on silica gel.

Intermediates of general formula (Da) are obtained by reaction of (B) with an cahaloketone in a polar solvent such as EtOH, dioxane or acetonitrile, optionally in the presence of a base such as NaHCO$_3$ (step 20). An intermediate of formula (Db) can be prepared according to procedures described in WO2006/128692 (step 21-23). An intermediate of general formula (Dc) can be prepared according to the procedure described in WO2011/080510 (step 24).

Further precursors and intermediates can be prepared as outlined in Scheme 6.

Scheme 6

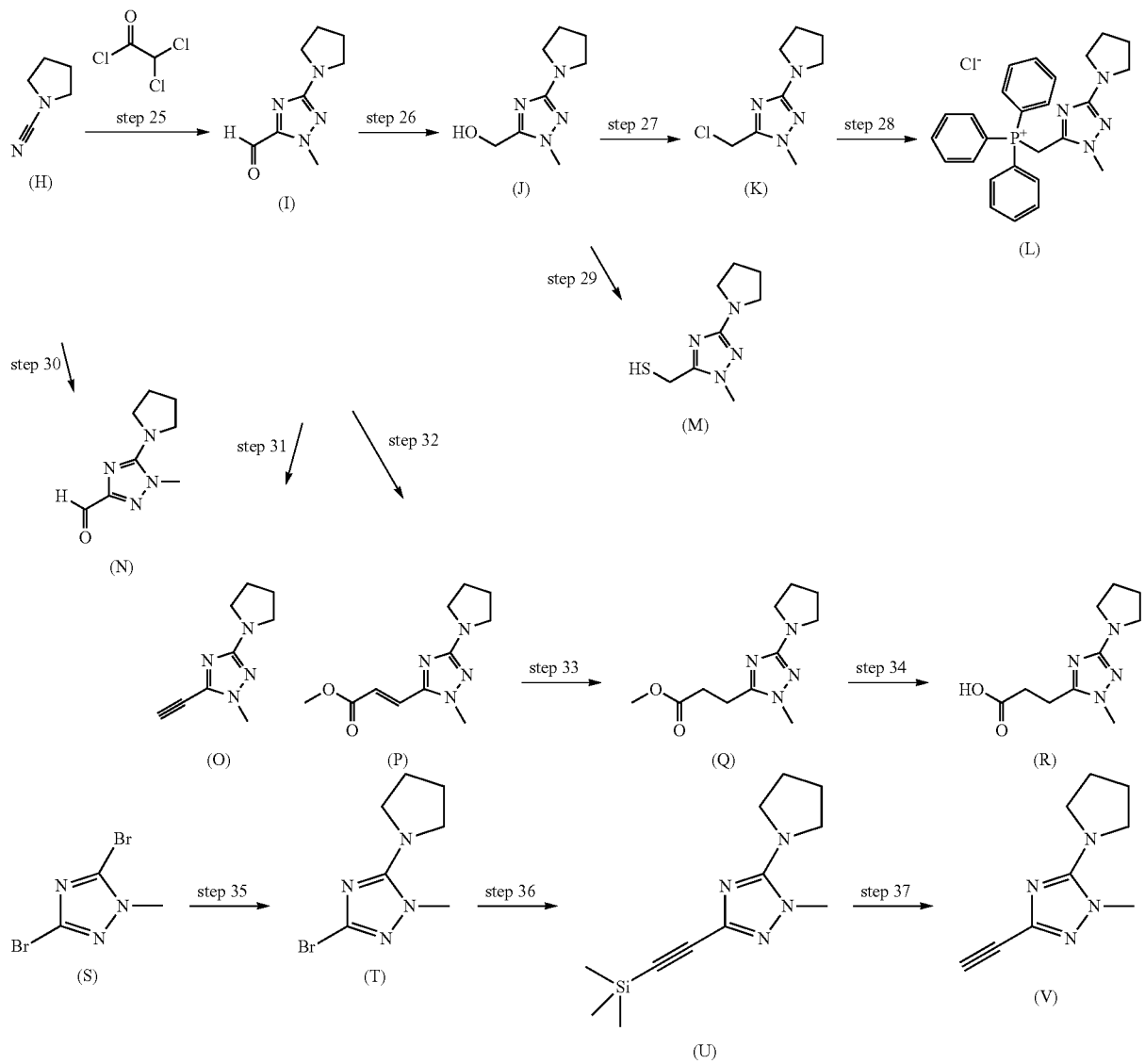

Aldehydes (I) and (N) are prepared as described in the experimental procedures described below (steps 25 and 30).

Aldehyde (I) can be converted into alcohol (J), chloromethyl derivative (K) and Wittig salt (L) as described in the experimental part below as well as by literature-methods familiar to those skilled in the art (steps 26-28). Alcohol (J) can be converted into the corresponding thiol (M) (step 29). Aldehyde (I) can also be converted to acetylene (O) using the Bestmann-Ohira reagent dimethyl 1-diazo-2-oxopropylphosphonate in the presence of a base such as $K_2CO_3$ in a solvent such as MeOH (step 31). Aldehyde (I) is additionally converted to esters (P) and (Q) and acid (R) as described in the experimental part below as well as by literature-methods (steps 32-34). The acetylene building block (V) is obtained starting from the dibromo pyrazole derivative (S) as described in the experimental part below as well as by literature-methods (steps 35-37).

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments.

In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit PDE10 and to control the cAMP signaling pathway. For example, such amount may be below the amount that is toxic to normal cells, or the mammal as a whole.

In one example, the pharmaceutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, preferably contain from about 25-100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula (I), or a stereoisomer or pharmaceutically acceptable salt thereof. In a further embodiment includes a pharmaceutical composition comprising a compound of Formula (I), or a stereoisomer or pharmaceutically acceptable salt thereof, together with a pharmaceutically acceptable carrier or excipient.

The human PDE10A full length assay was performed in 96-well micro titer plates. The reaction mixture of 50 µl contained 20 mM HEPES pH=7.5/10 mM $MgCl_2$/0.05 mg/ml BSA (Sigma cat. #A-7906), 50 nM cGMP (Sigma, cat. #G6129) and 50 nM [3H]-cGMP (GE Healthcare, cat. #TRK392 S.A. 13.2 Ci/mmol), 3.75 ng/well PDE10A enzyme (Enzo Life Science, Lausen, Switzerland cat #SE-534) with or without a specific test compound. A range of concentrations of the potential inhibitor was used to generate data for calculating the concentration of inhibitor resulting in 50% of the effect (e.g. IC50, the concentration of the competitor inhibiting PDE10A activity by 50%). Non-specific activity was tested without the enzyme. The reaction was initiated by the addition of the substrate solution (cGMP and [3H]-cGMP) and allowed to progress for 20 minutes at room temperature. The reaction was terminated by adding 25 µl of YSi-SPA scintillation beads (GE Healthcare, cat. #RPNQ0150) in 18 mM zinc sulphate solution (stop reagent). After 1 h under shaking, the plate was centrifuged one minute at 170 g to allow beads to settle. Afterwards, radioactive counts were measured on a Perkin Elmer Top-Count Scintillation plate reader.

The compounds according to formula (I) have an IC50 value below 10 µM, more specifically below 5 µM, yet more specifically below 1 µM. The following table shows data for some examples.

| Example | PDE10A inhibition IC50 [µM] |
| --- | --- |
| 1 | 0.012 |
| 2 | 0.011 |
| 3 | 0.005 |
| 4 | 0.004 |
| 5 | 0.021 |
| 6 | 0.019 |
| 7 | 0.005 |
| 8 | 0.008 |
| 9 | 0.001 |
| 10 | 0.002 |
| 11 | 0.225 |
| 12 | 0.003 |
| 13 | 0.002 |
| 14 | 0.041 |
| 15 | 0.004 |
| 16 | 0.002 |
| 17 | 0.001 |
| 18 | 0.195 |
| 19 | 0.005 |
| 20 | 0.011 |
| 21 | 0.194 |
| 22 | 0.002 |
| 23 | 0.290 |
| 24 | 0.006 |
| 25 | 0.001 |
| 26 | 0.000493 |
| 27 | 0.003 |
| 28 | 0.568 |
| 29 | 0.005 |

-continued

| Example | PDE10A inhibition IC50 [μM] |
|---|---|
| 30 | 0.098 |
| 31 | 0.003 |
| 32 | 0.006 |
| 33 | 0.041 |
| 34 | 0.005 |
| 35 | 0.00141 |
| 36 | 0.056 |
| 37 | 0.338 |
| 38 | 0.00133 |
| 39 | 1.400 |
| 40 | 0.001 |
| 41 | 0.002 |
| 42 | 0.011 |
| 43 | 0.165 |
| 44 | 0.001 |
| 45 | 0.009 |
| 46 | 0.001 |
| 47 | 0.0009 |
| 48 | 0.0023 |
| 49 | 0.0029 |
| 50 | 0.0026 |
| 51 | 0.0006 |
| 52 | 0.0026 |
| 53 | 0.0021 |
| 54 | 0.0016 |
| 55 | 0.0168 |
| 56 | 0.0382 |
| 57 | 0.5337 |
| 58 | 0.0198 |
| 59 | 0.0066 |
| 60 | 0.0027 |
| 61 | 0.076 |
| 62 | 0.003 |
| 63 | 0.0094 |
| 64 | 0.0055 |
| 65 | 0.0025 |
| 66 | 0.0145 |
| 67 | 0.0102 |
| 68 | 0.1462 |
| 69 | 0.0021 |
| 70 | 0.0137 |
| 71 | 0.0087 |
| 72 | 0.0329 |

EXAMPLES

Example 1

3-Methyl-6-(2-(1-methyl-3-(pyrrolidin-1-yl)-1H-1,2,4-triazol-5-yl)ethyl)-2-(trifluoro-methyl)imidazo[1,2-b]pyridazine

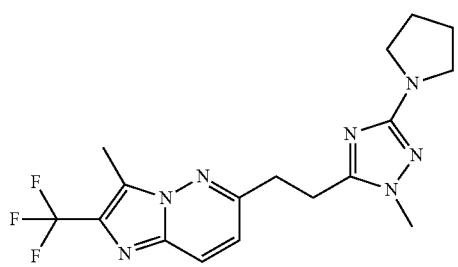

Step 1: 6-Iodo-3-methyl-2-(trifluoromethyl)imidazo[1,2-b]pyridazine

A mixture of 6-iodopyridazin-3-amine (CAS 187973-60-0; 2 g, 9.05 mmol) and 3-bromo-1,1,1-trifluorobutan-2-one (2.41 g, 11.8 mmol) in ethanol (40 ml) under an argon atmosphere was heated to 85° C. Stirring at that temperature was continued for 18 h. The brown solution was cooled to r.t. and concentrated to leave a brown orange sticky paste. This was triturated in a mixture of 10% aq. Na$_2$CO$_3$ and EtOH. The suspension was stirred at r.t. for 30 min. The product was collected by filtration, washed with H$_2$O and then with cyclohexane, and dried, providing the title compound (1.04 g, 35%) as brown solid.

MS: M=328.0 (M+H)$^+$

Step 2: 3-Methyl-2-(trifluoromethyl)-6-vinylimidazo[1,2-b]pyridazine

To a stirred solution of 6-iodo-3-methyl-2-(trifluoromethyl)imidazo[1,2-b]pyridazine (1.03 g, 3.15 mmol) at r.t. in DMF (20 ml) under an argon atmosphere were added tributyl(vinyl)stannane (1.05 g, 3.31 mmol) and Pd(Ph$_3$P)$_4$ (182 mg, 157 μmol). The mixture was degassed and back-filled with argon before it was heated to 120° C. Stirring at that temperature was continued for 17 hrs. The mixture was cooled to r.t., the insoluble material was filtered off and washed with 20 ml EtOAc. The filtrate was washed with H$_2$O. The aqueous phase was back extracted with EtOAc. The combined organics were washed with H$_2$O and brine, dried over MgSO$_4$, filtered and concentrated. The crude product was purified by column chromatography on silica gel using a n-heptane/EtOAc gradient, providing the title compound (541 mg, 76%) as orange solid.

MS: M=228.2 (M+H)$^+$

Step 3: 3-Methyl-2-(trifluoromethyl)imidazo[1,2-b]pyridazine-6-carbaldehyde

To a mixture of 3-methyl-2-(trifluoromethyl)-6-vinylimidazo[1,2-b]pyridazine (535 mg, 2.35 mmol) and osmium (VIII) oxide (4% solution in H$_2$O; 748 mg, 118 μmol) at r.t. in acetone (15 ml) under an argon atmosphere was added 4-methylmorpholine 4-oxide (50% solution in H2O 828 mg, 746 μl). The mixture (clear light yellow solution) was heated to 46° C. and stirring at that temperature was continued for 4 hrs. The solvent was then removed at the rotavapor and the dark residue was taken up in THF (20 ml) and water (5 ml). Sodium periodate (1.01 g, 4.71 mmol) was then added and the mixture was stirred at 46° C. for 16 hrs. During that time, the mixture slowly turned into a compact yellow suspension. The mixture was cooled to r.t. and quenched by the addition of 10% aq. Na$_2$SO$_3$ (30 ml), then extracted with CH$_2$Cl$_2$. The combined organics were washed with brine (50 ml), dried over MgSO$_4$, filtered and concentrated. The crude product was purified by silica gel chromatography using a n-heptane/EtOAc gradient as eluent, to provide the title compounds (164 mg, 30%) as light yellow solid.

MS: M=230.3 (M+H)$^+$

Step 4: (3-Methyl-2-(trifluoromethyl)imidazo[1,2-b]pyridazin-6-yl)methanol

To a stirred solution of 3-methyl-2-(trifluoromethyl)imidazo[1,2-b]pyridazine-6-carbaldehyde (155 mg, 676 μmol) at r.t. in methanol (3 ml) and dichloromethane (3 ml) was added sodium borohydride (51.2 mg, 1.35 mmol) in one portion. The mixture immediately turned from yellow to colorless. Stirring at r.t. was continued for 2 hrs 15. The mixture was diluted with CH$_2$Cl$_2$ and washed with H$_2$O. The aqueous phase was extracted with CH$_2$Cl$_2$. The combined organics were washed with brine, dried over MgSO₄, filtered and concentrated to leave the title compound (155 mg, 99%) as white solid.

MS: M=232.4 (M+H)⁺

Step 5: 6-(Chloromethyl)-3-methyl-2-(trifluoromethyl)imidazo[1,2-b]pyridazine To a stirred, cooled (0° C.) solution of (3-methyl-2-(trifluoromethyl)imidazo[1,2-b]pyridazin-6-yl)methanol (150 mg, 649 µmol) in dichloromethane (5 ml) under an argon atmosphere was added dropwise a solution of thionyl chloride (154 mg, 94.1 µl) in dichloromethane (2 ml). When the addition was complete, the ice bath was removed and stirring at r.t. was continued for 90 min. The mixture was concentrated to leave the title compound (161 mg, 99%) as an off-white solid.

MS: M=250.3 (M+H)⁺

Step 6: (3-Methyl-2-trifluoromethyl-imidazo[1,2-b]pyridazin-6-ylmethyl)-triphenyl-phosphonium chloride A mixture of 6-(chloromethyl)-3-methyl-2-(trifluoromethyl)imidazo[1,2-b]pyridazine (155 mg, 621 µmol) and triphenylphosphine (163 mg, 621 µmol) in ethanol (5 ml) and THF (5 ml) under an argon atmosphere was heated to 70° C. and stirring at that temperature was continued overnight. The mixture (clear colorless solution) was cooled to r.t. and concentrated to leave the title compound (298 mg, contains ca. 50% of an unidentified impurity) as an off-white solid.

MS: M=476.4 (M+H)⁺

Step 7: 1-Methyl-3-(pyrrolidin-1-yl)-1H-1,2,4-triazole-5-carbaldehyde

To stirred, cooled (0° C.) pyrrolidine-1-carbonitrile (5 g, 5.24 ml, 52.0 mmol) under an argon atmosphere was added dropwise 2,2-dichloroacetyl chloride (7.67 g, 5.00 ml, 52.0 mmol). The ice bath was then removed and stirring at r.t. was continued for 45 min. The reaction mixture was diluted with dichloromethane (30 ml), cooled in an ice bath, and treated with N-ethyldiisopropylamine (6.72 g, 9.08 ml, 52.0 mmol) (dropwise addition, the mixture turning from yellow to reddish brown). tert-Butyl 1-methylhydrazinecarboxylate (9.88 g, 10.0 ml, 67.6 mmol) was then added dropwise. The reaction mixture was heated to 50° C. for 1 hr. The mixture was cooled to 0° C., carefully treated with 2,2,2-trifluoroacetic acid (35.6 g, 24.0 ml, 312 mmol) and then heated again to 55° C. for 90 min. The mixture was cooled to r.t. After addition of more 2,2,2-trifluoroacetic acid (35.6 g, 24.0 ml, 312 mmol), the mixture was heated again to 55° C. and stirring at that temperature was continued for 30 min. The clear brown solution was cooled to r.t. and concentrated to leave a brown oil which was dissolved in CH₂Cl₂ and washed with saturated aqueous NH₄Cl solution. The organic phase was dried over MgSO₄, filtered and concentrated to leave the crude 5-dichloromethyl-1-methyl-3-pyrrolidin-1-yl-1H-[1,2,4]triazole as a brown oil.

The residue was taken up in dioxane (50 ml) and saturated aqueous Na₂CO₃ (100 ml) was added carefully. The orange slurry was heated to 100° C. for 1 hr. During that time the reaction mixture turned to a clear solution. It was then cooled to r.t. After addition of H₂O, the mixture was extracted with EtOAc. The combined organics were dried over MgSO₄, filtered and concentrated to leave the crude 1-methyl-3-(pyrrolidin-1-yl)-1H-1,2,4-triazole-5-carbaldehyde as a brown sticky solid which was dissolved in diethyl ether (400 ml) and then treated with Na₂SO₄ (20 g) and 40% aqueous NaHSO₃ solution (8 ml). After stirring for 1 h at r.t., the precipitate was collected by filtration and washed with Et₂O. The solid was taken up in CH₂Cl₂ (200 ml) and 10% aq. Na₂CO₃ (200 ml). The biphasic mixture was stirred at r.t. for 15 min. The layers were separated. The aqueous phase was back extracted with CH₂Cl₂. The combined organics were washed with brine, dried over MgSO₄, filtered and concentrated to leave the title compound (5.55 g, 59%) as yellow solid.

MS: M=181.2 (M+H)⁺

Step 8: (E)-3-methyl-6-(2-(1-methyl-3-(pyrrolidin-1-yl)-1H-1,2,4-triazol-5-yl)vinyl)-2-(trifluoromethyl)imidazo[1,2-b]pyridazine To a stirred suspension of ((3-methyl-2-(trifluoromethyl)imidazo[1,2-b]pyridazin-6-yl)methyl)-triphenyl-phosphonium chloride (290 mg, 283 µmol) at r.t. in THF (10 ml) under an argon atmosphere were added DBU (108 mg, 106 µl, 708 µmol) and 1-methyl-3-(pyrrolidin-1-yl)-1H-1,2,4-triazole-5-carbaldehyde (51.0 mg, 283 µmol). The mixture was then stirred at r.t. for over night, then concentrated. The crude product was purified by silica gel chromatography using a CH₂Cl₂/MeOH gradient as eluent, providing the title compound (94 mg, 85%) as yellow solid.

MS: M=378.3 (M+H)⁺

Step 9: 3-Methyl-6-(2-(1-methyl-3-(pyrrolidin-1-yl)-1H-1,2,4-triazol-5-yl)ethyl)-2-(trifluoro-methyl)imidazo[1,2-b]pyridazine To a stirred, yellow solution of (E)-3-methyl-6-(2-(1-methyl-3-(pyrrolidin-1-yl)-1H-1,2,4-triazol-5-yl)vinyl)-2-(trifluoro-methyl)imidazo[1,2-b]pyridazine (90 mg, 238 µmol) at r.t. in ethanol under an argon atmosphere was added Raney nickel (1 small spatula of 50% slurry in water). The mixture was degassed and then flushed with hydrogen. The reaction mixture was stirred for 3 hrs at r.t. The catalyst was filtered off and washed with ethanol. The filtrate was concentrated. The crude product was purified by silica gel chromatography using a CH₂Cl₂/MeOH gradient, providing the title compound (78 mg, 86%) as white sticky solid.

MS: M=380.5 (M+H)⁺

Example 2

2,3-Dimethyl-6-(2-(1-methyl-3-(pyrrolidin-1-yl)-1H-1,2,4-triazol-5-yl)ethyl)-imidazo[1,2-b]pyridazine

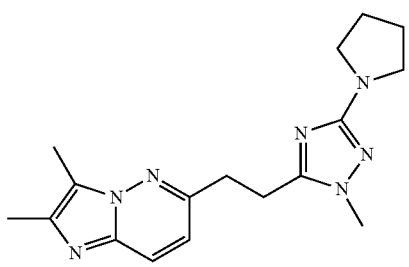 [SMILES: Cc1nc2ccc(CCc3nc(N4CCCC4)nn3C)nn2c1C]

In analogy to the procedures described in example 1, the title compound was prepared using 3-bromo-2-butanone in the 1st step. Off-white solid.
MS: M=326.4 (M+H)⁺

Example 3

3-Methyl-6-[(E)-2-(2-methyl-5-pyrrolidin-1-yl-2H-[1,2,4]triazol-3-yl)vinyl]-imidazo[1,2-b]pyridazine-2-carbonitrile

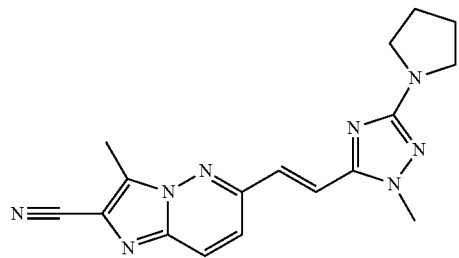 [SMILES: Cc1c(C#N)nc2ccc(/C=C/c3nc(N4CCCC4)nn3C)nn12]

Step 1: 6-Chloro-3-methyl-imidazo[1,2-b]pyridazine-2-carboxylic acid methyl ester To a solution of 6-chloro-pyridazin-3-ylamine (6 g, 46.3 mmol) in 1,2-dimethoxy ethane (300 ml) was added drop wise 3-bromo-2-oxo-butyric acid methyl ester (10.85 g, 55.6 mmol) at 25° C. The reaction mixture was heated to reflux for 18 hrs, then cooled to 25° C., and concentrated in vacuo. The crude product was purified by silica gel chromatography using 40% EtOAc/hexane as eluent to the title compound (5 g, 48%) as off white solid.
LC-MS (ESI): 226.2

Step 2: 6-Chloro-3-methyl-imidazo[1,2-b]pyridazine-2-carboxylic acid amide

To a solution of 6-chloro-3-methyl-imidazo[1,2-b]pyridazine-2-carboxylic acid methyl ester (1.5 g, 6.7 mmol) in acetonitrile (20 ml) in a sealed tube was added aqueous ammonia (28%; 100 ml), and the reaction mass was stirred at 100° C. for 10 hrs. Reaction mixture was diluted with water (50 ml) and extracted with EtOAc. The combined organics were washed with water and brine, dried over anhydrous Na₂SO₄ filtered, and concentrated. The crude product was purified by trituration with a mixture of CH₂Cl₂ and hexane, filtered and dried to give the title compound (0.7 g, 50%) as pale yellow solid.
LC-MS (ESI): 212.2

Step 3: 6-Chloro-3-methyl-imidazo[1,2-b]pyridazine-2-carbonitrile

To a solution of 6-chloro-3-methyl-imidazo[1,2-b]pyridazine-2-carboxylic acid amide (1.65 g, 7.8 mmol) in pyridine (4.8 ml) was added trifluoro acetic anhydride (1.65 ml, 11.8 mmol) at 10° C., and the mixture was stirred for 30 min at 10° C. followed by another 30 min at 25° C. The reaction mixture was diluted with water (5 ml), acidified (pH 1 to 2) with aqueous HCl (3N). The resultant precipitated solid was filtered and dried to give the title compound (1.3 g, 86%) as white solid.
LC-MS (ESI): 193.0

Step 4: 3-Methyl-6-[(E)-2-(2-methyl-5-pyrrolidin-1-yl-2H-[1,2,4]triazol-3-yl)-vinyl]-imidazo[1,2-b]pyridazine-2-carbonitrile The title compound was obtained from 6-chloro-3-methyl-imidazo[1,2-b]pyridazine-2-carbonitrile according to the procedures described in steps 2-8 of example 1. Yellow solid.
MS: M=335.4 (M+H)⁺

Example 4

3-Methyl-6-((1-methyl-5-(pyrrolidin-1-yl)-1H-1,2,4-triazol-3-yl)ethynyl)-2-(trifluoromethyl)imidazo[1,2-b]pyridazine

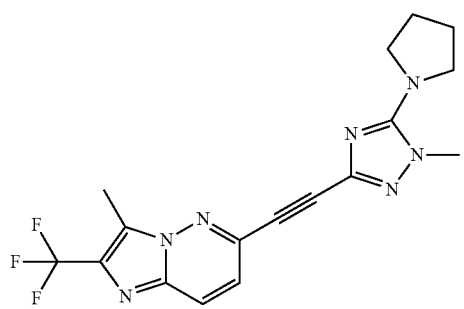 [SMILES: Cc1c(C(F)(F)F)nc2ccc(C#Cc3nc(N4CCCC4)n(C)n3)nn12]

Step 1: 3-Bromo-1-methyl-5-(pyrrolidin-1-yl)-1H-1,2,4-triazole

To a stirred solution of 3,5-dibromo-1-methyl-1H-1,2,4-triazole (CAS 23579-79-5; 1 g, 4.15 mmol) at r.t. in DMF (15 ml) under an argon atmosphere was added pyrrolidine (310 mg, 360 µl, 4.36 mmol). The mixture was heated to 125° C. for 1 day. The mixture was cooled to r.t., diluted with EtOAc and washed with H₂O. The aqueous phase was back extracted with EtOAc. The combined organics were washed with H₂O and brine, dried over MgSO₄, filtered and concentrated. The crude product was purified by silica gel chromatography using a CH₂Cl₂/MeOH 9:1 as eluent, providing the title compound (451 mg, 44%) as brown oil.
MS: M=231.1 (M+H)⁺

Step 2: 1-Methyl-5-(pyrrolidin-1-yl)-3-((trimethylsilyl)ethynyl)-1H-1,2,4-triazole To a stirred solution of 3-bromo-1-methyl-5-(pyrrolidin-1-yl)-1H-1,2,4-triazole (0.43 g, 1.73 mmol) and ethynyltrimethylsilane (212 mg, 452 µl, 2.16 mmol) at r.t. in DMF (5 ml) under an argon atmosphere were added triethylamine (350 mg, 480 µl, 3.46 mmol), copper(I) iodide (16.5 mg, 86.5 µmol) and bis(triphenylphosphine)palladium (II) chloride (60.7 mg, 86.5 µmol). The reaction mixture was evacuated and flushed with argon before it was heated to 120° C. for 1 day. The dark brown mixture was cooled to r.t., diluted with EtOAc and washed with H₂O. The aqueous phase was extracted with EtOAc. The combined organics were washed with H₂O and brine, dried over MgSO₄, filtered and concentrated. The crude product was purified by silica gel chromatography using a $CH_2Cl_2$/MeOH 9:1 as eluent, providing the title compound (91 mg, 21%) as off-white solid.
MS: M=249.1 (M+H)$^+$

Step 3: 3-Ethynyl-1-methyl-5-(pyrrolidin-1-yl)-1H-1,2,4-triazole

To a stirred, cooled (0° C.) solution of 1-methyl-5-(pyrrolidin-1-yl)-3-((trimethylsilyl)ethynyl)-1H-1,2,4-triazole (88 mg, 354 µmol) in THF (5 ml) under an argon atmosphere was added tetrabutylammonium fluoride 1 M solution in THF (709 µl, 709 µmol). Stirring at 0° C. was then continued for 1 hr. The reaction mixture was concentrated. The crude product was purified by silica gel chromatography using a $CH_2Cl_2$/MeOH 9:1 as eluent, providing the title compound (40 mg, 64%) as brown solid.

Step 4: 3-Methyl-6-((1-methyl-5-(pyrrolidin-1-yl)-1H-1,2,4-triazol-3-yl)ethynyl)-2-(trifluoro-methyl)imidazo[1,2-b]pyridazine To a stirred solution of 6-iodo-3-methyl-2-(trifluoromethyl)imidazo[1,2-b]pyridazine (described in example 1, step 1; 70 mg, 214 µmol) and 3-ethynyl-1-methyl-5-(pyrrolidin-1-yl)-1H-1,2,4-triazole (40 mg, 227 µmol) at r.t. in DMF (3 ml) under an argon atmosphere were added triethylamine (43.3 mg, 57.0 µl, 428 µmol), copper (I) iodide (2.04 mg, 10.7 µmol) and bis(triphenylphosphine)palladium (II) chloride (7.51 mg, 10.7 µmol). The mixture was degassed and flushed with argon before it was heated to 80° C. for 1 day. The dark brown mixture was cooled to r.t., diluted with EtOAc and washed with $H_2O$. The aqueous phase was back extracted with EtOAc. The combined organics were washed with $H_2O$ and brine, dried over $MgSO_4$, filtered and concentrated. The crude product was purified by silica gel chromatography using a $CH_2Cl_2$/MeOH 9:1 as eluent, providing the title compound (52 mg, 61%) as off-white solid.
MS: M=376.4 (M+H)$^+$

Example 5

3-Methyl-6-[2-(2-methyl-5-pyrrolidin-1-yl-2H-[1,2,4]triazol-3-yl)-ethyl]-imidazo[1,2-b]pyridazine-2-carbonitrile

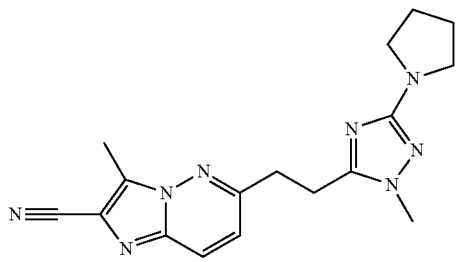 [SMILES: Cc1c(C#N)nc2ccc(CCc3nc(N4CCCC4)nn3C)nn12]

A solution of (E)-3-methyl-6-(2-(1-methyl-3-(pyrrolidin-1-yl)-1H-1,2,4-triazol-5-yl)vinyl)imidazo[1,2-b]pyridazine-2-carbonitrile (21.5 mg, 64.3 µmol) was hydrogenated in the presence of Lindlar catalyst (5 mg, 47.0 µmol) in ethanol (3 ml) for 2 hrs. The catalyst was filtered off and washed with EtOH. The solvent was evaporated. The crude product was purified by silica gel chromatography using a $CH_2Cl_2$/MeOH 9:1 as eluent, providing the title compound (1 mg, 5%) as light yellow solid.
MS: M=337.4 (M+H)$^+$

Example 6

3-Methyl-6-(2-(1-methyl-5-(pyrrolidin-1-yl)-1H-1,2,4-triazol-3-yl)ethyl)-2-(trifluoromethyl)imidazo[1,2-b]pyridazine

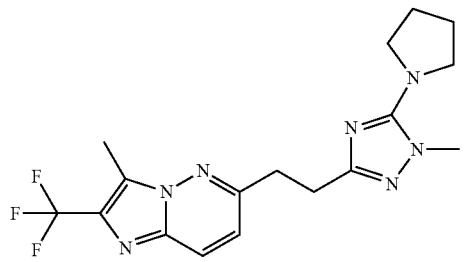 [SMILES: Cc1c(C(F)(F)F)nc2ccc(CCc3nc(N4CCCC4)n(C)n3)nn12]

To a stirred solution of 3-methyl-6-((1-methyl-5-(pyrrolidin-1-yl)-1H-1,2,4-triazol-3-yl)ethynyl)-2-(trifluoromethyl)imidazo[1,2-b]pyridazine (example 4; 49 mg, 123 µmol) at r.t. in ethanol (3 ml) and dichloromethane (3.00 ml) under an argon atmosphere was added Raney nickel (50% slurry in water (1 small spatula). The black suspension was degassed and flushed with $H_2$. The reaction mixture was stirred at r.t. under a hydrogen atmosphere for 2 hrs. The catalyst was filtered off and washed with ethanol. The filtrate was concentrated. The crude product was purified by silica gel chromatography using a $CH_2Cl_2$/MeOH 9:1 as eluent, providing the title compound (28 mg, 60%) as off-white solid.
MS: M=380.5 (M+H)$^+$

Example 7

2-(Difluoromethyl)-3-methyl-6-((1-methyl-3-(pyrrolidin-1-yl)-1H-1,2,4-triazol-5-yl)ethynyl)imidazo[1,2-b]pyridazine

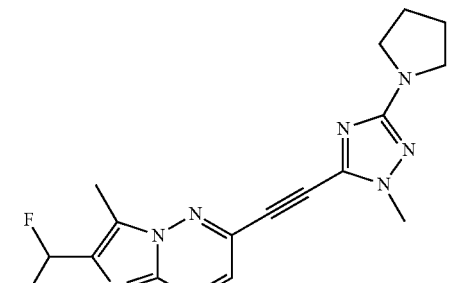

Step 1: 6-Chloro-3-methyl-imidazo[1,2-b]pyridazine-2-carboxylic acid

To a solution of 6-chloro-3-methyl-imidazo[1,2-b]pyridazine-2-carboxylic acid methyl ester (described in step 1 of example 3; 200 mg, 0.9 mmol) in THF (7 ml) was added a solution of lithium hydroxide monohydrate (112 mg, 2.7 mmol) in water (3 ml) at 0° C. The reaction mixture was stirred at 25° C. for 12 hrs. The solvent was removed under reduced pressure. The resultant crude material was diluted with water and washed with EtOAc. The aqueous layer was acidified (pH 5) with aqueous HCl solution (1N) at 0° C. and extracted with EtOAc. The combined organics were dried over anhydrous $Na_2SO_4$, filtered and concentrated to give the title compound (150 mg, 80%) as white solid.

LC-MS (ESI): 212.0

Step 2: (6-Chloro-3-methyl-imidazo[1,2-b]pyridazin-2-yl)-methanol

To a solution of 6-chloro-3-methyl-imidazo[1,2-b]pyridazine-2-carboxylic acid (2 g, 9.5 mmol) in THF (80 ml) were added n-methylmorpholine (freshly distilled; 3.1 ml, 28.4 mmol) and—dropwise—isobutyl chloroformate (6.2 ml, 47.4 mmol) in THF (20 ml) under argon atmosphere. The reaction mixture was stirred at 25° C. for 2 hrs. To this mixture was then added $NaBH_4$ (2 eq.) was added and stirred at 25° C. for 12 hrs. Then, a fresh lot of $NaBH_4$ (1equiv) was added to the mixture, and stirring was continued at 60° C. for another 3 hrs. The reaction mass was diluted dropwise with ice cold water (10 ml) and extracted with EtOAc. The combined organics was washed with brine, dried over anhydrous $Na_2SO_4$, filtered, and evaporated off in vacuo. The crude product was purified by silica gel chromatography using 3% MeOH in $CH_2Cl_2$ as eluent, to give the title compound (300 mg, 16%) as off white solid.

LC-MS (ESI): 198.0

Step 3: 6-Chloro-3-methylimidazo[1,2-b]pyridazine-2-carbaldehyde

To a stirred solution of (6-chloro-3-methyl-imidazo[1,2-b]pyridazin-2-yl)-methanol (277 mg, 1.4 mmol) at r.t. in chloroform under an argon atmosphere was added manganese (IV) oxide (609 mg, 7.01 mmol). The mixture was heated to 60° C. overnight, then cooled to r.t. and filtered. The filtrate was concentrated. The crude product was purified by silica gel chromatography using a $CH_2Cl_2$/MeOH 9:1 as eluent, providing the title compound (219 mg, 80%) as off-white solid.

MS: M=196.1 $(M+H)^+$

Step 4: 6-Chloro-2-(difluoromethyl)-3-methylimidazo[1,2-b]pyridazine

To a stirred solution of 6-chloro-3-methylimidazo[1,2-b]pyridazine-2-carbaldehyde (210 mg, 1.1 mmol) at r.t. in dichloromethane (10 ml) under an argon atmosphere was added diethylaminosulfur trifluoride (652 mg, 535 µl, 4.1 mmol) in one portion. The mixture was stirred at r.t. for 1 day. Then, it was poured into 20 ml of 10% aq. $KHCO_3$. The aqueous phase was extracted with $CH_2Cl_2$. The combined organics were washed with $H_2O$ and brine, dried over $MgSO_4$, filtered and concentrated. The crude product was purified by silica gel chromatography using a n-heptane/EtOAc as eluent, providing the title compound (197 mg, 84%) as off-white solid.

MS: M=218.3 $(M+H)^+$

Step 5: 2-(Difluoromethyl)-3-methyl-6-((1-methyl-3-(pyrrolidin-1-yl)-1H-1,2,4-triazol-5-yl)-ethynyl)imidazo[1,2-b]pyridazine In analogy to the procedure described in step 4 of example 4, 6-chloro-2-(difluoromethyl)-3-methyl-imidazo[1,2-b]pyridazine was reacted with 5-ethynyl-1-methyl-3-pyrrolidin-1-yl-1H[1,2,4]triazole (described in step 2 of example 12) to provide the title compound. Yellow solid.

MS: M=358.5 $(M+H)^+$

Example 8

2-(Difluoromethyl)-3-methyl-6-(2-(1-methyl-3-(pyrrolidin-1-yl)-1H-1,2,4-triazol-5-yl)ethyl)imidazo[1,2-b]pyridazine

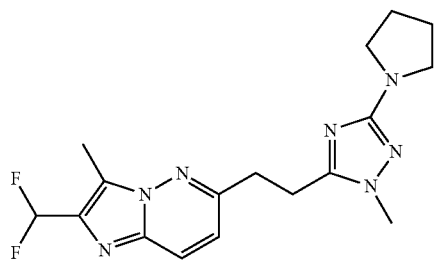 [SMILES: Cc1c(C(F)F)nc2ccc(CCc3nc(N4CCCC4)nn3C)nn12]

In analogy to the procedure described in example 6, the title compound was obtained from 2-(difluoromethyl)-3-methyl-6-((1-methyl-3-(pyrrolidin-1-yl)-1H-1,2,4-triazol-5-yl)-ethynyl)imidazo[1,2-b]pyridazine (example 7).

MS: M=362.5 $(M+H)^+$

Example 9

(E)-8-methoxy-3-methyl-6-(2-(1-methyl-3-(pyrrolidin-1-yl)-1H-1,2,4-triazol-5-yl)vinyl)-2-(trifluoromethyl)imidazo[1,2-b]pyridazine

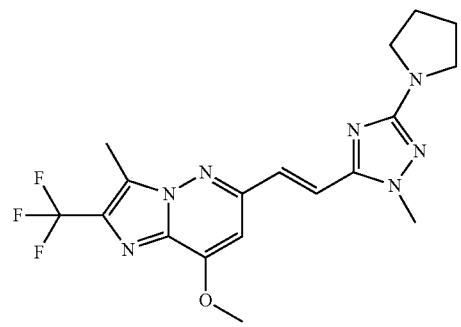 [SMILES: COc1cc(/C=C/c2nc(N3CCCC3)nn2C)nn2c(C)c(C(F)(F)F)nc12]

Step 1: 6-Chloro-4-methoxypyridazin-3-amine

To a stirred, cooled (0° C.) brown slurry of 4-bromo-6-chloropyridazin-3-amine (6 g, 28.8 mmol) in methanol (100 ml) under an argon atmosphere was added dropwise a solution of sodium methanolate 5.4 M solution in methanol (6.4 ml, 34.5 mmol) in methanol (50 ml). When the addition was complete, the ice bath was removed and stirring at r.t. was continued overnight. The dark brown slurry was concentrated. The crude product was purified by silica gel chromatography using a $CH_2Cl_2$/MeOH gradient as eluent. The product-containing fractions were combined and concentrated. The residue was taken up in cyclohexane (15 ml) and $CH_2Cl_2$ (5 ml). The suspension was stirred at r.t. for 2 hrs. The solid was collected by filtration, washed with cyclohexane and dried to provide the title compound (1.87 g, 40%) as off-white solid.
MS: M=160.1 (M+H)+

Step 2: 8-Methoxy-3-methyl-2-(trifluoromethyl) imidazo[1,2-b]pyridazine-6-carbaldehyde Starting from 6-chloro-4-methoxypyridazin-3-amine, the title compound was obtained in analogy to the procedures described in steps 1-3 of example 1. Light yellow solid.
MS: M=260.1 (M+H)+

Step 3: (2-Methyl-5-pyrrolidin-1-yl-2H-[1,2,4]tri-azol-3-yl)-methanol

To a solution of 2-methyl-5-pyrrolidin-1-yl-2H-[1,2,4] triazole-3-carbaldehyde (described in step 7 of example 1; 4 g, 22.2 mmol) at 25° C. in methanol (100 ml) and chloroform (100 ml) under argon was added sodium borohydride (1.76 g, 46.78 mmol) portion wise for 5 min. The reaction mixture was stirred at 25° C. for 2 hrs. Water (25 ml) was added to the reaction mixture which was stirred at 25° C. for 30 min, then diluted with CH2Cl2. The organic layer was separated. The aqueous layer was re-extracted with CH2Cl2. The combined organics were washed with brine, dried over anhydrous Na2SO4, filtered and concentrated to give the title compound (3.5 g, 86%) as off white solid.
LC-MS (ESI): 183.0 (M+H).

Step 4: 5-Chloromethyl-1-methyl-3-pyrrolidin-1-yl-1H-[1,2,4]triazole

To a solution of (2-methyl-5-pyrrolidin-1-yl-2H-[1,2,4] triazol-3-yl)-methanol (3 g, 16.5 mmol) in CH2Cl2 (10 ml) under an argon atmosphere at 0° C. was added dropwise triethylamine (3.6 ml, 24.7 mmol) followed by thionyl chloride (1.43 ml, 19.8 mmol). The reaction mixture was allowed to stir at 25° C. for 4 hrs, then concentrated. The crude product was purified by silica gel chromatography using 70% EtOAc/hexane as eluent, to provide the title compound (2 g, 60%) as off white solid.
LC-MS (ESI): 201.0 (M+H).

Step 5: (2-Methyl-5-pyrrolidin-1-yl-2H-[1,2,4]tri-azol-3-ylmethyl)-triphenyl-phosphonium chloride To a solution of 5-chloromethyl-1-methyl-3-pyrrolidin-1-yl-1H-[1,2,4]triazole (2 g, 10.0 mmol) in acetonitrile (150 ml) was added triphenyl phosphine (2.6 g, 10.0 mmol) at 25° C. The reaction mixture was refluxed for 12 hrs, then concentrated. The residue was triturated with diethyl ether (100 ml) to afford the title compound (4 g, 94%) as off white solid.
LC-MS (ESI): 427.2

Step 6: (E)-8-Methoxy-3-methyl-6-(2-(1-methyl-3-(pyrrolidin-1-yl)-1H-1,2,4-triazol-5-yl)vinyl)-2-(trifluoromethyl)imidazo[1,2-b]pyridazine In analogy to the procedure described in step 8 of example 1,8-methoxy-3-methyl-2-(trifluoro-methyl)imidazo[1,2-b] pyridazine-6-carbaldehyde was reacted with ((1-methyl-3-(pyrrolidin-1-yl)-1H-1,2,4-triazol-5-yl)methyl)triphenyl-phosphonium chloride to provide the title compound. Yellow solid.
MS: M=408.4 (M+H)+

Example 10

8-Methoxy-3-methyl-6-(2-(1-methyl-3-(pyrrolidin-1-yl)-1H-1,2,4-triazol-5-yl)ethyl)-2-(trifluoromethyl) imidazo[1,2-b]pyridazine

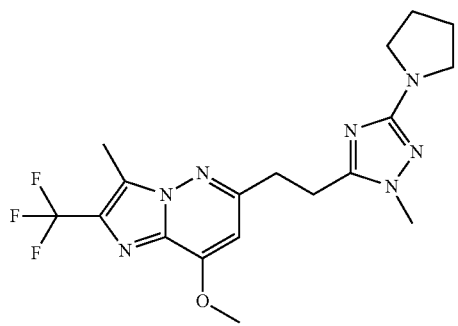 [SMILES: COc1cc(CCc2nc(N3CCCC3)nn2C)nn2c(C)c(C(F)(F)F)nc12]

In analogy to the procedure described in step 9 of example 1, (E)-8-methoxy-3-methyl-6-(2-(1-methyl-3-(pyrrolidin-1-yl)-1H-1,2,4-triazol-5-yl)vinyl)-2-(trifluoromethyl)imidazo [1,2-b]pyridazine was converted to the title compound. Off-white solid.
MS: M 410.4 (M+H)+

Example 11

6,7-Dimethyl-2-(2-(1-methyl-3-(pyrrolidin-1-yl)-1H-1,2,4-triazol-5-yl)ethyl)imidazo[1,2-f][1,2,4]triazin-4-ol

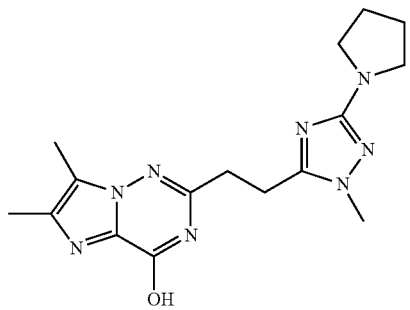 [SMILES: Cc1nc2c(O)nc(CCc3nc(N4CCCC4)nn3C)nn2c1C]

Step 1: Methyl 4,5-dimethyl-1H-imidazole-2-carboxylate

To a suspension at 0° C. under an argon atmosphere of 4,5-dimethyl-1H-imidazole-2-carboxylic acid (4.422 g, 31.6 mmol) in methanol (100 ml) was added dropwise thionyl chloride (37.5 g, 23.0 ml, 316 mmol). The mixture was stirred at 750 for 5 hrs. After cooling to r.t the solvent was evaporated. The residue was taken up in CH2Cl2, washed with aqueous saturated NaHCO3 solution, dried over MgSO4, filtered and evaporated. The remaining aqueous phase was extracted with CH2Cl2/MeOH 9:1. The organic was dried over MgSO4, filtered and evaporated. The two crops of products were combined to give the title compound (2.4 g, 50%) as brown solid.
MS: M=155.1 (M+H)+

Step 2: 1-Amino-4,5-dimethyl-1H-imidazole-2-carboxylic acid methyl ester

To a suspension of methyl 4,5-dimethyl-1H-imidazole-2-carboxylate (1.2 g, 7.78 mmol) in DMF (60 ml) at −10° under an argon atmosphere was added dropwise lithium bis(trimethylsilyl)amide 1 M in THF (7.78 ml, 7.78 mmol). The mixture was stirred for 1 hr and O-(diphenylphosphoryl) hydroxylamine (2.36 g, 10.1 mmol) was added at 0°. The mixture was stirred at r.t. for 18 hrs. The mixture was filtered, washed with $CH_2Cl_2$ and the solvents were evaporated to dryness. The residue was taken up in water and extracted with AcOEt. The combined organics was dried over $MgSO_4$, filtered and evaporated. The crude product was purified by silica gel chromatography using a $CH_2Cl_2$/MeOH gradient as eluent, providing the title compound (1.05 g, 80%) as viscous yellow oil.

MS: M=170.1 $(M+H)^+$

Step 3: 1-Amino-4,5-dimethyl-1H-imidazole-2-carboxamide

A solution of methyl 1-amino-4,5-dimethyl-1H-imidazole-2-carboxylate (1.4 g, 8.28 mmol) in ammonia in MeOH 7 M (100 ml) was heated in a sealed autoclave at 900 overnight (4 bar). After cooling to r.t., the solvent was evaporated to dryness. The title compound (1.18 g, 93%) was obtained as off-white solid.

MS: M=155.2 $(M+H)^+$

Step 4: (E)-Methyl 3-(1-methyl-3-(pyrrolidin-1-yl)-1H-1,2,4-triazol-5-yl)acrylate To a solution at r.t under Ar of 1-methyl-3-(pyrrolidin-1-yl)-1H-1,2,4-triazole-5-carbaldehyde (example 1, step 7; 1 g, 5.55 mmol) in THF (20 ml) was added DBU (2.11 g, 2.09 ml, 13.9 mmol) and (2-methoxy-2-oxoethyl)triphenylphosphonium bromide (2.3 g, 5.55 mmol). The mixture was stirred at r.t overnight. The solvent was evaporated. The crude product was purified by silica gel chromatography using a n-heptane/EtOAc gradient as eluent, providing the title compound (911 mg, 70%) as yellow solid.

MS: M=237.2 $(M+H)^+$

Step 5: Methyl 3-(1-methyl-3-(pyrrolidin-1-yl)-1H-1,2,4-triazol-5-yl)propanoate A solution of (E)-methyl 3-(1-methyl-3-(pyrrolidin-1-yl)-1H-1,2,4-triazol-5-yl)acrylate (0.91 g, 3.85 mmol) with in ethanol (15 ml) was hydrogenated at r.t for 2 hrs. The catalyst was filtered and washed with EtOH. The solvent was evaporated to provide the product (910 mg, 99%) as white solid.

MS: M=239.2 $(M+H)^+$

Step 6: 3-(1-Methyl-3-(pyrrolidin-1-yl)-1H-1,2,4-triazol-5-yl)propanoic acid To a solution at r.t under Ar of methyl 3-(1-methyl-3-(pyrrolidin-1-yl)-1H-1,2,4-triazol-5-yl)propanoate (0.91 g, 3.82 mmol) in MeOH (15 ml) was added 2M NaOH (5.73 ml, 11.5 mmol). The solution was stirred at r.t overnight. The solvent was evaporated. The solid was dissolved in 10 ml water and acidified to pH 2 with 3N HCl. The product was extracted with $CH_2Cl_2$/MeOH 9:1, dried over $MgSO_4$, filtered and evaporated to provide the title compound (990 mg, quant.) as white solid.

MS: M=225.2 $(M+H)^+$

Step 7: 4,5-Dimethyl-1-(3-(1-methyl-3-(pyrrolidin-1-yl)-1H-1,2,4-triazol-5-yl)propanamido)-1H-imidazole-2-carboxamide To a solution of 3-(1-methyl-3-(pyrrolidin-1-yl)-1H-1,2,4-triazol-5-yl)propanoic acid (0.37 g, 1.65 mmol) in 1-methyl-2-pyrrolidone (1.6 ml) was added 1,1'-carbonyldiimidazole (268 mg, 1.65 mmol). The reaction mixture was stirred at r.t. until gas formation ceased (10 min). Then, 1-amino-4,5-dimethyl-1H-imidazole-2-carboxamide (254 mg, 1.65 mmol) was added and the mixture was stirred at 1200 overnight. After cooling to r.t the mixture was diluted with EtOAc and washed with 10% aqueous $NaHCO_3$ solution. The organic layer was dried over $MgSO_4$, filtered and evaporated. The aqueous layer was extracted with $CH_2Cl_2$. The organic layer were dried over MgSO4, filtered and evaporated. The crude product from both extractions were combined and purified by silica gel chromatography using a $CH_2Cl_2$/MeOH gradient to provide the title compound (127 mg, 21%) as light yellow solid.

MS: M=361.5 (M+H)

Step 8: 6,7-Dimethyl-2-(2-(1-methyl-3-(pyrrolidin-1-yl)-1H-1,2,4-triazol-5-yl)ethyl)imidazo[1,2-f][1,2,4]triazin-4-ol A mixture of 4,5-dimethyl-1-(3-(1-methyl-3-(pyrrolidin-1-yl)-1H-1,2,4-triazol-5-yl)propan-amido)-1H-imidazole-2-carboxamide (70 mg, 155 µmol) and sodium carbonate (41.2 mg, 388 µmol) in ethanol (1.4 ml) and water (1.4 ml) was stirred at 110° for 8 hrs. After cooling to r.t the solvent was evaporated. The mixture was dissolved in 3 ml water and extracted twice with 100 ml $CH_2Cl_2$/MeOH 9:1. The organics were dried over MgSO4, filtered and evaporated.

The crude product was purified by silica gel chromatography using a $CH_2Cl_2$/MeOH gradient, providing the title compound (40 mg, 76%) as

MS: M=343.5 $(M+H)^+$

Example 12

8-Methoxy-2,3-dimethyl-6-(2-(1-methyl-3-(pyrrolidin-1-yl)-1H-1,2,4-triazol-5-yl)ethyl)imidazo[1,2-b]pyridazine

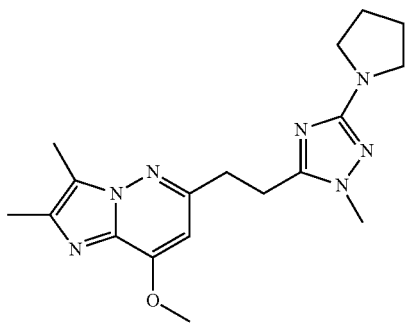 [SMILES: COc1cc(CCc2nc(N3CCCC3)nn2C)nn2c(C)c(C)nc12]

Step 1: 6-Chloro-8-methoxy-2,3-dimethylimidazo[1,2-b]pyridazine

To a stirred suspension of 6-chloro-4-methoxypyridazin-3-amine (200 mg, 1.25 mmol; described in example 9, step 1) at r.t. in EtOH (5 ml) under an argon atmosphere was added 3-bromobutan-2-one (284 mg, 197 µl, 1.88 mmol) in one portion. The mixture was heated to 90° C. and stirred for 2 hrs. After cooling to r.t. sodium bicarbonate (158 mg, 1.88 mmol, Eq: 1.5) was added and the mixture was heated again to 90° C. and stirred overnight, then concentrated. The crude product was purified by silica gel chromatography using a $CH_2Cl_2$/MeOH gradient, providing the title compound (163 mg, 61%). Off-white solid.

MS: M=212.2 $(M+H)^+$

Step 2: 5-Ethynyl-1-methyl-3-(pyrrolidin-1-yl)-1H-1,2,4-triazole

To a stirred mixture of 1-methyl-3-(pyrrolidin-1-yl)-1H-1,2,4-triazole-5-carbaldehyde (described in example 1, step 7; 2.06 g, 11.4 mmol) and potassium carbonate (3.16 g, 22.9 mmol) at r.t. in methanol (75 ml) under an argon atmosphere was added dropwise a solution of dimethyl 1-diazo-2-oxopropylphosphonate (2.64 g, 2.1 ml, 13.7 mmol) in methanol (15 ml). Stirring at r.t. was then continued for 3 hrs. The mixture was diluted with diethyl ether and washed with 10% $NaHCO_3$ solution. The aqueous phase was extracted with diethylether. The combined organics were washed with $H_2O$ and brine, dried over $MgSO_4$, filtered and concentrated. The crude product was purified by silica gel chromatography using a $CH_2Cl_2$/MeOH gradient as eluent, providing the title compound (725 mg, 36%) as off-white solid.

MS: M 177.2 $(M+H)^+$

Step 3: 8-Methoxy-2,3-dimethyl-6-(2-methyl-5-pyrrolidin-1-yl-2H-[1,2,4]triazol-3-ylethynyl)-imidazo[1,2-b]pyridazine To a stirred solution of 6-chloro-8-methoxy-2,3-dimethylimidazo[1,2-b]pyridazine (150 mg, 709 µmol) at r.t. in DMF (5 ml) under an argon atmosphere were added 5-ethynyl-1-methyl-3-(pyrrolidin-1-yl)-1H-1,2,4-triazole (137 mg, 780 µmol), triethylamine (143 mg, 196 µl, 1.42 mmol), copper (I) iodide (6.75 mg, 35.4 µmol) and bis(triphenylphosphine)palladium (II) chloride (24.9 mg, 35.4 µmol). The mixture was degassed and flushed with argon before it was heated to 80° C. overnight. The dark brown mixture was cooled to r.t., diluted with EtOAc and washed with $H_2O$. The aqueous phase was back extracted with EtOAc. The combined organics were washed with $H_2O$ and brine, dried over $MgSO_4$, filtered and concentrated. The crude product was isolated by silica gel chromatography using $CH_2Cl_2$/MeOH gradient as eluent, providing the title compound (18 mg, 6%) as off-white amorphous solid.

MS: M 352.5 $(M+H)^+$

Step 4: 8-Methoxy-2,3-dimethyl-6-(2-(1-methyl-3-(pyrrolidin-1-yl)-1H-1,2,4-triazol-5-yl)ethyl)imidazo[1,2-b]pyridazine The title compound was obtained in analogy to the procedure described in example 6. Off-white solid.
MS: M 356.5 $(M+H)^+$

Example 13

4-Methoxy-6,7-dimethyl-2-(2-(1-methyl-3-(pyrrolidin-1-yl)-1H-1,2,4-triazol-5-yl)ethyl)imidazo[1,2-f][1,2,4]triazine

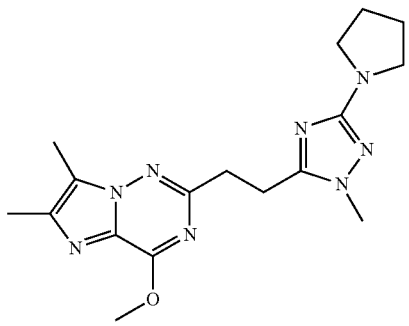 [SMILES: COc1nc(CCc2nc(N3CCCC3)nn2C)nn2c(C)c(C)nc12]

A mixture of 6,7-dimethyl-2-(2-(1-methyl-3-(pyrrolidin-1-yl)-1H-1,2,4-triazol-5-yl)ethyl)imidazo[1,2-f][1,2,4]triazin-4-ol (described in example 11; 28.8 mg, 84.1 µmol) and phosphoryl trichloride (1.28 g, 776 µl, 8.33 mmol) was refluxed under an argon atmosphere overnight. The reaction mixture was cooled to r.t., then treated with MeOH (2 ml) and stirred for 5 min. The reaction mixture was concentrated, diluted with $H_2O$ and extracted with $CH_2Cl_2$/MeOH 9:1. The combined organics were washed with aqueous saturated $NaHCO_3$ solution and water, dried over $MgSO_4$ filtered and evaporated. The crude product was purified by silica gel chromatography using $CH_2Cl_2$/MeOH gradient as eluent, providing the title compound (15 mg, 50%) as white solid.

MS: M=357.6 $(M+H)^+$

Example 14

5-[2-(2-Methyl-5-pyrrolidin-1-yl-2H-[1,2,4]triazol-3-yl)-ethyl]-2,3-dihydro-1H-3b,4,8-triaza-cyclopenta[a]indene

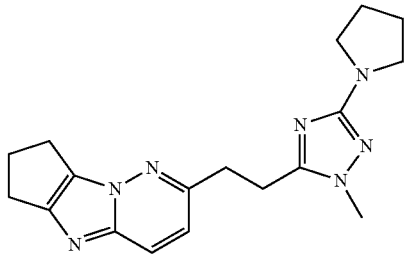 [SMILES: Cn1nc(N2CCCC2)nc1CCc1ccc2nc3c(n2n1)CCC3]

Step 1: 2-Bromo-cyclopentanone

A mixture of cyclopentanone (1 g, 11.9 mmol) and N-bromosuccinimide (2.1 g, 11.9 mmol) were triturated with para-toluenesulfonic acid (0.226 g, 1.2 mmol) for 10 min. The resultant reaction mixture was allowed to stir 25° C. for 2 hrs, then diluted with water and extracted with EtOAc. The combined organics were washed with water, dried over anhydrous $Na_2SO_4$, filtered, and concentrated. The crude product was purified by silica gel chromatography using CH$_2$Cl$_2$ as eluent to give the title compound (1.2 g, 62%) as pale yellow oily liquid. The compound was immediately used in the next step.

GC-MS (ESI): 162

Step 2: 5-Chloro-2,3-dihydro-1H-3b,4,8-triaza-cyclopenta[a]indene

To a solution of 6-chloro-pyridazin-3-ylamine (1 g, 7.7 mol) in 1,2-dimethoxy ethane (80 ml) was added dropwise 2-bromo-cyclopentanone (1.5 g, 9.3 mmol) at 25° C. The resultant reaction mixture was heated to reflux for 20 hrs. The mixture was cooled to 25° C. and filtered, then concentrated. The crude product was purified by silica gel chromatography using 30% EtOAc/hexane as eluent to give the title compound (0.5 g, 33%) as yellow solid.

LC-MS (ESI): 193.0

Step 3: 5-[2-(2-Methyl-5-pyrrolidin-1-yl-2H-[1,2,4]triazol-3-yl)-ethyl]-2,3-dihydro-1H-3b,4,8-triaza-cyclopenta[a]indene The title compound was obtained in analogy to the procedures described in step 3 and 4 of example 13. Yellow solid.

MS: M=338.5 (M+H)$^+$

Example 15

4-Chloro-6,7-dimethyl-2-(2-(1-methyl-3-(pyrrolidin-1-yl)-1H-1,2,4-triazol-5-yl)ethyl)imidazo[1,2-f][1,2,4]triazine

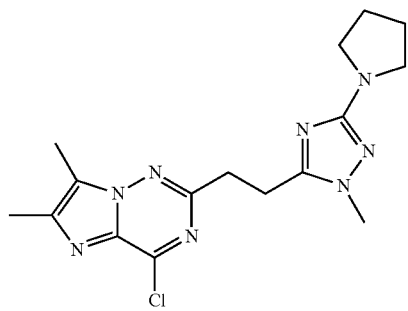 [SMILES: Cc1nc2c(Cl)nc(CCc3nc(N4CCCC4)nn3C)nn2c1C]

A mixture of 6,7-dimethyl-2-(2-(1-methyl-3-(pyrrolidin-1-yl)-1H-1,2,4-triazol-5-yl)ethyl)imidazo[1,2-f][1,2,4]triazin-4-ol (described in example 11; 40 mg, 117 μmol) and phosphoryl trichloride (1.77 g, 1.08 ml, 11.6 mmol) was refluxed under an argon atmosphere for 4 hrs. The reaction mixture was concentrated. The residue was diluted with 5 ml water and extracted with CH$_2$Cl$_2$/MeOH 9:1. The combined organics were washed with 10 ml aqueous saturated sol NaHCO3 solution and water, dried over MgSO4, filtered and concentrated. The crude product was purified by silica gel chromatography using CH$_2$Cl$_2$/MeOH gradient as eluent, providing the title compound (32 mg, 75%) as colorless, waxy solid.

MS: M=361.6 (M+H)$^+$

Example 16

2,3,8-trimethyl-6-(2-(1-methyl-3-(pyrrolidin-1-yl)-1H-1,2,4-triazol-5-yl)ethyl)-imidazo[1,2-b]pyridazine

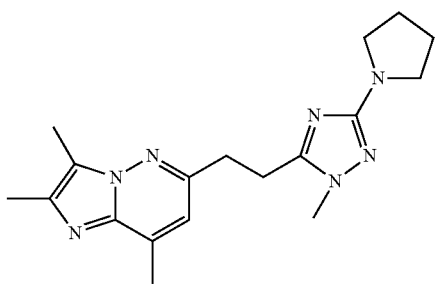 [SMILES: Cc1nc2c(C)cc(CCc3nc(N4CCCC4)nn3C)nn2c1C]

Step 1: 6-Chloro-4-methylpyridazin-3-amine and 6-chloro-5-methylpyridazin-3-amine A mixture of 3,6-dichloro-4-methylpyridazine (5 g, 30.7 mmol) and concentrated NH4OH solution (100 ml) was heated to 1200 in a sealed autoclave for 18 hrs at 6 bar. The mixture was cooled to r.t, diluted with water (200 ml) and stirred in an ice bath for 2 hrs. The solid was collected by filtration, washed with water and dried. The filtrate was extracted with CH$_2$Cl$_2$/MeOH (9:1). The organic was washed with brine, dried over MgSO$_4$, filtered and evaporated. The precipitate from the reaction mixture and the solid isolated by extraction were combined. This crude product was purified by column chromatography using a CH$_2$Cl$_2$/MeOH gradient as eluent, to provide 6-chloro-4-methyl-pyridazin-3-amine (456 mg, 10%) and 6-chloro-5-methyl-pyridazin-3-amine (350 mg, 8%), both as off-white solids.

MS: M=144.1 (M+H)$^+$ (both isomers)

Step 2: 6-Chloro-2,3,8-trimethylimidazo[1,2-b]pyridazine

In analogy to the procedure described in step 1 of example 1, the title compound was reacted with 3-bromo-2-butanone. Orange solid.

MS: M=196.1 (M+H)$^+$

Step 3: 2,3,8-Trimethyl-6-(2-(1-methyl-3-(pyrrolidin-1-yl)-1H-1,2,4-triazol-5-yl)ethyl)imidazo[1,2-b]pyridazine The title compound was prepared in analogy to the procedures described in step 4 of example 4 and in example 6. White solid

MS: M=340.6 (M+H)$^+$

Example 17

2,3,7-Trimethyl-6-((1-methyl-3-(pyrrolidin-1-yl)-1H-1,2,4-triazol-5-yl)ethynyl)imidazo[1,2-b]pyridazine

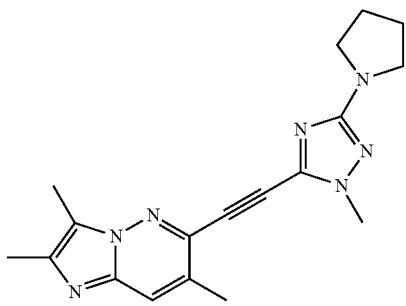 [SMILES: Cc1cc2nc(C)c(C)n2nc1C#Cc1nc(N2CCCC2)nn1C]

The title compound was prepared according to the procedure described in step 1 of example 1 reacting 3-bromo-2-butanone with 6-chloro-5-methylpyridazin-3-amine (described in step 1 of example 16) and then following the method described in step 4 of example 4. Orange solid.
MS: M=336.5 (M+H)+

Example 18

2,3,7-Trimethyl-6-(2-(1-methyl-3-(pyrrolidin-1-yl)-1H-1,2,4-triazol-5-yl)ethyl)imidazo[1,2-b]pyridazine

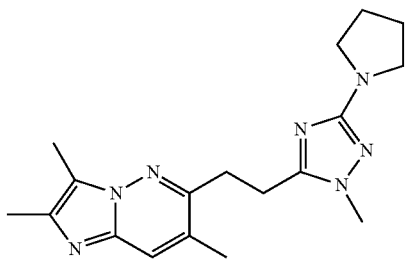 [SMILES: Cc1cc2nc(C)c(C)n2nc1CCc1nc(N2CCCC2)nn1C]

The title compound was obtained from 2,3,7-trimethyl-6-((1-methyl-3-(pyrrolidin-1-yl)-1H-1,2,4-triazol-5-yl)ethynyl) imidazo[1,2-b]pyridazine according to the procedure described in example 6. Light yellow solid.
MS: M=340.6 (M+H)+

Example 19

2,3-Dimethyl-6-(2-(1-methyl-3-(pyrrolidin-1-yl)-1H-1,2,4-triazol-5-yl)ethyl)-8-(pyrro-lidin-1-yl)imidazo[1,2-b]pyridazine

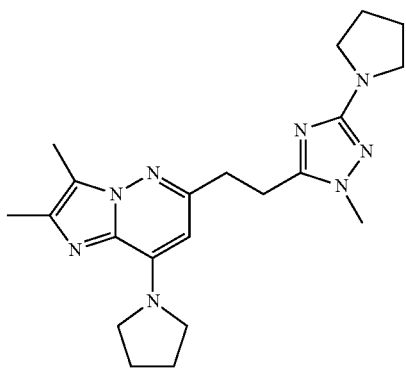 [SMILES: Cc1nc2c(N3CCCC3)cc(CCc3nc(N4CCCC4)nn3C)nn2c1C]

Step 1: 6-Chloro-4-(pyrrolidin-1-yl)pyridazin-3-amine

A mixture of 4-bromo-6-chloropyridazin-3-amine (2 g, 9.59 mmol), pyrrolidine (6.82 g, 7.93 ml, 95.9 mmol) and acetonitrile (45 ml) was stirred at 80° C. under an argon atmosphere for 17 hrs. The dark compact suspension was cooled to r.t., diluted with CH$_2$Cl$_2$ and washed with 100 ml 10% aqueous NaHCO$_3$ solution. The aqueous phase was extracted with CH$_2$Cl$_2$. The combined organics were washed with H$_2$O and brine, dried over MgSO$_4$, filtered and concentrated. The crude product was purified by silica gel chromatography using an n-heptane/EtOAc gradient as eluent to obtain the title compound (809 mg, 42%) as brown solid.
MS: M=199.1 (M+H)+

Step 2: 2,3-Dimethyl-8-(pyrrolidin-1-yl)imidazo[1,2-b]pyridazine-6-carbaldehyde

The title compound was obtained in analogy to the procedures described in step 1 of example 12 and steps 2 and 3 of example 1. Light yellow solid.
MS: M=245.5 (M+H)+

Step 3: (E)-2,3-Dimethyl-6-(2-(1-methyl-3-(pyrrolidin-1-yl)-1H-1,2,4-triazol-5-yl)vinyl)-8-(pyrrolidin-1-yl)imidazo[1,2-b]pyridazine In analogy to the procedure described in step 8 of example 1 2,3-dimethyl-8-(pyrrolidin-1-yl)imidazo[1,2-b]pyridazine-6-carbaldehyde was reacted with ((1-methyl-3-(pyrrolidin-1-yl)-1H-1,2,4-triazol-5-yl)methyl)triphenylphosphonium chloride (described in step 5 of example 9) to give the title compound. Light yellow solid.
MS: M=393.6 (M+H)+

Example 20

4-Chloro-6,7-dimethyl-2-(2-(1-methyl-5-(pyrrolidin-1-yl)-1H-1,2,4-triazol-3-yl)ethyl)-imidazo[1,2-f][1,2,4]triazine

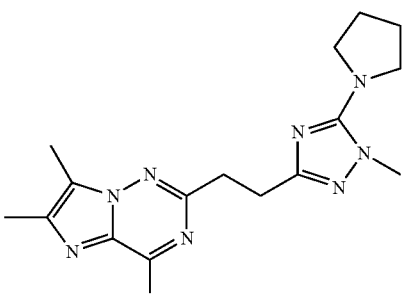

Step 1: 3-(Dichloromethyl)-1-methyl-5-(pyrrolidin-1-yl)-1H-1,2,4-triazole

Pyrrolidine-1-carbonitrile (5 g, 5.24 ml, 52.0 mmol) was cooled to 0° C. Then, 2,2-dichloroacetyl chloride (7.67 g, 5.00 ml, 52.0 mmol) was added dropwise. The reaction mixture turned red. After ca. 10 min. precipitation took place. After 15 minutes CH$_2$Cl$_2$ (30 ml) was added. The reaction mixture was cooled using an ice bath. Methylhydrazine (2.4 g, 2.74 ml, 52.0 mmol) was added dropwise and the reaction mixture was stirred for 1 h at 4° C. Then it was heated to 50° C. After 1 hr the reaction mixture was diluted with $CH_2Cl_2$ (200 ml) and washed with sat $NH_4Cl$. The aqueous layer was washed with $CH_2Cl_2$. The organic layers were dried over $Na_2SO_4$ and concentrated in vacuo affording the title compound (8.7 g, 71%) as amorphous yellow solid.
MS: M=235.1 $(M+H)^+$ Step 2: 1-Methyl-5-(pyrrolidin-1-yl)-1H-1,2,4-triazole-3-carbaldehyde A solution of 3-(dichloromethyl)-1-methyl-5-(pyrrolidin-1-yl)-1H-1,2,4-triazole (8.7 g, 37.1 mmol) in dioxane (50.0 ml) was treated with sat. $Na_2CO_3$ (100 ml). The reaction mixture was heated to 100° C. and stirred for 90 min. After 1 hr the reaction mixture was poured into $H_2O$ and extracted with EtOAc. The combined organic layers were dried over $Na_2SO_4$ and concentrated in vacuo affording the product as orange oil (5.93 g, 89%).
MS: M=181.2 $(M+H)^+$ Step 3: 4-Chloro-6,7-dimethyl-2-(2-(1-methyl-5-(pyrrolidin-1-yl)-1H-1,2,4-triazol-3-yl)ethyl)imidazo[1,2-f][1,2,4]triazine In analogy to the procedures described in steps 1-5 of example 11 and in example 15, the title compound was obtained as off-white solid.
MS: M=361.5 $(M+H)^+$ Example 21

(2-Methyl-6-(2-(1-methyl-3-(pyrrolidin-1-yl)-1H-1,2,4-triazol-5-yl)ethyl)imidazo[1,2-b]-pyridazin-3-yl)methanol

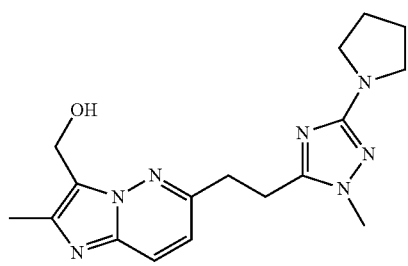 [SMILES: Cc1nc2ccc(CCc3nc(N4CCCC4)nn3C)nn2c1CO]

Step 1: 6-Chloro-2-methyl-imidazo[1,2-b]pyridazine

The title compound was prepared in analogy to the procured described in step 1 of example 1, starting from 6-chloro-pyridazin-3-ylamine and 1-bromo-propan-2-one. Light yellow solid.
MS: M=168.2 $(M+H)^+$ Step 2: 6-Chloro-2-methyl-imidazo[1,2-b]pyridazine-3-carbaldehyde A solution of 6-chloro-2-methyl-imidazo[1,2-b]pyridazine (8 g, 47.73 mmol) and 1,3,5,7-tetraaza-tricyclo[3.3.1.1*3,7*]decane (70.7 g, 477.3 mmol) in TFA (320 ml) was heated at 60° C. for 10 days. Volatilities removed in vacuo. The resultant residue was dissolved in $CH_2Cl_2$ (1000 ml) and washed with water. The aqueous layer was re-extracted with $CH_2Cl_2$. The combined organic layer was dried over anhydrous $Na_2SO_4$, filtered, and concentrated. The crude product was purified by silica gel chromatography using a hexane/EtOAc gradient to provide the title compound (2.2 g, 23%) as pale yellow solid.
MS: M=196.0 $(M+H)^+$ Step 3: (6-Chloro-2-methyl-imidazo[1,2-b]pyridazin-3-yl)-methanol To a solution of 6-chloro-2-methyl-imidazo[1,2-b]pyridazine-3-carbaldehyde (2.1 g, 10.8 mmol) in MeOH (100 ml) was added $NaBH_4$ (0.53 g, 14 mmol) at 0° C. The reaction mixture was stirred for 1 h at 25° C., then diluted with ice cold water, and extracted with $CH_2Cl_2$. The combined organics was dried over anhydrous $Na_2SO_4$, filtered, and concentrated. The crude product was purified by triturating with a mixture of $CH_2Cl_2$ and MeOH to give the title compound (2.0 g, 94%) as white solid.
MS: M=198.0 $(M+H)^+$ Step 4: [2-Methyl-6-(2-methyl-5-pyrrolidin-1-yl-2H-[1,2,4]triazol-3-ylethynyl)imidazo[1,2-b]pyridazin-3-yl]-methanol The title compound was obtained by reacting (6-chloro-2-methyl-imidazo[1,2-b]pyridazin-3-yl)-methanol and 5-ethynyl-1-methyl-3-pyrrolidin-1-yl-1H-[1,2,4]triazole (described in step 2 of example 12) following the procedure described in step 4 of example 4.
MS: M=338.5 $(M+H)^+$ Step 5: (2-Methyl-6-(2-(1-methyl-3-(pyrrolidin-1-yl)-1H-1,2,4-triazol-5-yl)ethyl)imidazo[1,2-b]pyridazin-3-yl)methanol Following the procedure described in example 6, the title compound was obtained as light brown solid.
MS: M=342.6 $(M+H)^+$ Example 22

N,N,6,7-Tetramethyl-2-(2-(1-methyl-3-(pyrrolidin-1-yl)-1H-1,2,4-triazol-5-yl)ethyl)-imidazo[1,2-f][1,2,4]triazin-4-amine

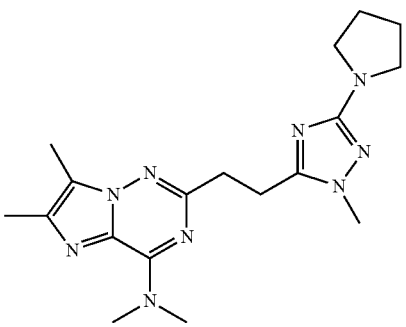 [SMILES: Cc1nc2c(N(C)C)nc(CCc3nc(N4CCCC4)nn3C)nn2c1C]

To a solution of 4-chloro-6,7-dimethyl-2-(2-(1-methyl-3-(pyrrolidin-1-yl)-1H-1,2,4-triazol-5-yl)ethyl)-imidazo[1,2-f][1,2,4]triazine (described in example 20; 40 mg, 111 μmol)

in MeOH (2 ml) at r.t under Ar was added dimethylamine in methanol (2M, 83.1 µl, 166 µmol). The mixture was stirred at 50° for 90 min. The solvent was evaporated. The crude product was purified by silica gel chromatography using a chromatography using a CH$_2$Cl$_2$/MeOH gradient as eluent, to provide the title compound (36 mg, 88%) as white solid.

MS: M=370.1 (M+H)$^+$

Example 23

3-Methyl-6-((1-methyl-3-(pyrrolidin-1-yl)-1H-1,2,4-triazol-5-yl)methoxy)-2-(trifluoro-methyl)imidazo[1,2-b]pyridazine

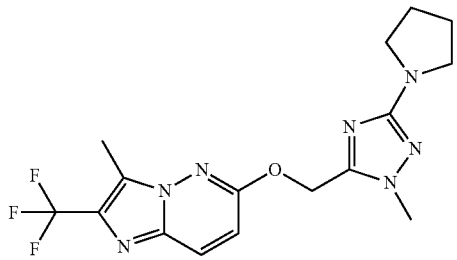 [SMILES: Cc1c(C(F)(F)F)nc2ccc(OCc3nc(N4CCCC4)nn3C)nn12]

To a suspension at 00 of NaH 60% (23.0 mg, 576 µmol) in DMF (2 ml) was added under an argon atmosphere (1-methyl-3-(pyrrolidin-1-yl)-1H-1,2,4-triazol-5-yl)methanol (described in step 3 of example 9; 70 mg, 384 µmol) and 6-chloro-3-methyl-2-(trifluoromethyl)imidazo[1,2-b]pyridazine (obtained as described in step 1 of example 1, starting with 6-chloropyridazin-3-amine; 90.5 mg, 384 µmol). The mixture was stirred at 00 for 2 hr. At 00 water was given dropwise to the reaction mixture. The product was extracted with AcOEt, washed with water, dried over MgSO$_4$, filtered and evaporated. The crude product was purified by silica gel chromatography using a chromatography using a CH$_2$Cl$_2$/MeOH gradient as eluent, to provide the title compound (115 mg, 79%) as light yellow solid.

MS: M=382.5 (M+H)$^+$

Example 24

2,3-Dimethyl-6-(2-(1-methyl-3-(pyrrolidin-1-yl)-1H-1,2,4-triazol-5-yl)ethyl)-7,8,9,10-tetrahydroimidazo[2,1-a]phthalazine

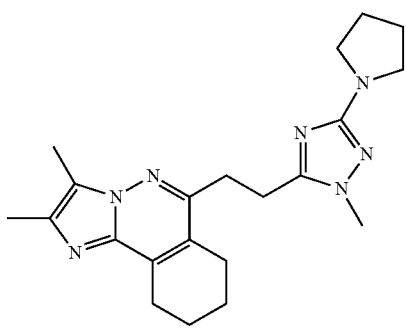 [SMILES: Cc1nc2c3c(c(CCc4nc(N5CCCC5)nn4C)nn2c1C)CCCC3]

Step 1: 4-Chloro-5,6,7,8-tetrahydrophthalazin-1-amine

A solution of 1,4-dichloro-5,6,7,8-tetrahydro-phthalazine (CAS 67279-24-7; 348 mg, 1.7 mmol) in concentrated aqueous NH$_3$ (5 ml) and ethanol (5 ml) was stirred at 120° C. in an autoclave for 20 h. The mixture was cooled to r.t. and concentrated. The crude product was purified by silica gel chromatography using a chromatography using a CH$_2$Cl$_2$/MeOH gradient as eluent, to provide the title compound (52 mg, 16%) as off-white solid.

MS: M=184.2 (M+H)$^+$

Step 2: 2,3-Dimethyl-6-(2-(1-methyl-3-(pyrrolidin-1-yl)-1H-1,2,4-triazol-5-yl)ethyl)-7,8,9,10-tetrahydroimidazo[2,1-a]phthalazine The title compound was obtained in analogy to the methods described in example 12. Off-white solid.

MS: M=380.6 (M+H)$^+$

Example 25

8-Isopropoxy-2,3-dimethyl-6-((1-methyl-3-(pyrrolidin-1-yl)-1H-1,2,4-triazol-5-yl)ethynyl)imidazo[1,2-b]pyridazine

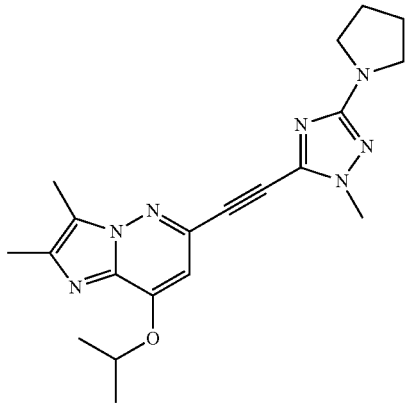 [SMILES: Cc1nc2c(OC(C)C)cc(C#Cc3nc(N4CCCC4)nn3C)nn2c1C]

Step 1: 6-Chloro-4-isopropoxypyridazin-3-amine

To a stirred solution of 4-bromo-6-chloropyridazin-3-amine (3 g, 14.4 mmol) at r.t. in THF under an argon atmosphere was added dropwise sodium isopropoxide 20% solution in THF (11.8 g, 13.1 ml, 28.8 mmol). The mixture (dark slurry) was heated to 90° C. and stirred overnight. The mixture was concentrated and the crude product was purified by silica gel chromatography using a chromatography using a CH$_2$Cl$_2$/MeOH gradient as eluent, to provide the title compound (633 mg, 61%) as off-white solid.

MS: M=188.1 (M+H)$^+$

Step 2: 8-Isopropoxy-2,3-dimethyl-6-((1-methyl-3-(pyrrolidin-1-yl)-1H-1,2,4-triazol-5-yl)ethynyl)imidazo[1,2-b]pyridazine In analogy to the procedures described in steps 1-3 of example 12, the title compound was obtained as an off-white solid.

MS: M=380.6 (M+H)$^+$

Example 26

(E)-8-Isopropoxy-2,3-dimethyl-6-(2-(1-methyl-3-(pyrrolidin-1-yl)-1H-1,2,4-triazol-5-yl)vinyl)imidazo[1,2-b]pyridazine

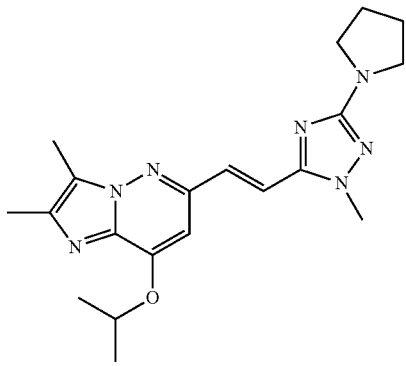 [SMILES: Cc1nc2c(OC(C)C)cc(/C=C/c3nc(N4CCCC4)nn3C)nn2c1C]

Step 1: 6-Chloro-8-isopropoxy-2,3-dimethylimidazo[1,2-b]pyridazine

The title compound was obtained from 6-chloro-4-isopropoxypyridazin-3-amine in analogy to the procedure described in step 1 of example 12. Off-white solid.
MS: M=240.2 (M+H)$^+$

Step 2: 8-Isopropoxy-2,3-dimethylimidazo[1,2-b]pyridazine-6-carbaldehyde

Following the procedures described in steps 2 and 3 of example 1, the title compound was obtained as off-white solid.
MS: M=234.2 (M+H)$^+$

Step 3: (E)-8-Isopropoxy-2,3-dimethyl-6-(2-(1-methyl-3-(pyrrolidin-1-yl)-1H-1,2,4-triazol-5-yl)vinyl)imidazo[1,2-b]pyridazine In analogy to the procedure described in step 8 of example 1, 8-isopropoxy-2,3-dimethylimidazo[1,2-b]pyridazine-6-carbaldehyde was reacted with ((1-methyl-3-(pyrrolidin-1-yl)-1H-1,2,4-triazol-5-yl)methyl)triphenylphosphonium (described in step 5 of example 9) chloride to provide the title compound. Yellow solid.
MS: M=382.6 (M+H)$^+$

Example 27

8-Isopropoxy-2,3-dimethyl-6-(2-(1-methyl-3-(pyrrolidin-1-yl)-1H-1,2,4-triazol-5-yl)ethyl)imidazo[1,2-b]pyridazine

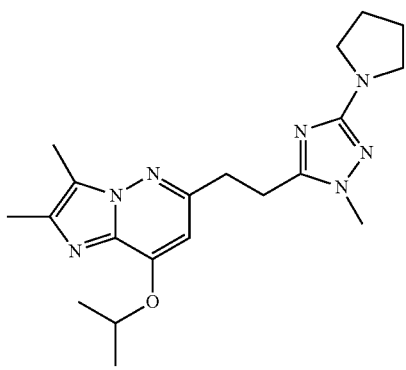 [SMILES: Cc1nc2c(OC(C)C)cc(CCc3nc(N4CCCC4)nn3C)nn2c1C]

The title compound was obtained from (E)-8-isopropoxy-2,3-dimethyl-6-(2-(1-methyl-3-(pyrrolidin-1-yl)-1H-1,2,4-triazol-5-yl)vinyl)imidazo[1,2-b]pyridazine in analogy to the procedure described in step 9 of example 1. White solid.
MS: M=384.6 (M+H)$^+$

Example 28

2,3-Dimethyl-6-((1-methyl-3-(pyrrolidin-1-yl)-1H-1,2,4-triazol-5-yl)methylthio)-imidazo[1,2-b]pyridazine

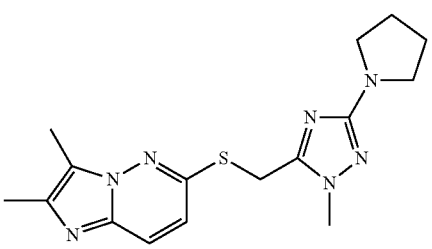 [SMILES: Cc1nc2ccc(SCc3nc(N4CCCC4)nn3C)nn2c1C]

Step 1: (1-Methyl-3-(pyrrolidin-1-yl)-1H-1,2,4-triazol-5-yl)methanethiol

A mixture of 5-(chloromethyl)-1-methyl-3-(pyrrolidin-1-yl)-1H-1,2,4-triazole (described in step 5 of example 9; 0.1 g, 498 μmol) and thiourea (37.9 mg, 498 μmol) in ethanol (3 ml) was stirred at r.t under an argon atmosphere for 2 hrs and then refluxed overnight. The solvent was evaporated. The solid was taken up in diethylether, filtered and washed with diethylether. The solid was dissolved in 1.7 ml NaOH 5%, filtered. The filtrate was acidified with 2 N HCl. The aqueous phase (pH 1) was extracted with CH$_2$Cl$_2$. The combined organics were dried over MgSO$_4$, filtered and evaporated to leave the title compound (68 mg, 69%) as almost colorless oil.
MS: M=199.2 (M+H)$^+$

Step 2: 6-Chloro-2,3-dimethylimidazo[1,2-b]pyridazine

The title compound was obtained form 6-chloropyridazin-3-amine and 3-bromobutan-2-one, following the procedure described in step 1 of example 1. Light yellow solid.
MS: M=182.1 (M+H)$^+$

Step 3: 2,3-Dimethyl-6-((1-methyl-3-(pyrrolidin-1-yl)-1H-1,2,4-triazol-5-yl)methylthio)imidazo[1,2-b]pyridazine To a solution of (1-methyl-3-(pyrrolidin-1-yl)-1H-1,2,4-triazol-5-yl)methanethiol (65 mg, 328 μmol) and 6-chloro-2,3-dimethylimidazo[1,2-b]pyridazine (59.5 mg, 328 μmol) in DMF (2 ml) was added at 0° C. and under an argon atmosphere NaH 60% (60%; 19.7 mg, 492 μmol). The mixture was stirred at 00 for 2 hrs, then water was added dropwise to the reaction mixture while maintaining the temperature at 0° C. The product was extracted with AcOEt, washed with water, dried over MgSO$_4$, filtered and evaporated. The crude product was purified by silica gel chromatography using a CH$_2$Cl$_2$/MeOH gradient as eluent, to provide the title compound (35 mg, 31%) as white solid.
MS: M=344.6 (M+H)$^+$

Example 29

2,3-Dimethyl-6-((1-methyl-3-(pyrrolidin-1-yl)-1H-1,2,4-triazol-5-yl)ethynyl)-8-(methylsulfonyl)imidazo[1,2-b]pyridazine

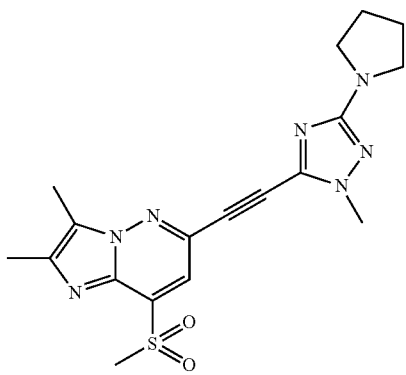 [SMILES: Cc1nc2c(S(C)(=O)=O)cc(C#Cc3nc(N4CCCC4)nn3C)nn2c1C]

Step 1: 6-Chloro-4-(methylthio)pyridazin-3-amine

To a stirred suspension of sodium methanethiolate (2.02 g, 28.8 mmol) at r.t. in dioxane (100 ml) under an argon atmosphere was added 4-bromo-6-chloropyridazin-3-amine (5 g, 24.0 mmol). The dark brown reaction mixture was heated to 100° C. over night. The dark brown slurry was cooled to r.t. and concentrated. The crude product was purified by silica gel chromatography using a $CH_2Cl_2$/MeOH gradient as eluent. The product-containing fraction were concentrated to leave a brown residue which was triturated with diethylether/MeOH 5:1 (30 ml). The solid was collected by filtration, providing the title compound (1.57 g, 37%) as off-white solid.
MS: M=176.1 (M+H)$^+$

Step 2: 6-Chloro-2,3-dimethyl-8-(methylthio)imidazo[1,2-b]pyridazine

The title compound was obtained in analogy to the procedure described in step 1 of example 12. Off-white solid.
MS: M=228.1 (M+H)$^+$

Step 3: 6-Chloro-2,3-dimethyl-8-(methylsulfonyl)imidazo[1,2-b]pyridazine

To a stirred solution of 6-chloro-2,3-dimethyl-8-(methylthio)imidazo[1,2-b]pyridazine (150 mg, 659 µmol) at r.t. in dichloromethane (5 ml) under an argon atmosphere was added 3-chlorobenzoperoxoic acid (341 mg, 1.38 mmol) in one portion. The reaction mixture was stirred at r.t. overnight, then diluted with $CH_2Cl_2$, washed with 10% $Na_2CO_3$ (2×10 ml) and brine (10 ml), dried over $MgSO_4$, filtered and concentrated. The crude product was purified by silica gel chromatography using a n-heptane/EtOAc gradient to provide the title compound (103 mg, 58%) as yellow solid.
MS: M=260.1 (M+H)$^+$

Step 4: 2,3-Dimethyl-6-((1-methyl-3-(pyrrolidin-1-yl)-1H-1,2,4-triazol-5-yl)ethynyl)-8-(methylsulfonyl)-imidazo[1,2-b]pyridazine To a stirred solution of 6-chloro-2,3-dimethyl-8-(methylsulfonyl)imidazo[1,2-b]pyridazine (310 mg, 1.19 mmol) and 5-ethynyl-1-methyl-3-(pyrrolidin-1-yl)-1H-1,2,4-triazole (described in step 2 of example 12; 252 mg, 1.43 mmol) at r.t. in DMF (5 ml) under an argon atmosphere were added triethylamine (242 mg, 331 µl, 2.39 mmol), copper(I) iodide (11.4 mg, 59.7 µmol) and bis(triphenylphosphine)palladium (II) chloride (41.9 mg, 59.7 µmol). The mixture was degassed and back-filled with argon before it was heated to 80° C. for 4 hrs. Then, the mixture was cooled to r.t., whereby a precipitate formed. The mixture was diluted with EtOAc (25 ml). The yellow solid was collected by filtration and washed with EtOAc. This crude product was by silica gel chromatography using a $CH_2Cl_2$/MeOH gradient as eluent, to obtain the title compound (201 mg, 41%) as yellow solid.
MS: M=400.5 (M+H)$^+$

Example 30

2,3-Dimethyl-6-((1-methyl-3-(pyrrolidin-1-yl)-1H-1,2,4-triazol-5-yl)methoxy)imidazo[1,2-b]pyridazine

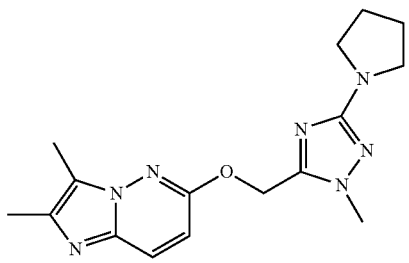 [SMILES: Cc1nc2ccc(OCc3nc(N4CCCC4)nn3C)nn2c1C]

Starting from 6-chloro-2,3-dimethylimidazo[1,2-b]pyridazine (step 2, example 28), the title compound was obtained in analogy to the procedure described in example 23. White solid.
MS: M=328.5 (M+H)$^+$

Example 31

N-Isopropyl-6,7-dimethyl-2-(2-(1-methyl-3-(pyrrolidin-1-yl)-1H-1,2,4-triazol-5-yl)ethyl)imidazo[1,2-f][1,2,4]triazin-4-amine

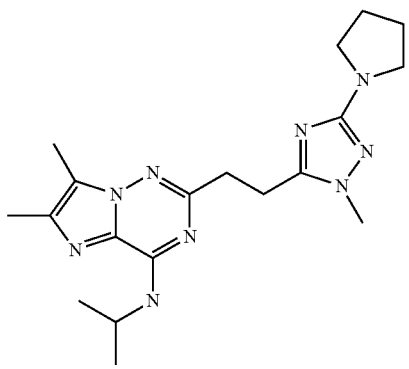 [SMILES: Cc1nc2c(NC(C)C)nc(CCc3nc(N4CCCC4)nn3C)nn2c1C]

To a solution of 4-chloro-6,7-dimethyl-2-(2-(1-methyl-3-(pyrrolidin-1-yl)-1H-1,2,4-triazol-5-yl)ethyl)-imidazo[1,2-f][1,2,4]triazine (described in example 15; 30 mg, 83 µmol) in tetrahydrofuran (1 ml) at r.t under Ar was added propan- 2-amine (7.4 mg, 10.6 μl, 125 μmol). The mixture was stirred at 50° for 90 min, then concentrated. This crude product was purified by silica gel chromatography using a CH$_2$Cl$_2$/MeOH gradient as eluent, to obtain the title compound (26 mg, 81%) as white solid.

MS: M=384.6 (M+H)

Example 32

N-Ethyl-6,7-dimethyl-2-(2-(1-methyl-3-(pyrrolidin-1-yl)-1H-1,2,4-triazol-5-yl)ethyl)-imidazo[1,2-f][1,2,4]triazin-4-amine

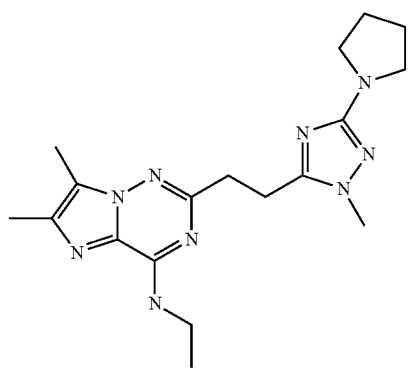 [SMILES: CCNc1nc(CCc2nc(N3CCCC3)nn2C)nn2c(C)c(C)nc12]

The title compound was obtained in analogy to the procedure described in example 31. White solid.

MS: M=384.6 (M+H)

Example 33

2,3-Dimethyl-6-(2-(1-methyl-3-(pyrrolidin-1-yl)-1H-1,2,4-triazol-5-yl)ethyl)-8-(methyl-sulfonyl)imidazo[1,2-b]pyridazine

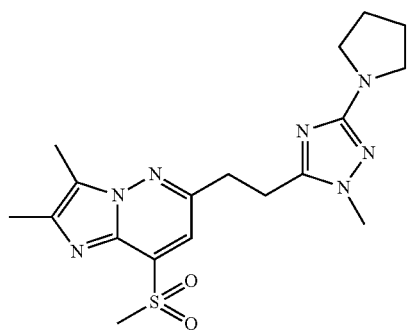 [SMILES: Cc1nc2c(S(C)(=O)=O)cc(CCc3nc(N4CCCC4)nn3C)nn2c1C]

The title compound was obtained from 2,3-dimethyl-6-((1-methyl-3-(pyrrolidin-1-yl)-1H-1,2,4-triazol-5-yl)ethynyl)-8-(methylsulfonyl)imidazo[1,2-b]pyridazine (example 29) following the procedure described in example 6. Light yellow solid.

MS: M=404.5 (M+H)$^+$

Example 34

N-Ethyl-N,6,7-trimethyl-2-(2-(1-methyl-3-(pyrrolidin-1-yl)-1H-1,2,4-triazol-5-yl)ethyl)imidazo[1,2-f][1,2,4]triazin-4-amine

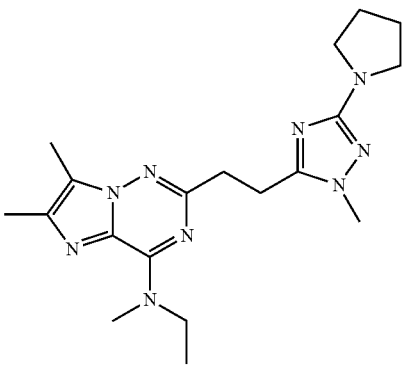 [SMILES: CCN(C)c1nc(CCc2nc(N3CCCC3)nn2C)nn2c(C)c(C)nc12]

The title compound was obtained in analogy to the procedure described in example 31. White solid.

MS: M=370.6 (M+H)$^+$

Example 35

N,N-Diethyl-6,7-dimethyl-2-(2-(1-methyl-3-(pyrrolidin-1-yl)-1H-1,2,4-triazol-5-yl)ethyl)imidazo[1,2-f][1,2,4]triazin-4-amine

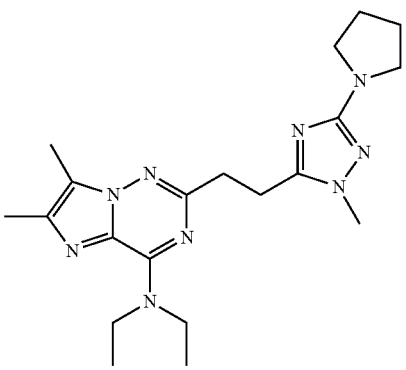 [SMILES: CCN(CC)c1nc(CCc2nc(N3CCCC3)nn2C)nn2c(C)c(C)nc12]

The title compound was obtained in analogy to the procedure described in example 31. White solid.

MS: M=398.7 (M+H)$^+$

Example 36

2-Chloro-6-((1-methyl-3-(pyrrolidin-1-yl)-1H-1,2,4-triazol-5-yl)ethynyl)imidazo[1,2-b]pyridazine

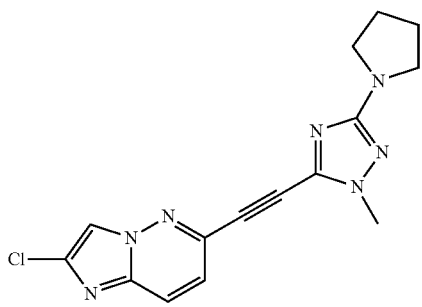 [SMILES: Cn1nc(N2CCCC2)nc1C#Cc1ccc2nc(Cl)cn2n1]

Step 1: 2,6-Dichloroimidazo[1,2-b]pyridazine

To a mixture of 6-chloropyridazin-3-amine (1 g, 7.7 mmol), ethanol (10 ml) and water (10 ml) were added triethylamine (781 mg, 1.08 ml, 7.7 mmol) and 2-chloroacetic acid (729 mg, 7.7 mmol) at r.t under an argon atmosphere. The mixture was heated at 800 for 24 hrs. The reaction mixture was evaporated to dryness. The resulting solid was mixed with phosphoryl trichloride (20.8 g, 12.7 ml, 136 mmol) and the mixture was heated at 1200 under an argon atmosphere overnight. Phosphoryl trichloride was evaporated. The residue was quenched with ice/water. The pH was adjusted to 10 with NaOH 4 N and the product was extracted with EtOAc, dried over MgSO4, filtered and evaporated. The crude product was purified by silica gel chromatography using a n-heptane/EtOAc gradient as eluent, to obtain the title compound (296 mg, 20%) as light yellow solid.
MS: M=188.1 (M+H)+

Step 2: 2-Chloro-6-((1-methyl-3-(pyrrolidin-1-yl)-1H-1,2,4-triazol-5-yl)ethynyl)imidazo[1,2-b]pyridazine The title compound was obtained in analogy to the procedure described in step 3 of example 12. Light yellow solid.
MS: M=328.1 (M+H)+

Example 37

2-Chloro-6-(2-(1-methyl-3-(pyrrolidin-1-yl)-1H-1,2,4-triazol-5-yl)ethyl)imidazo[1,2-b]pyridazine

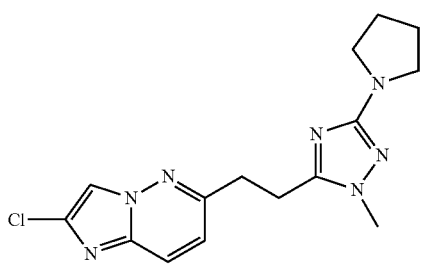 [SMILES: Cn1nc(N2CCCC2)nc1CCc1ccc2nc(Cl)cn2n1]

A solution of 2-chloro-6-((1-methyl-3-(pyrrolidin-1-yl)-1H-1,2,4-triazol-5-yl)ethynyl)imidazo[1,2-b]pyri-dazine (example 36; 30 mg, 91.5 µmol) was hydrogenated in the presence of Pd/C 10% (9.7 mg, 9.2 µmol) in ethanol (5 ml) at r.t for 1 hr. The catalyst was filtered and washed with EtOH. The solvent was evaporated. The crude product was purified by silica gel chromatography using a CH2Cl2/MeOH gradient as eluent, to obtain the title compound (23 mg, 74%) as white solid.
MS: M=332.5 (M+H)+

Example 38

2-Chloro-3-methyl-6-((1-methyl-3-(pyrrolidin-1-yl)-1H-1,2,4-triazol-5-yl)ethynyl)-imidazo[1,2-b]pyridazine

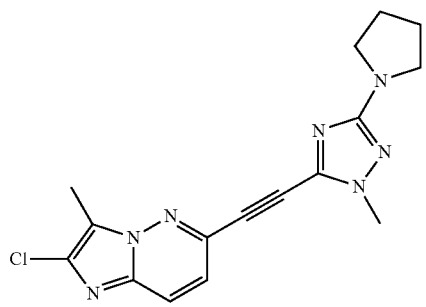 [SMILES: Cc1c(Cl)nc2ccc(C#Cc3nc(N4CCCC4)nn3C)nn12]

Step 1: 2,6-Dichloro-3-methylimidazo[1,2-b]pyridazine

To a mixture of 2-chloropropanoic acid (838 mg, 665 µl, 7.7 mmol), triethylamine (781 mg, 1.08 ml, 7.7 mmol), ethanol (10 ml) and water (10 ml) was added 6-chloropyridazin-3-amine (1 g, 7.7 mmol) at r.t under an argon atmosphere. The mixture was heated at 800 overnight, then evaporated to dryness. The resulting solid was mixed with phosphoryl trichloride (20.8 g, 12.7 ml, 136 mmol), and the mixture was heated to 1200 under argon overnight. Phosphoryl trichloride was evaporated. The residue was quenched with ice/water. The pH was adjusted to 10 with NaOH 4 N and the product was extracted with EtOAc, dried over MgSO4, filtered and evaporated. The crude product was purified by silica gel chromatography using a n-heptane/EtOAc gradient as eluent, to obtain the title compound (26 mg, 2%) as yellow solid.
MS: M=202.1 (M+H)+

Step 2: 2-Chloro-3-methyl-6-((1-methyl-3-(pyrrolidin-1-yl)-1H-1,2,4-triazol-5-yl)ethynyl)imidazo[1,2-b]pyridazine The title compound was obtained according to the procedure described in step 3 of example 12. Yellow solid.
MS: M=342.5 (M+H)+

Example 39

N,2,3-Trimethyl-6-((1-methyl-3-(pyrrolidin-1-yl)-1H-1,2,4-triazol-5-yl)ethynyl)imidazo[1,2-b]pyridazine-7-carboxamide

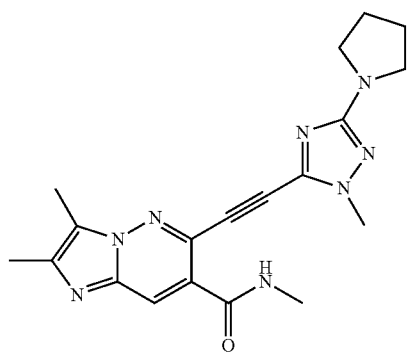 [SMILES: CNC(=O)c1cc2nc(C)c(C)n2nc1C#Cc1nc(N2CCCC2)nn1C]

Step 1: 3,6-Dichloro-N-methylpyridazine-4-carboxamide

To a stirred, cooled (0° C.) suspension of 3,6-dichloropyridazine-4-carboxylic acid (2.57 g, 13.3 mmol) in dichloromethane (30 ml) under an argon atmosphere was added carefully oxalyl chloride (1.86 g, 1.26 ml, 14.6 mmol) followed by DMF (2 drops). The reaction mixture was stirred at r.t. overnight, then concentrated.

To a stirred, cooled (0° C.) solution of the crude acid chloride (2.81 g, 13.3 mmol) in dichloromethane (40 ml) under an argon atmosphere were added methylamine hydrochloride (1.8 g, 26.6 mmol) (in one portion) and triethylamine (2.7 g, 3.7 ml, 26.6 mmol). The dark brown mixture was then stirred at r.t. for 24 hrs. The insoluble material (small amount) was filtered off and washed with CH$_2$Cl$_2$. The dark brown filtrate was concentrated. The crude product was purified by silica gel chromatography using a CH$_2$Cl$_2$/MeOH gradient as eluent, to obtain the title compound (1.5 g, 55%) as light brown solid.

MS: M=342.5 (M−H)$^-$

Step 2: 3-Amino-6-chloro-N-methylpyridazine-4-carboxamide & 6-amino-3-chloro-N-methylpyridazine-4-carboxamide A stirred solution of 3,6-dichloro-N-methylpyridazine-4-carboxamide (1.49 g, 7.23 mmol) in ethanol (8 ml) and conc. NH4OH (8 ml) was heated at 120° C. in an autoclave overnight. The mixture was cooled to r.t. and concentrated. The residue was chromatographed. The crude product was purified by silica gel chromatography using a CH$_2$Cl$_2$/MeOH gradient as eluent, to obtain 3-amino-6-chloro-N-methylpyridazine-4-carboxamide (486 mg, 36%) as light yellow solid and 6-amino-3-chloro-N-methylpyridazine-4-carboxamide (203 mg, 15%) as off-white solid.

Step 3: N,2,3-Trimethyl-6-((1-methyl-3-(pyrrolidin-1-yl)-1H-1,2,4-triazol-5-yl)ethynyl)imidazo-[1,2-b]pyridazine-7-carboxamide Following the procedures described in steps 1-3 of example 12, the title compound was obtained from 6-amino-3-chloro-N-methylpyridazine-4-carboxamide. Solid.

MS: M=379.6 (M+H)$^+$

Example 40

N,2,3-Trimethyl-6-((1-methyl-3-(pyrrolidin-1-yl)-1H-1,2,4-triazol-5-yl)ethynyl)imidazo-[1,2-b]pyridazine-8-carboxamide

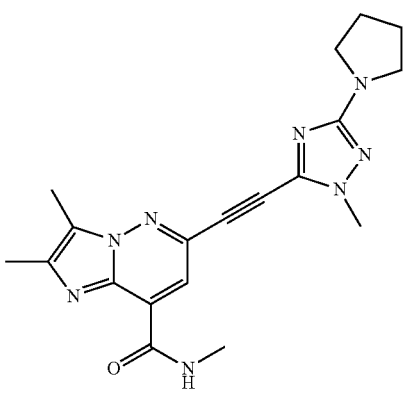 [SMILES: CNC(=O)c1cc(C#Cc2nc(N3CCCC3)nn2C)nn2c(C)c(C)nc12]

In analogy to the procedures described in step 3 of example 40, the title compound was obtained from 3-amino-6-chloro-N-methylpyridazine-4-carboxamide. Yellow solid.

MS: M=379.6 (M+H)$^+$

Example 41

N,2,3-Trimethyl-6-(2-(1-methyl-3-(pyrrolidin-1-yl)-1H-1,2,4-triazol-5-yl)ethyl)imidazo-[1,2-b]pyridazine-8-carboxamide

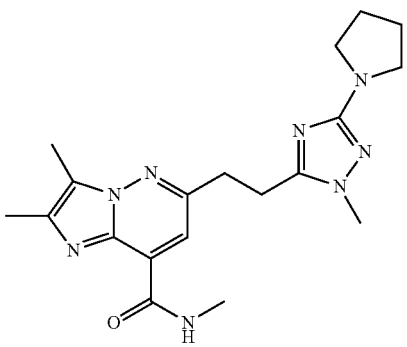 [SMILES: CNC(=O)c1cc(CCc2nc(N3CCCC3)nn2C)nn2c(C)c(C)nc12]

The title compound was obtained from N,2,3-trimethyl-6-((1-methyl-3-(pyrrolidin-1-yl)1H-1,2,4-triazol-5-yl)ethynyl)imidazo-[1,2-b]pyridazine-8-carboxamide in analogy to the method described in example 6. Yellow solid.

MS: M=383.6 (M+H)$^+$

Example 42

2,3-Dimethyl-6-((1-methyl-3-(pyrrolidin-1-yl)-1H-1,2,4-triazol-5-yl)ethynyl)-7-(trifluoro-methyl)imidazo[1,2-b]pyridazine

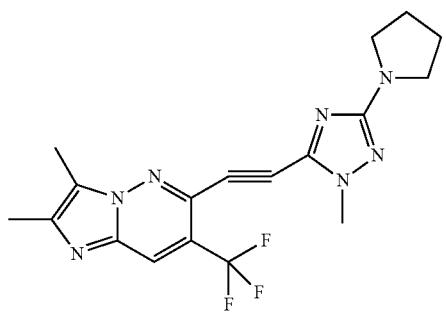 [SMILES: Cc1nc2cc(C(F)(F)F)c(C#Cc3nc(N4CCCC4)nn3C)nn2c1C]

Step 1: tert-Butyl 6-chloro-4-(trifluoromethyl)pyridazin-3-ylcarbamate

A mixture of 3,6-dichloro-4-(trifluoromethyl)pyridazine (2 g, 9.2 mmol), tert-butyl carbamate (1.4 g, 12.0 mmol) and cesium carbonate (4.2 g, 12.9 mmol) were mixed together at r.t. in dioxane (80 ml) was repeatedly (3×) evacuated followed by argon flushing. After addition of palladium (II) acetate (145 mg, 645 μmol) the procedure was again repeated 3×. After addition Xantphos (800 mg, 1.38 mmol) was added, the mixture was heated to 100° C. overnight, then cooled to r.t., diluted with EtOAc and filtered. The filtrate was concentrated. The crude product was purified by silica gel chromatography using a heptane/EtOAc gradient as eluent, to provide the title compound (1.59 g, 58%) as yellow solid.
MS: M=296.2 (M+H)$^+$

Step 2: 6-Chloro-4-(trifluoromethyl)pyridazin-3-amine

To a solution of tert-butyl 6-chloro-4-(trifluoromethyl)pyridazin-3-ylcarbamate (1.59 g, 5.34 mmol) in dioxane (20 ml) was added at r.t. under an argon atmosphere HCl in dioxane 4 M (134 ml, 534 mmol). The mixture was stirred at r.t overnight. The solvent was evaporated. The residue was triturated with diethylether, filtered, washed with diethylether and dried to provide the title compound (1.1 g, 104%) as light yellow solid.
MS: M=198.2 (M+H)$^+$

Step 3: 6-Chloro-2,3-dimethyl-8-(trifluoromethyl)imidazo[1,2-b]pyridazine

A mixture of 6-chloro-4-(trifluoromethyl)pyridazin-3-amine (0.15 g, 759 μmol), 3-bromobutan-2-one (172 mg, 120 μl, 1.14 mmol) and sodium hydrogen carbonate (95.7 mg, 1.14 mmol) in acetonitrile (4 ml) was refluxed overnight. After cooling to r.t the mixture was filtered and washed with CH$_2$Cl$_2$. The solvents were evaporated. The crude product was purified by silica gel chromatography using a heptane/EtOAc gradient as eluent, to provide the title compound (72 mg, 38%) as yellow solid.
MS: M=250.2 (M+H)$^+$

Step 4: 2,3-Dimethyl-6-((1-methyl-3-(pyrrolidin-1-yl)-1H-1,2,4-triazol-5-yl)ethynyl)-8-(trifluoromethyl)-imidazo[1,2-b]pyridazine The title compound was obtained following the procedure described in step 3 of example 12. Yellow solid.
MS: M=350.5 (M+H)$^+$

Example 43

2,3-Dimethyl-6-(2-(1-methyl-3-(pyrrolidin-1-yl)-1H-1,2,4-triazol-5-yl)ethyl)-7-(trifluoro-methyl)imidazo[1,2-b]pyridazine

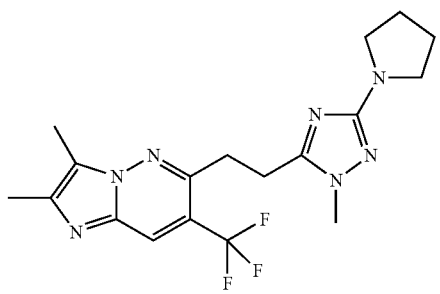 [SMILES: Cc1nc2cc(C(F)(F)F)c(CCc3nc(N4CCCC4)nn3C)nn2c1C]

The title compound was obtained in analogy to the procedure described in example 37. Light yellow solid.
MS: M=398.5 (M+H)$^+$

Example 44

8-Isopropyl-2,3-dimethyl-6-((1-methyl-3-(pyrrolidin-1-yl)-1H-1,2,4-triazol-5-yl)ethynyl)imidazo[1,2-b]pyridazine

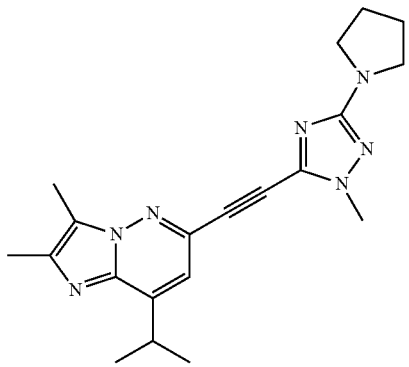 [SMILES: Cc1nc2c(C(C)C)cc(C#Cc3nc(N4CCCC4)nn3C)nn2c1C]

Step 1: 3,6-Dichloro-4-isopropyl-pyridazine

A solution of 3,6-dichloro-pyridazine (10 g, 67.6 mmol), silver nitrate (1.15 g, 6.7 mmol), methylpropanoic acid (7.8 ml, 84.5 mmol), and trifluoroacetic acid (1.0 ml, 13.5 mmol) in water (60 ml) was heated to 70° C. To this mixture was added a solution of ammonium persulfate (27.7 g, 121.6 mmol) in water (20 ml) over 20 mins. The reaction mixture was stirred for additional 20 mins, then basified (pH 9) with saturated aqueous solution of NaHCO$_3$ (15 ml) and extracted with hexane (2×50 ml). The combined organic layers were washed with water (20 ml), and brine (20 ml), dried over anhydrous Na₂SO₄, filtered, and evaporated off under reduced pressure to give 3,6-dichloro-4-isopropyl-pyridazin (10.5 g, 81.3%) as pale yellow oil.

LC-MS (ESI): 191.0 (M+H).

Step 2: 6-Chloro-4-isopropyl-pyridazin-3-ylamine & 6-chloro-5-isopropyl-pyridazin-3-ylamine A mixture of 3,6-dichloro-4-isopropyl-pyridazine (3.8 g, 19.8 mmol) in aqueous ammonium hydroxide solution (28%; 120 ml) was heated at 130° C. in a sealed tube for 16 hrs. The reaction mixture was diluted with water (100 ml), and extracted with CH₂Cl₂ (3×100 ml). The combined organics were washed with brine (100 ml), dried over anhydrous Na₂SO₄, filtered and concentrated. The crude material was purified by prep-HPLC to afford 6-chloro-4-isopropyl-pyridazin-3-ylamine (450 mg, 13%) as off white solid (LC-MS (ESI): 171.8 (M+H)) and 6-chloro-5-isopropyl-pyridazin-3-ylamine (1.25 g, 37%) as off white solid (LC-MS (ESI): 171.8 (M+H))

Step 3: 6-Chloro-8-isopropyl-2,3-dimethyl-imidazo[1,2-b]pyridazine

To a solution of 6-chloro-4-isopropyl-pyridazin-3-ylamine (450 mg, 2.6 mmol) in 1,2-dimethoxy ethane (30 ml) was added 3-bromo-butan-2-on (0.3 ml, 2.6 mmol) under argon atmosphere at 25° C. The reaction mixture was heated to reflux overnight. Volatiles were removed in vacuo. The crude material was purified by silica gel chromatography using 60% EtOAc/hexane as gradient to give the title compound (220 mg, 37%) as pale yellow solid.

LC-MS (ESI): 223.6 (M+H).

Step 2: 8-Isopropyl-2,3-dimethyl-6-((1-methyl-3-(pyrrolidin-1-yl)-1H-1,2,4-triazol-5-yl)ethynyl)imidazo[1,2-b]pyridazine The title compound was obtained in analogy to the procedure described in step 3 of example 12. Yellow solid.
MS: M=364.5 (M+H)⁺

Example 45

8-Isopropyl-2,3-dimethyl-6-(2-(1-methyl-3-(pyrrolidin-1-yl)-1H-1,2,4-triazol-5-yl)ethyl)-imidazo[1,2-b]pyridazine

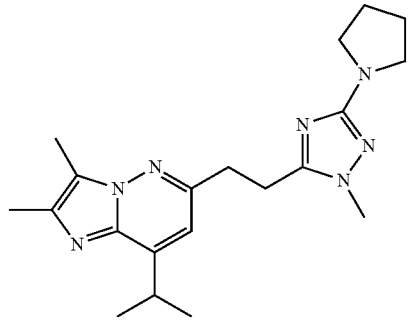 [SMILES: Cc1nc2c(C(C)C)cc(CCc3nc(N4CCCC4)nn3C)nn2c1C]

The title compound was obtained in analogy to the procedure described in example 6. Colorless amorphous solid.
MS: M=368.6 (M+H)⁺

Example 46

8-Cyclopropyl-2,3-dimethyl-6-((1-methyl-3-(pyrrolidin-1-yl)-1H-1,2,4-triazol-5-yl)ethynyl)imidazo[1,2-b]pyridazine

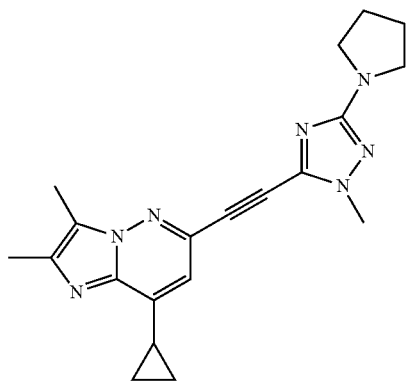 [SMILES: Cc1nc2c(C3CC3)cc(C#Cc3nc(N4CCCC4)nn3C)nn2c1C]

Step 1: 6-Chloro-8-cyclopropyl-2,3-dimethy2-imidazo[1,2-b]pyridazine

The title compound was obtained in analogy to the procedures described in steps 1-3 of example 44, using cyclopropane carboxylic acid in the 1st step. Off-white solid.
MS: M=221.8 (M+H)⁺

Step 2: 8-Cyclopropyl-2,3-dimethyl-6-((1-methyl-3-(pyrrolidin-1-yl)-1H-1,2,4-triazol-5-yl)ethynyl)imidazo-[1,2-b]pyridazine The title compound was obtained in analogy to the procedure described in step 3 of example 12. Yellow solid.
MS: M=362.6 (M+H)⁺

Example 47

8-Cyclobutyl-2,3-dimethyl-6-((1-methyl-3-(pyrrolidin-1-yl)-1H-1,2,4-triazol-5-yl)ethynyl)imidazo[1,2-b]pyridazine

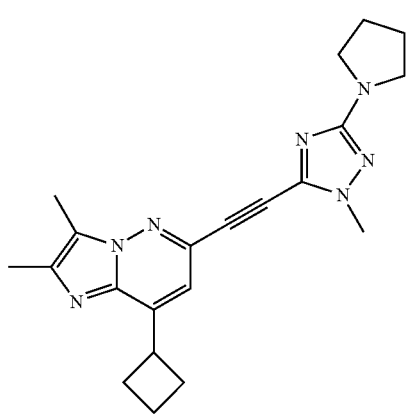 [SMILES: Cc1nc2c(C3CCC3)cc(C#Cc3nc(N4CCCC4)nn3C)nn2c1C]

Step 1: 6-Chloro-8-cyclobutyl-2,3-dimethy2-imidazo[1,2-b]pyridazine

The title compound was obtained in analogy to the procedures described in steps 1-3 of example 44, using cyclobutane carboxylic acid in the 1st step. Off-white solid.
MS: M=236.2 (M+H)+

Step 2: 8-Cyclobutyl-2,3-dimethyl-6-((1-methyl-3-(pyrrolidin-1-yl)-1H-1,2,4-triazol-5-yl)ethynyl)imidazo-[1,2-b]pyridazine The title compound was obtained in analogy to the procedure described in step 3 of example 12. Yellow solid.
MS: M=376.6 (M+H)+

Example 48

8-Cyclobutyl-2,3-dimethyl-6-(2-(1-methyl-3-(pyrrolidin-1-yl)-1H-1,2,4-triazol-5-yl)ethyl)imidazo[1,2-b]pyridazine

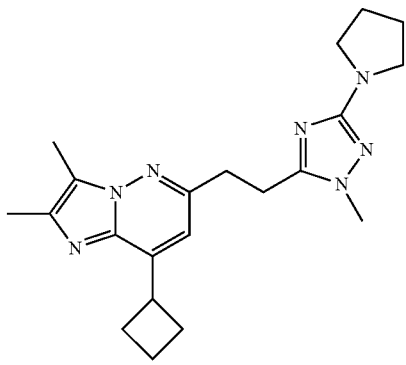 [SMILES: Cc1nc2c(C3CCC3)cc(CCc3nc(N4CCCC4)nn3C)nn2c1C]

The title compound was obtained in analogy to the procedure described in example 6. Colorless amorphous solid.
MS: M=380.6 (M+H)+

Example 49

8-Cyclopropyl-2,3-dimethyl-6-(2-(1-methyl-3-(pyrrolidin-1-yl)-1H-1,2,4-triazol-5-yl)ethyl)imidazo[1,2-b]pyridazine

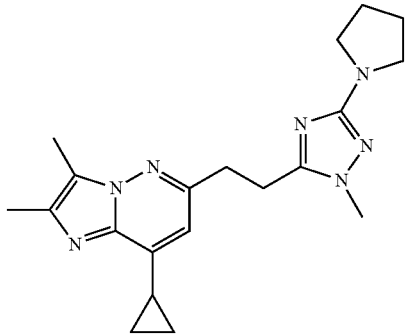 [SMILES: Cc1nc2c(C3CC3)cc(CCc3nc(N4CCCC4)nn3C)nn2c1C]

The title compound was obtained in analogy to the procedure described in example 6. Colorless amorphous solid.
MS: M=366.6 (M+H)+

Example 50

7-Isopropyl-2,3-dimethyl-6-((1-methyl-3-(pyrrolidin-1-yl)-1H-1,2,4-triazol-5-yl)ethynyl)imidazo[1,2-b]pyridazine

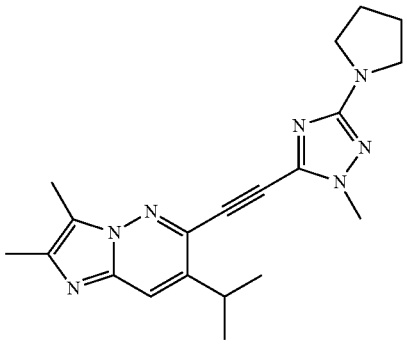 [SMILES: Cc1nc2cc(C(C)C)c(C#Cc3nc(N4CCCC4)nn3C)nn2c1C]

Step 1: 6-Chloro-8-isopropyl-2,3-dimethyl-imidazo[1,2-b]pyridazine

The title compound was obtained from 6-chloro-5-isopropyl-pyridazin-3-ylamine (described in step 2 of example 44) following the procedure described in step 3 of example 44. Off-white solid.
MS: M=224.0 (M+H)+

Step 2: 7-Isopropyl-2,3-dimethyl-6-((1-methyl-3-(pyrrolidin-1-yl)-1H-1,2,4-triazol-5-yl)ethynyl)imidazo[1,2-b]pyridazine The title compound was obtained in analogy to the procedure described in step 3 of example 12. Yellow solid.
MS: M=364.6 (M+H)+

Example 51

7-Cyclobutyl-2,3-dimethyl-6-((1-methyl-3-(pyrrolidin-1-yl)-1H-1,2,4-triazol-5-yl)ethynyl)imidazo[1,2-b]pyridazine

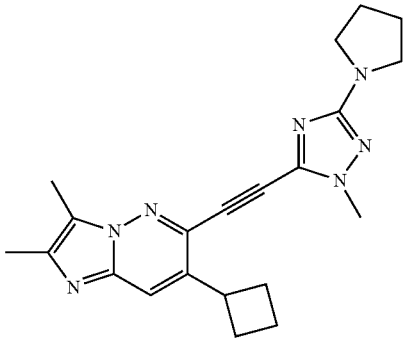 [SMILES: Cc1nc2cc(C3CCC3)c(C#Cc3nc(N4CCCC4)nn3C)nn2c1C]

The title compound was obtained in analogy to the procedures described in example 50. Yellow solid.
MS: M=376.6 (M+H)+

Example 52

2,3-Dimethyl-5-((1-methyl-3-(pyrrolidin-1-yl)-1H-1,2,4-triazol-5-yl)ethynyl)pyrazolo[1,5-a]pyrimidine

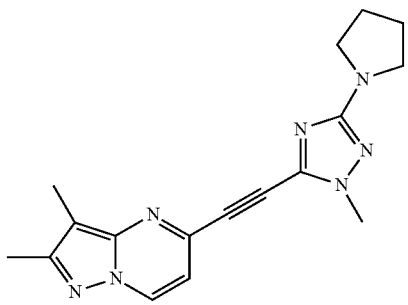 [SMILES: Cc1nn2ccc(C#Cc3nc(N4CCCC4)nn3C)nc2c1C]

Step 1:
2,3-Dimethyl-pyrazolo[1,5-a]pyrimidine-5,7-diol

A sodium ethanolate solution (21% in EtOH; 35.1 g, 40.5 ml, 108 mmol) was added to ethanol (200 ml) at r.t. under an argon atmosphere. To this were added diethyl malonate (4.34 g, 4.11 ml, 27.1 mmol) and 4,5-dimethyl-1H-pyrazol-3-amine hydrochloride (4 g, 27.1 mmol). The mixture was heated to 85° C. overnight. The mixture was cooled to r.t. and treated with aq. 5 N HCl until pH ~5 was reached. The mixture was concentrated to dryness, and the residue was used directly in the next step Step 2: 5,7-Dichloro-2,3-dimethyl-pyrazolo[1,5-a]pyrimidine A mixture of 2,3-dimethylpyrazolo[1,5-a]pyrimidine-5,7-diol (4.86 g, 27.1 mmol) and N,N-dimethylaniline (5.74 g, 6 ml, 47.3 mmol) in phosphoryl trichloride (98.7 g, 60 ml, 644 mmol) was heated to 115° C. under an argon atmosphere for 3 hrs. The brown suspension was cooled to r.t. and very carefully poured into 500 g of crushed ice. The resulting slurry was stirred at r.t. for 30 min and then extracted with CH$_2$Cl$_2$. The combined organics were washed with H$_2$O and brine, dried over MgSO$_4$, filtered and concentrated to leave the crude product as a light brown sticky solid. The crude product was purified by silica gel chromatography using an n-heptane/EtOAc gradient as eluent, providing the title compound (2.63 g, 45%) as light brown solid.
MS: M=216.1 (M+H)+

Step 3:
5-Chloro-2,3-dimethyl-pyrazolo[1,5-a]pyrimidine

To a stirred suspension of 5,7-dichloro-2,3-dimethyl-pyrazolo[1,5-a]pyrimidine (2.61 g, 12.1 mmol) at r.t. in acetic acid (50 ml) under an argon atmosphere was added zinc dust (3.16 g, 48.3 mmol) in one portion. The reaction mixture was stirred at r.t. for 2 days. The white compact slurry was concentrated to dryness to leave a light brown solid which was suspended in H$_2$O (60 ml). Then 15% aqueous KHCO$_3$ solution (50 ml) were added. The mixture was extracted with dichloromethane. The combined organics were washed with brine, dried over MgSO$_4$, filtered and concentrated. The crude product was purified by silica gel chromatography using an n-heptane/EtOAc gradient as eluent, providing the title compound (1.66 g, 76%) as yellow solid.
MS: M=182.1 (M+H)+

Step 4: 2,3-Dimethyl-5-((1-methyl-3-(pyrrolidin-1-yl)-1H-1,2,4-triazol-5-yl)ethynyl)pyrazolo[1,5-a]pyri-midine The title compound was obtained in analogy to the procedure described in step 3 of example 12. Yellow solid.
MS: M=322.5 (M+H)+

Example 53

2,3-dimethyl-5-(2-(1-methyl-3-(pyrrolidin-1-yl)-1H-1,2,4-triazol-5-yl)ethyl)pyrazolo[1,5-a]pyrimidine

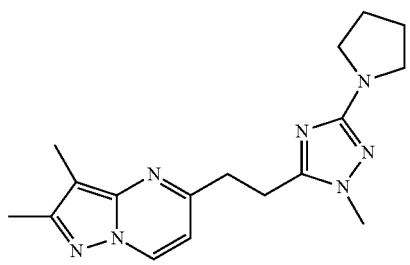 [SMILES: Cc1nn2ccc(CCc3nc(N4CCCC4)nn3C)nc2c1C]

The title compound was obtained in analogy to the procedure described in example 6. Off-white solid.
MS: M=326.5 (M+H)+

Example 54

3,8-Dimethyl-6-((1-methyl-3-(pyrrolidin-1-yl)-1H-1,2,4-triazol-5-yl)ethynyl)-2-(trifluoro-methyl)imidazo[1,2-b]pyridazine

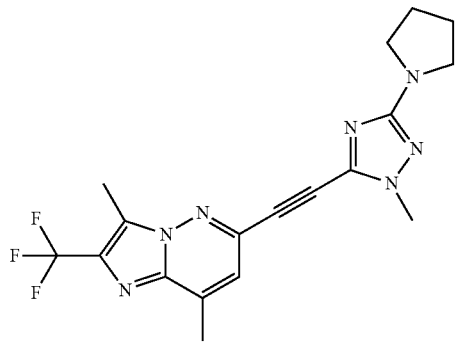 [SMILES: Cc1cc(C#Cc2nc(N3CCCC3)nn2C)nn2c(C)c(C(F)(F)F)nc12]

Step 1: 6-Chloro-3,8-dimethyl-2-(trifluoromethyl)imidazo[1,2-b]pyridazine

The title compound was obtained in analogy to the procedure in step 1 of example 1, starting from 6-chloro-4-methylpyridazin-3-amine (described in step 1 of example 16). White solid.
MS: M=250.2 (M+H)+

Step 2: 3,8-Dimethyl-6-((1-methyl-3-(pyrrolidin-1-yl)-1H-1,2,4-triazol-5-yl)ethynyl)-2-(trifluoromethyl)imidazo[1,2-b]pyridazine The title compound was obtained in analogy to the procedure described in step 3 of example 12. Yellow solid.
MS: M=390.5 (M+H)+

Example 55

3,8-Dimethyl-6-(2-(1-methyl-3-(pyrrolidin-1-yl)-1H-1,2,4-triazol-5-yl)ethyl)-2-(trifluoro-methyl)imidazo[1,2-b]pyridazine

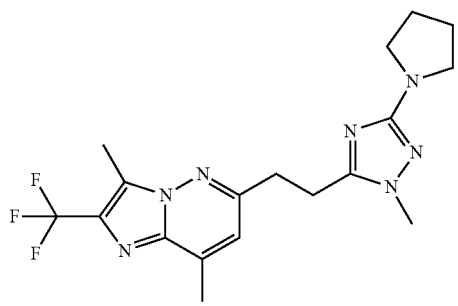 [SMILES: Cc1cc(CCc2nc(N3CCCC3)nn2C)nn2c(C)c(C(F)(F)F)nc12]

The title compound was obtained in analogy to the procedure described in example 37. White solid.
MS: M=394.6 (M+H)+

Example 56

3-Methyl-6-((1-methyl-3-(pyrrolidin-1-yl)-1H-1,2,4-triazol-5-yl)ethynyl)[1,2,4]triazolo-[4,3-b]pyridazine

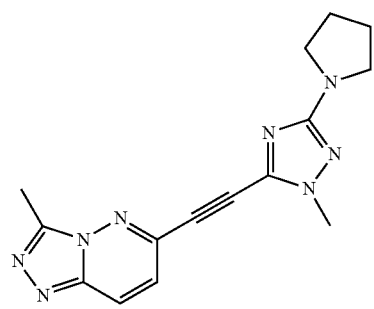 [SMILES: Cc1nnc2ccc(C#Cc3nc(N4CCCC4)nn3C)nn12]

Step 1:
6-Chloro-3-methyl-[1,2,4]triazolo[4,3-b]pyridazine

To a solution at r.t of 3,6-dichloropyridazine (1 g, 6.7 mmol) in dioxane (45 ml) was added at r.t. under an argon atmosphere acetohydrazide (1.74 g, 23.5 mmol), triethylamine (747 mg, 1.03 ml, 7.4 mmol) and p-toluenesulfonic acid monohydrate (1.4 g, 7.4 mmol). The mixture was heated at 100° for overnight. For a second time, acetohydrazide (1.74 g, 23.5 mmol), triethylamine (747 mg, 1.0 ml, 7.4 mmol) and p-toluenesulfonic acid monohydrate (1.4 g, 7.4 mmol) were added, and the mixture was stirred again at 100° overnight. Then, the solvent was removed. The residue was dissolved in CH$_2$Cl$_2$, washed with water. The organic layer was dried over MgSO$_4$, filtered and evaporated. The crude product was purified by silica gel chromatography using a CH$_2$Cl$_2$/MeOH gradient as eluent, to obtain the title compound (138 mg, 12%) as white solid.
MS: M=169.1 (M+H)+

Step 2: 3-Methyl-6-((1-methyl-3-(pyrrolidin-1-yl)-1H-1,2,4-triazol-5-yl)ethynyl)[1,2,4]triazolo-[4,3-b]pyridazine The title compound was obtained in analogy to the procedure described in step 3 of example 12. Off-white solid.
MS: M=309.5 (M+H)+

Example 57

3-Methyl-6-(2-(1-methyl-3-(pyrrolidin-1-yl)-1H-1,2,4-triazol-5-yl)ethyl)[1,2,4]triazolo[4,3-b]pyridazine

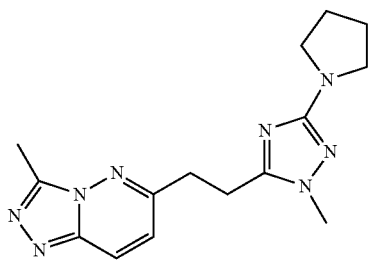 [SMILES: Cc1nnc2ccc(CCc3nc(N4CCCC4)nn3C)nn12]

The title compound was obtained in analogy to the procedure described in example 37. Yellow solid.
MS: M=313.6 (M+H)+

Example 58

7-Cyclohexyl-2,3-dimethyl-6-(2-(1-methyl-3-(pyrrolidin-1-yl)-1H-1,2,4-triazol-5-yl)ethyl)imidazo[1,2-b]pyridazine

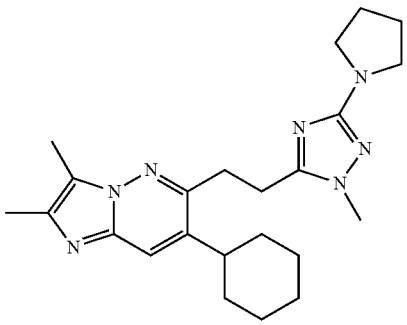 [SMILES: Cc1nc2cc(C3CCCCC3)c(CCc3nc(N4CCCC4)nn3C)nn2c1C]

Step 1: 6-Chloro-5-cyclohexylpyridazin-3-amine

In analogy to the procedure described in steps 1 and 2 of example 44, the title compound was obtained, starting from 3,6-dichloropyridazine and cyclohexane carboxylic acid, as the only regioisomer. Off-white solid.
MS: M=212.1 (M+H)+

Step 2: 5-Cyclohexyl-6-iodopyridazin-3-amine

A mixture of 6-chloro-5-cyclohexylpyridazin-3-amine (100 mg, 472 µmol) and hydroiodic acid 57% in water (1.7 g, 1 ml, 7.58 mmol) was stirred at 100° C. under an argon atmosphere for 18 hrs. The dark brown mixture was cooled to r.t., diluted with EtOAc and treated with 10% Na2CO3. The aqueous phase was back extracted with EtOAc. The combined organics were washed with H2O and brine, dried over MgSO4, filtered and concentrated. The crude product was purified by silica gel chromatography using an CH2Cl2/MeOH gradient as eluent, to provide the title compound (90 mg, 63%) as off-white solid.
MS: M=304.4 (M+H)$^+$

Step 3: 7-Cyclohexyl-6-iodo-2,3-dimethylimidazo[1,2-b]pyridazine

In analogy to the procedure described in step 1 of example 12, the title compound was obtained as off-white solid.
MS: M=356.5 (M+H)$^+$

Step 4: 7-Cyclohexyl-2,3-dimethyl-6-((1-methyl-3-(pyrrolidin-1-yl)-1H-1,2,4-triazol-5-yl)ethynyl)imidazo[1,2-b]pyridazine In analogy to the procedure described in step 3 of example 12, the title compound was obtained from 7-cyclohexyl-6-iodo-2,3-dimethylimidazo[1,2-b]pyridazine and 5-ethynyl-1-methyl-3-(pyrrolidin-1-yl)-1H-1,2,4-triazole as yellow solid.
MS: M=404.7 (M+H)$^+$

Step 5: 7-Cyclohexyl-2,3-dimethyl-6-(2-(1-methyl-3-(pyrrolidin-1-yl)-1H-1,2,4-triazol-5-yl)ethyl)imidazo[1,2-b]pyridazine The title compound was obtained in analogy to the procedure described in example 6. Light yellow solid.
MS: M=408.6 (M+H)$^+$

Example 59

2,3,6-Trimethyl-5-((1-methyl-3-(pyrrolidin-1-yl)-1H-1,2,4-triazol-5-yl)ethynyl)pyrazolo[1,5-a]pyrimidine

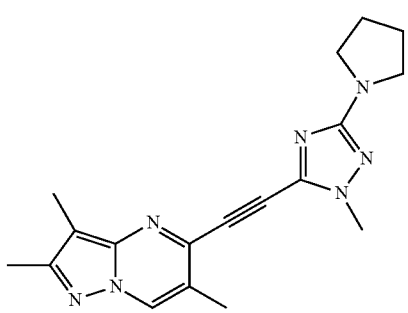 [SMILES: Cc1cn2nc(C)c(C)c2nc1C#Cc1nc(N2CCCC2)nn1C]

The title compound was obtained in analogy to the procedures described in example 53, using diethyl 2-methylmalonate in the first step. Yellow solid.
MS: M=326.5 (M+H)$^+$

Example 60

7-Methoxy-2,3-dimethyl-6-((1-methyl-3-(pyrrolidin-1-yl)-1H-1,2,4-triazol-5-yl)ethynyl)imidazo[1,2-b]pyridazine

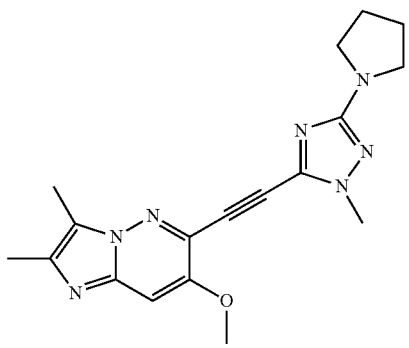 [SMILES: COc1cc2nc(C)c(C)n2nc1C#Cc1nc(N2CCCC2)nn1C]

Step 1: tert-Butyl 6-chloro-5-methoxypyridazin-3-ylcarbamate

To a stirred solution of 3,6-dichloro-4-methoxypyridazine (CAS 70952-62-4; 1.5 g, 8.38 mmol) and tert-butyl carbamate (1.28 g, 10.9 mmol) at r.t. in dioxane under an argon atmosphere were added cesium carbonate (3.82 g, 11.7 mmol), Xantphos (727 mg, 1.26 mmol) and palladium (II) acetate (132 mg, 587 µmol). The mixture was degassed and back-filled with argon before it was heated to 100° C. Stirring at that temperature was continued for 18 hrs. The mixture was cooled to r.t. and concentrated. The residual dark brown viscous oil was triturated in 50 ml of CH$_2$Cl$_2$/MeOH 9:1. The insoluble material was filtered off and washed with CH$_2$Cl$_2$. The filtrate was concentrated. The crude product was purified by silica gel chromatography using an heptane/EtOAc gradient as eluent, to provide the title compound (178 mg, 8%) as white solid.
MS: M=260.2 (M+H)$^+$

Step 2: 6-Chloro-5-methoxypyridazin-3-amine

To a stirred, cooled (0° C.) solution of tert-butyl 6-chloro-5-methoxypyridazin-3-ylcarbamate (170 mg, 655 µmol) in dichloromethane (4 ml) under an argon atmosphere was added 2,2,2-trifluoroacetic acid (1.49 g, 1.00 ml, 13.1 mmol). The ice bath was removed and stirring at r.t. was continued for 3 hrs. The mixture was carefully added to saturated aq. Na$_2$CO$_3$ solution (20 ml) which was extracted with CH$_2$Cl$_2$ and CH$_2$Cl$_2$/MeOH 95:5. The combined organics were dried over MgSO4, filtered and concentrated to leave the crude product as a light brown foam. The crude product was purified by silica gel chromatography using an CH$_2$Cl$_2$/MeOH gradient as eluent, to provide the title compound (70 mg, 67%) as off-white solid.
MS: M=160.1 (M+H)$^+$

Step 3: 6-Chloro-7-methoxy-2,3-dimethylimidazo[1,2-b]pyridazine

The title compound was obtained from 6-chloro-5-methoxypyridazin-3-amine and 3-bromobutan-2-one in analogy to the procedure described in step 1 of example 12. Light yellow solid.
MS: M=212.2 (M+H)$^+$ Step 4: 7-Methoxy-2,3-dimethyl-6-((1-methyl-3-(pyrrolidin-1-yl)-1H-1,2,4-triazol-5-yl)ethynyl)imidazo[1,2-b]pyridazine In analogy to the procedure described in step 3 of example 12, the title compound was obtained from 6-chloro-7-methoxy-2,3-dimethylimidazo[1,2-b]pyridazine and 5-ethynyl-1-methyl-3-(pyrrolidin-1-yl)-1H-1,2,4-triazole as yellow solid.
MS: M=352.5 (M+H)+

Example 61

2,3,6-Trimethyl-5-(2-(1-methyl-3-(pyrrolidin-1-yl)-1H-1,2,4-triazol-5-yl)ethyl)pyrazolo[1,5-a]pyrimidine

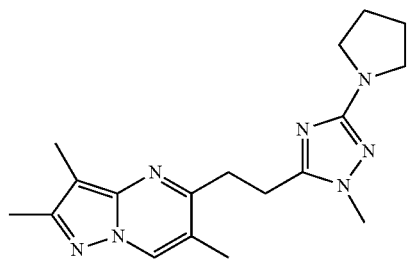 [SMILES: Cc1cn2nc(C)c(C)c2nc1CCc1nc(N2CCCC2)nn1C]

The title compound was obtained from 2,3,6-trimethyl-5-((1-methyl-3-(pyrrolidin-1-yl)-1H-1,2,4-triazol-5-yl)ethynyl)pyrazolo[1,5-a]pyrimidine (example 59) in analogy to the procedure described in example 6.
MS: M=340.5 (M+H)+

Example 62

3-Methyl-6-((1-methyl-3-(pyrrolidin-1-yl)-1H-1,2,4-triazol-5-yl)ethynyl)-8-(2,2,2-trifluoroethoxy)-2-(trifluoromethyl)imidazo[1,2-b]pyridazine

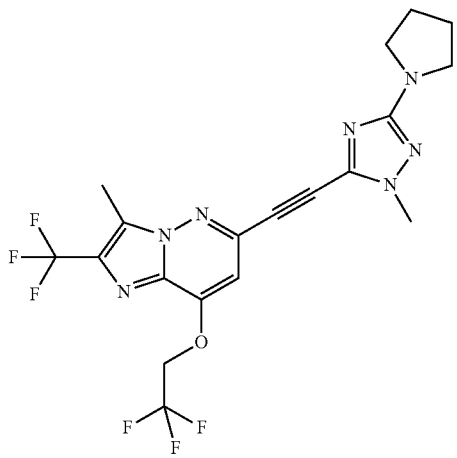 [SMILES: Cc1c(C(F)(F)F)nc2c(OCC(F)(F)F)cc(C#Cc3nc(N4CCCC4)nn3C)nn12]

Step 1: 6-Chloro-4-(2,2,2-trifluoroethoxy)pyridazin-3-amine

To a stirred, cooled (0° C.) solution of 2,2,2-trifluoroethanol (300 mg, 216 µl, 3.00 mmol) in DMF (5 ml) under an argon atmosphere was added potassium tert-butoxide (13.5 mg, 120 µmol) in one portion. Stirring at 0° C. was continued for 45 mins, then 4-bromo-6-chloropyridazin-3-amine (250 mg, 1.2 mmol) and copper(I) bromide (224 mg, 1.56 mmol) were added. The ice bath was removed. The mixture was heated to 120° C. and stirring at that temperature was continued for 4 hrs. The mixture was cooled to r.t., diluted with EtOAc and washed with H2O. The aqueous phase was back-extracted with EtOAc. The combined organics were washed with brine, dried over MgSO4, filtered and concentrated. The crude product was purified by silica gel chromatography using a CH2Cl2/MeOH gradient as eluent, providing the title compound as off-white solid.
MS: M=228.3 (M+H)+

Step 2: 3-Methyl-6-((1-methyl-3-(pyrrolidin-1-yl)-1H-1,2,4-triazol-5-yl)ethynyl)-8-(2,2,2-trifluoroethoxy)-2-(trifluoromethyl)imidazo[1,2-b]pyridazine The title compound was obtained in analogy to steps 1 and 3 of example 12. Yellow solid.
MS: M=474.4 (M+H)+

Example 63

3-Methyl-6-(2-(1-methyl-3-(pyrrolidin-1-yl)-1H-1,2,4-triazol-5-yl)ethyl)-8-(2,2,2-trifluoroethoxy)-2-(trifluoromethyl)imidazo[1,2-b]pyridazine

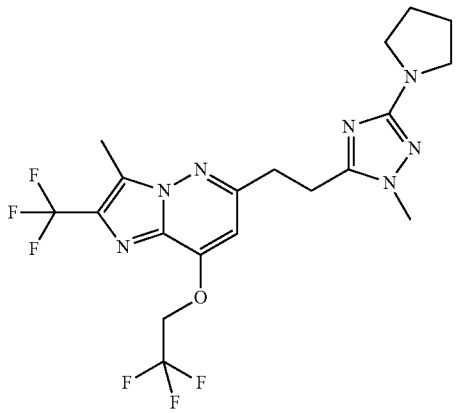 [SMILES: Cc1c(C(F)(F)F)nc2c(OCC(F)(F)F)cc(CCc3nc(N4CCCC4)nn3C)nn12]

The title compound was obtained in analogy to the procedure described in example 6. Light yellow gum.
MS: M=478.4 (M+H)+

Example 64

2-Chloro-3-methyl-6-(2-(1-methyl-3-(pyrrolidin-1-yl)-1H-1,2,4-triazol-5-yl)ethyl)imidazo[1,2-b]pyridazine

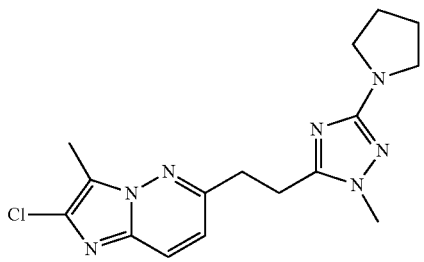 [SMILES: Cc1c(Cl)nc2ccc(CCc3nc(N4CCCC4)nn3C)nn12]

Step 1: Methyl 6-iodo-3-methylimidazo[1,2-b]pyridazine-2-carboxylate

The title compound was obtained in analogy to the procedure described in step 1 of example 3. Off-white solid.
MS: M=318.2 (M+H)+

Step 2: 6-Iodo-3-methylimidazo[1,2-b]pyridazine-2-carboxylic acid

To a solution at 00 of methyl 6-iodo-3-methylimidazo[1,2-b]pyridazine-2-carboxylate (850 mg, 2.68 mmol) in THF (40 ml) was added under an argon atmosphere a solution of LiOH monohydrate (337 mg, 8.04 mmol) in water (20 ml). The mixture was stirred at r.t overnight. The solvent was removed. The residue was diluted with 10 ml water and washed with 15 ml AcOEt. The aqueous was acidified to pH 5 with 1N HCl at 00 and extracted with $CH_2Cl_2$/MeOH 9:1. The organic layer was dried over $MgSO_4$, filtered and evaporated to obtain the title compound (700 mg, 86%) as off-white solid.
MS: M=304.2 (M+H)+

Step 3: tert-Butyl 6-iodo-3-methylimidazo[1,2-b]pyridazin-2-ylcarbamate

To a suspension of 6-iodo-3-methylimidazo[1,2-b]pyridazine-2-carboxylic acid (0.6 g, 1.98 mmol) and triethylamine (601 mg, 828 µl, 5.94 mmol) in tert-butanol (15 ml) was added at r.t. and under an argon atmosphere diphenyl phosphorazidate (817 mg, 641 µl, 2.97 mmol). The mixture was refluxed for 22 hrs. After cooling to r.t, the mixture was diluted with AcOEt, washed with a solution of citric acid 5% and saturated sodium bicarbonate. The organic phase was dried over $MgSO_4$, filtered and evaporated. The crude product was purified by silica gel chromatography using a $CH_2Cl_2$/MeOH gradient as eluent, to provide the title compound (198 mg, 27%) as off-white solid.
MS: M=375.3 (M+H)+

Step 4: 6-Iodo-3-methylimidazo[1,2-b]pyridazin-2-amine

To a solution of tert-butyl 6-iodo-3-methylimidazo[1,2-b]pyridazin-2-ylcarbamate (137 mg, 366 µmol) in dichloromethane (5 ml) was added under an argon atmosphere and at 0° C. trifluoracetic acid (250 mg, 169 µl, 2.2 mmol). The solution was stirred at 00 for 30 min and at r.t for 6 hr. The reaction mixture was cooled to 00 and basified with 1 N NaOH. The product was extracted with $CH_2Cl_2$, dried over $MgSO_4$, filtered and evaporated to obtain the title compound (113 mg, quantitative) as off-white solid.
MS: M=275.3 (M+H)+

Step 5: 2-Chloro-6-iodo-3-methylimidazo[1,2-b]pyridazine

To a suspension of 6-iodo-3-methylimidazo[1,2-b]pyridazin-2-amine (100 mg, 365 µmol) in acetic acid (1 ml) and concentrated aqueous HCl (37%; 300 µl, 3.65 mmol) at 00 under an argon atmosphere was added sodium nitrite (50.4 mg, 730 µmol). The mixture was stirred at 00 for 30 mins and copper(I) chloride (72.2 mg, 730 µmol) was added at 0°. The ice bath was removed and the mixture was stirred at r.t for 1 hr. The mixture was poured into $H_2O$/ice and extracted with AcOEt. The organic phase was washed with 10% $NaHCO_3$ solution, dried over $MgSO_4$, filtered and evaporated. The crude product was purified by silica gel chromatography using a $CH_2Cl_2$/MeOH gradient as eluent to obtain the title compound (40 mg, 37%) as off-white solid.
MS: M=294.2 (M+H)+

Step 6: 2-Chloro-3-methyl-6-((1-methyl-3-(pyrrolidin-1-yl)-1H-1,2,4-triazol-5-yl)ethynyl)imidazo[1,2-b]pyridazine The title compound was obtained in analogy to the procedure described step 3 of example 12. Yellow solid.
MS: M=342.4 (M+H)+

Step 7: 2-Chloro-3-methyl-6-(2-(1-methyl-3-(pyrrolidin-1-yl)-1H-1,2,4-triazol-5-yl)ethyl)imidazo[1,2-b]pyridazine The title compound was obtained in analogy to the procedure described in example 6. Light yellow solid.
MS: M=346.4 (M+H)+

Example 65

3-Chloro-2-methyl-6-((1-methyl-3-(pyrrolidin-1-yl)-1H-1,2,4-triazol-5-yl)ethynyl)imidazo[1,2-b]pyridazine

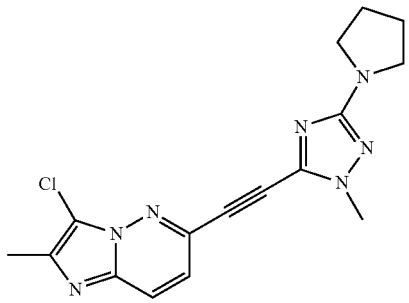 [SMILES: Cc1nc2ccc(C#Cc3nc(N4CCCC4)nn3C)nn2c1Cl]

Step 1: Methyl 6-iodo-2-methylimidazo[1,2-b]pyridazine-3-carboxylate

To a solution of methyl 2-bromo-3-oxobutanoate (5.63 g, 23.1 mmol) in 1,2-dimethoxyethane (100 ml) at r.t. under an argon atmosphere was added 6-iodopyridazin-3-amine (4.25 g, 19.2 mmol). The mixture was refluxed overnight. After cooling to r.t., the solvent was evaporated. The crude product was isolated by chromatography on silica gel using a EtOAc/heptane gradient as eluent, to provide the title compound (1.5 g, 25%) as off-white solid.
MS: M=318.2 (M+H)+

Step 2

The title compound was obtained in analogy to the procedures described in steps 2-6 of example 64.
MS: M=342.4 (M+H)+

Example 66

3-Chloro-2-methyl-6-(2-(1-methyl-3-(pyrrolidin-1-yl)-1H-1,2,4-triazol-5-yl)ethyl)imidazo[1,2-b]pyridazine

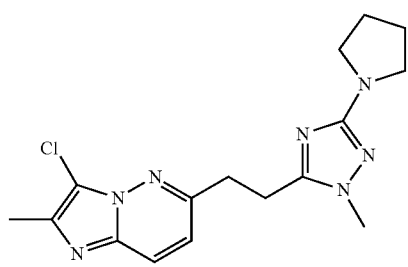 [SMILES: Cc1nc2ccc(CCc3nc(N4CCCC4)nn3C)nn2c1Cl]

The title compound was obtained in analogy to the procedure described in example 6. Yellow solid.
MS: M=346.4 (M+H)⁺

Example 67

2-Methyl-6-((1-methyl-3-(pyrrolidin-1-yl)-1H-1,2,4-triazol-5-yl)ethynyl)imidazo[1,2-b]pyridazine

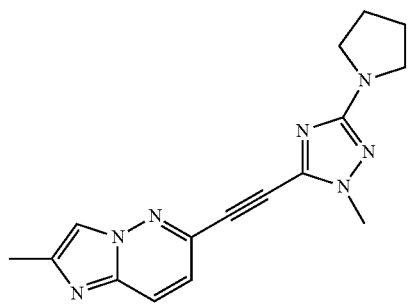 [SMILES: Cc1cn2nc(C#Cc3nc(N4CCCC4)nn3C)ccc2n1]

The title compound was obtained as side product in the last step (Sonogashira reaction) of the preparation of example 65. Off-white solid.
MS: M 308.4 (M+H)⁺

Example 68

2-Methyl-6-(2-(1-methyl-3-(pyrrolidin-1-yl)-1H-1,2,4-triazol-5-yl)ethyl)imidazo[1,2-b]pyridazine

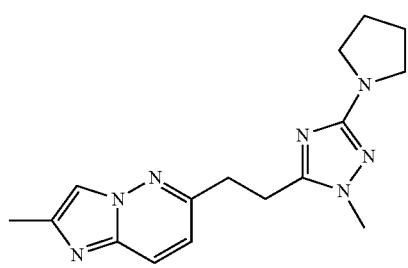 [SMILES: Cc1cn2nc(CCc3nc(N4CCCC4)nn3C)ccc2n1]

The title compound was obtained in analogy to the procedure described in example 6. Off-white solid.
MS: M=312.5 (M+H)⁺

Example 69

N,3-Dimethyl-6-((1-methyl-3-(pyrrolidin-1-yl)-1H-1,2,4-triazol-5-yl)ethynyl)-2-(trifluoromethyl)imidazo[1,2-b]pyridazine-8-carboxamide

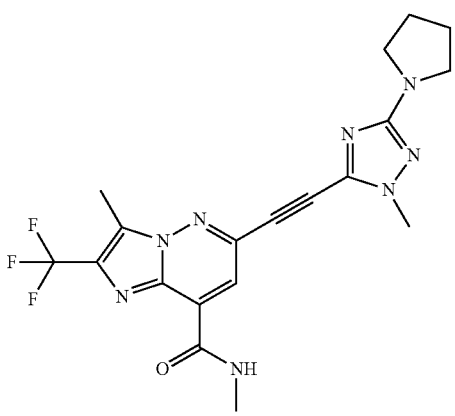 [SMILES: CNC(=O)c1cc(C#Cc2nc(N3CCCC3)nn2C)nn2c(C)c(C(F)(F)F)nc12]

Step 1: 3,6-Dichloropyridazine-4-carbonyl chloride

To a stirred, cooled (0° C.) suspension of 3,6-dichloropyridazine-4-carboxylic acid (3 g, 15.5 mmol) in dichloromethane (35 ml) under an argon atmosphere was added carefully oxalyl chloride (2.17 g, 1.47 ml, 17.1 mmol) followed by DMF (2 drops). Stirring at r.t. was then continued for 18 hrs. The mixture was concentrated to dryness. This crude product was directly used in the next step.

Step 2: 3,6-Dichloro-N-methylpyridazine-4-carboxamide

To a stirred, cooled (0° C.) solution of the crude 3,6-dichloropyridazine-4-carbonyl chloride (3.29 g, 15.6 mmol) in dichloromethane (50 ml) under an argon atmosphere were added methylamine hydrochloride (2.1 g, 31.1 mmol) and triethylamine (3.15 g, 4.31 ml, 31.1 mmol). The mixture was then stirred at r.t. for 18 hrs. The insoluble material (small amount) was filtered off and washed with CH₂Cl₂. The dark brown filtrate was concentrated. The crude product was purified by silica gel chromatography using a CH₂Cl₂/MeOH gradient as eluent to provide the title compound (1.72 g, 54%) as off-white solid.
MS: M 204.1 (M−H)⁻

Step 3: 3-Amino-6-chloro-N-methylpyridazine-4-carboxamide

The title compound was obtained in analogy to the procedure described in step 1 of example 16. Yellow solid.
MS: M 185.1 (M+H)⁺

Step 4: 6-Chloro-2-hydroxy-N,3-dimethyl-2-(trifluoromethyl)-2,3-dihydroimidazo[1,2-b]pyridazine-8-carboxamide A mixture of 3-amino-6-chloro-N-methylpyridazine-4-carboxamide (390 mg, 2.09 mmol), 3-bromo-1,1,1-trifluorobutan-2-one (557 mg, 2.72 mmol) and sodium hydrogen carbonate (228 mg, 2.72 mmol) in ethanol (15 ml) was stirred under an argon atmosphere at 800 for 18 hrs. The mixture was concentrated. The crude product was purified by silica gel chromatography using a CH$_2$Cl$_2$/MeOH gradient as eluent to provide the title compound (388 mg, 60%) as yellow solid.

MS: M 311.3 (M+H)$^+$

Step 4: 6-Chloro-N,3-dimethyl-2-(trifluoromethyl)imidazo[1,2-b]pyridazine-8-carboxamide To a mixture of 6-chloro-2-hydroxy-N,3-dimethyl-2-(trifluoromethyl)-2,3-dihydroimidazo[1,2-b]pyridazine-8-carboxamide (0.385 g, 1.24 mmol) and pyridine (196 mg, 200 µl, 2.48 mmol) was added under an argon atmosphere and at r.t. sulfurous dichloride (295 mg, 180 µl, 2.48 mmol). The mixture was stirred at r.t overnight, then poured into 50 ml ice/water and extracted with CH$_2$Cl$_2$. The combined organics was washed with H$_2$O, dried over MgSO$_4$, filtered and evaporated to obtain the title compound (359 g, 99%) as yellow solid.

MS: M 293.3 (M+H)$^+$

Step 5: N,3-Dimethyl-6-((1-methyl-3-(pyrrolidin-1-yl)-1H-1,2,4-triazol-5-yl)ethynyl)-2-(trifluoromethyl)imidazo[1,2-b]pyridazine-8-carboxamide The title compound was obtained in analogy to the procedures described in step 3 of example 12. Orange solid.

MS: M 433.4 (M+H)$^+$

Example 70

N,3-dimethyl-6-(2-(1-methyl-3-(pyrrolidin-1-yl)-1H-1,2,4-triazol-5-yl)ethyl)-2-(trifluoromethyl)imidazo[1,2-b]pyridazine-8-carboxamide

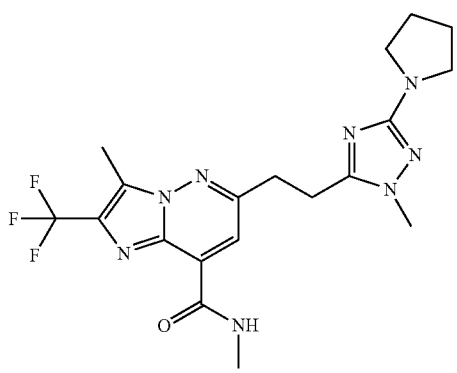 [SMILES: CNC(=O)c1cc(CCc2nc(N3CCCC3)nn2C)nn2c(C)c(C(F)(F)F)nc12]

The title compound was obtained in analogy to the procedure described in example 6. Light yellow solid.

MS: M=437.4 (M+H)$^+$

Example 71

3-Methyl-5-[2-(2-methyl-5-pyrrolidin-1-yl-1,2,4-triazol-3-yl)ethynyl]-2-(trifluoromethyl)pyrazolo[1,5-a]pyrimidine

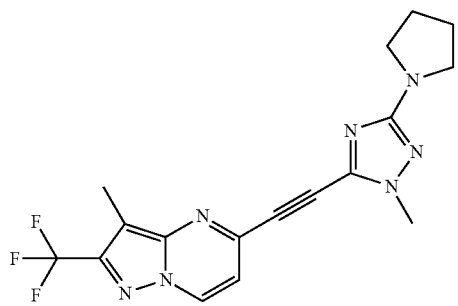 [SMILES: Cc1c(C(F)(F)F)nn2ccc(C#Cc3nc(N4CCCC4)nn3C)nc12]

The title compound was obtained in analogy to the procedures described in example 52 starting from 4-methyl-5-trifluoromethyl-2H-pyrazol-3-ylamine. Yellow solid.

MS: M=376.4 (M+H)$^+$

Example 72

3-methyl-5-(2-(1-methyl-3-(pyrrolidin-1-yl)-1H-1,2,4-triazol-5-yl)ethyl)-2-(trifluoromethyl)pyrazolo[1,5-a]pyrimidine

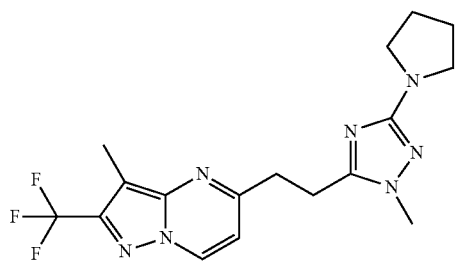 [SMILES: Cc1c(C(F)(F)F)nn2ccc(CCc3nc(N4CCCC4)nn3C)nc12]

The title compound was obtained in analogy to the procedure described in example 6. Light yellow solid.

MS: M=380.4 (M+H)$^+$

The invention claimed is:

1. A compound of formula (I)

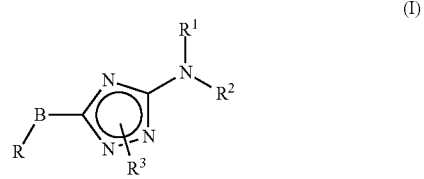

(I)

wherein

B is C$_1$-C$_4$-alkylene, C$_2$-C$_4$-alkenylene, C$_2$-C$_4$-alkynylene, —O—(C$_1$-C$_4$-alkylene)-, —S—(C$_1$-C$_4$-alkylene)-;

R is selected from the group consisting of:

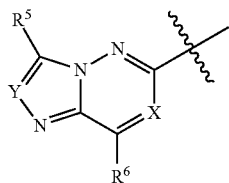

a)

R¹ and R² together with the nitrogen atom to which they are attached, form a bicyclic ring system or heterocycloalkyl which can be substituted by 1 to 3 substituents independently selected from the group consisting of halogen, $C_1$-$C_7$-alkyl, $C_1$-$C_7$-hydroxyalkyl, $C_1$-$C_7$ alkoxy, $C_1$-$C_7$-haloalkyl, hydroxyl and oxo;

R³ is selected from hydrogen, $C_1$-$C_7$-alkyl, $C_1$-$C_7$-alkoxyalkyl, $C_1$-$C_7$-haloalkyl, $(CH_2)_{1,2}$—$C_3$-$C_5$-cycloalkyl, —$(CH_2)_{1,2}$-aryl optionally substituted by $C_1$-$C_7$ alkoxy;

R⁴ and R⁵ are independently selected from hydrogen, halogen, $C_1$-$C_7$-alkyl, $C_1$-$C_7$-haloalkyl, $C_1$-$C_7$-hydroxyalkyl, cyano, or R⁴ and R⁵ together form a $C_3$-$C_8$ cycloalkyl R⁶ is selected from hydrogen, $C_1$-$C_7$-alkyl, $C_1$-$C_7$-haloalkoxy, $C_3$-$C_8$ cycloalkyl, $C_1$-$C_7$ alkoxy, hydroxyl, halogen, $S(O)_2$—$C_1$-$C_7$-alkyl, —C(O)NR'R", NR'R" wherein R' and R" are independently selected from hydrogen, $C_1$-$C_7$-alkyl or R' and R" together with the nitrogen atom to which they are attached form a heterocycloalkyl or R⁶ and R⁷ together form a $C_3$-$C_8$cycloalkyl, X is C—R⁷ wherein R⁷ is selected from hydrogen, $C_1$-$C_7$-alkyl, $C_1$-$C_7$ alkoxy, $C_1$-$C_7$-haloalkyl, $C_3$-$C_8$ cycloalkyl, —C(O)NR'R" wherein R' and R" are independently selected from hydrogen and $C_1$-$C_7$-alkyl, Y is N or C—R⁴.

2. The compound of claim 1 having formula (Ig)

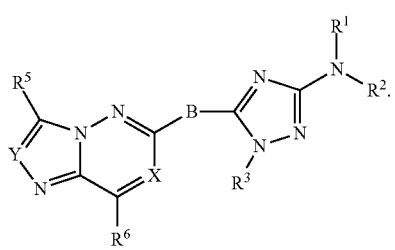

(Ig)

3. The compound of claim 1 having formula (Ih)

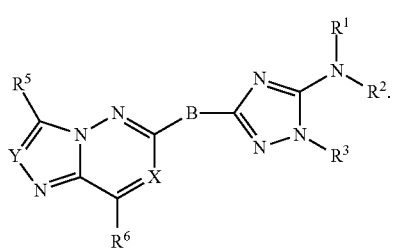

(Ih)

4. The compound of claim 1 wherein B is selected from ethylene, ethenylene, ethynylene, or methoxy.

5. The compound of claim 1 wherein R⁷ is hydrogen, methyl, methoxy, cyclobutyl, cyclohexyl, C(O)NR'R" wherein R' and R" are independently selected from hydrogen and methyl.

6. The compound of claim 1 wherein Y is C—R⁴.

7. The compound of claim 1 wherein R¹ and R² together with the nitrogen atom to which they are attached form pyrrolidinyl.

8. The compound of claim 1, wherein R³ is selected from $C_1$-$C_7$-alkyl.

9. The compound of claim 1 selected from the group consisting of:
3-methyl-6-(2-(1-methyl-3-(pyrrolidin-1-yl)-1H-1,2,4-triazol-5-yl)ethyl)-2-(trifluoromethyl)imidazo[1,2-b]pyridazine;
2,3-dimethyl-6-(2-(1-methyl-3-(pyrrolidin-1-yl)-1H-1,2,4-triazol-5-yl)ethyl)imidazo[1,2-b]pyridazine;
3-Methyl-6-[(E)-2-(2-methyl-5-pyrrolidin-1-yl-2H-[1,2,4]triazol-3-yl)-vinyl]-imidazo[1,2-b]pyridazine-2-carbonitrile;
3-methyl-6-((1-methyl-5-(pyrrolidin-1-yl)-1H-1,2,4-triazol-3-yl)ethynyl)-2-(trifluoromethyl)imidazo[1,2-b]pyridazine;
3-Methyl-6-[2-(2-methyl-5-pyrrolidin-1-yl-2H-[1,2,4]triazol-3-yl)-ethyl]-imidazo[1,2-b]pyridazine-2-carbonitrile;
3-methyl-6-(2-(1-methyl-5-(pyrrolidin-1-yl)-1H-1,2,4-triazol-3-yl)ethyl)-2-(trifluoromethyl)imidazo[1,2-b]pyridazine;
2-(difluoromethyl)-3-methyl-6-((1-methyl-3-(pyrrolidin-1-yl)-1H-1,2,4-triazol-5-yl)ethynyl)imidazo[1,2-b]pyridazine;
2-(difluoromethyl)-3-methyl-6-(2-(1-methyl-3-(pyrrolidin-1-yl)-1H-1,2,4-triazol-5-yl)ethyl)imidazo[1,2-b]pyridazine;
(E)-8-methoxy-3-methyl-6-(2-(1-methyl-3-(pyrrolidin-1-yl)-1H-1,2,4-triazol-5-yl)vinyl)-2-(trifluoromethyl)imidazo[1,2-b]pyridazine;
8-methoxy-3-methyl-6-(2-(1-methyl-3-(pyrrolidin-1-yl)-1H-1,2,4-triazol-5-yl)ethyl)-2-(trifluoromethyl)imidazo[1,2-b]pyridazine;
8-methoxy-2,3-dimethyl-6-(2-(1-methyl-3-(pyrrolidin-1-yl)-1H-1,2,4-triazol-5-yl)ethyl)imidazo[1,2-b]pyridazine;
5-[2-(2-Methyl-5-pyrrolidin-1-yl-2H-[1,2,4]triazol-3-yl)-ethyl]-2,3-dihydro-1H-3b,4,8-triaza-cyclopenta[a]indene;
2,3,8-trimethyl-6-(2-(1-methyl-3-(pyrrolidin-1-yl)-1H-1,2,4-triazol-5-yl)ethyl)imidazo[1,2-b]pyridazine;
2,3,7-trimethyl-6-((1-methyl-3-(pyrrolidin-1-yl)-1H-1,2,4-triazol-5-yl)ethynyl)imidazo[1,2-b]pyridazine;
2,3,7-trimethyl-6-(2-(1-methyl-3-(pyrrolidin-1-yl)-1H-1,2,4-triazol-5-yl)ethyl)imidazo[1,2-b]pyridazine;
2,3-dimethyl-6-(2-(1-methyl-3-(pyrrolidin-1-yl)-1H-1,2,4-triazol-5-yl)ethyl)-8-(pyrrolidin-1-yl)imidazo[1,2-b]pyridazine;
-(2-methyl-6-(2-(1-methyl-3-(pyrrolidin-1-yl)-1H-1,2,4-triazol-5-yl)ethyl)imidazo[1,2-b]pyridazin-3-yl)methanol;
3-methyl-6-((1-methyl-3-(pyrrolidin-1-yl)-1H-1,2,4-triazol-5-yl)methoxy)-2-(trifluoromethyl)imidazo[1,2-b]pyridazine;
2,3-dimethyl-6-(2-(1-methyl-3-(pyrrolidin-1-yl)-1H-1,2,4-triazol-5-yl)ethyl)-7,8,9,10-tetrahydroimidazo[2,1-a]phthalazine;
8-isopropoxy-2,3-di methyl-6-((1-methyl-3-(pyrrolidin-1-yl)-1H-1,2,4-triazol-5-yl)ethynyl)imidazo[1,2-b]pyridazine;
(E)-8-isopropoxy-2,3-dimethyl-6-(2-(1-methyl-3-(pyrrolidin-1-yl)-1H-1,2,4-triazol-5-yl)vinyl)imidazo[1,2-b]pyridazine;
8-isopropoxy-2,3-dimethyl-6-(2-(1-methyl-3-(pyrrolidin-1-yl)-1H-1,2,4-triazol-5-yl)ethyl)imidazo[1,2-b]pyridazine;

2,3-dimethyl-6-((1-methyl-3-(pyrrolidin-1-yl)-1H-1,2,4-triazol-5-yl)methylthio)imidazo[1,2-b]pyridazine;
2,3-dimethyl-6-((1-methyl-3-(pyrrolidin-1-yl)-1H-1,2,4-triazol-5-yl)ethynyl)-8-(methylsulfonyl)imidazo[1,2-b]pyridazine;
2,3-dimethyl-6-((1-methyl-3-(pyrrolidin-1-yl)-1H-1,2,4-triazol-5-yl)methoxy)imidazo[1,2-b]pyridazine;
2,3-dimethyl-6-(2-(1-methyl-3-(pyrrolidin-1-yl)-1H-1,2,4-triazol-5-yl)ethyl)-8-(methylsulfonyl)imidazo[1,2-b]pyridazine;
2-chloro-6-((1-methyl-3-(pyrrolidin-1-yl)-1H-1,2,4-triazol-5-yl)ethynyl)imidazo[1,2-b]pyridazine;
2-chloro-6-(2-(1-methyl-3-(pyrrolidin-1-yl)-1H-1,2,4-triazol-5-yl)ethyl)imidazo[1,2-b]pyridazine;
2-chloro-3-methyl-6-((1-methyl-3-(pyrrolidin-1-yl)-1H-1,2,4-triazol-5-yl)ethynyl)imidazo[1,2-b]pyridazine;
N,2,3-trimethyl-6-((1-methyl-3-(pyrrolidin-1-yl)-1H-1,2,4-triazol-5-yl)ethynyl)imidazo[1,2-b]pyridazine-7-carboxamide;
N,2,3-trimethyl-6-((1-methyl-3-(pyrrolidin-1-yl)-1H-1,2,4-triazol-5-yl)ethynyl)imidazo[1,2-b]pyridazine-8-carboxamide;
N,2,3-trimethyl-6-(2-(1-methyl-3-(pyrrolidin-1-yl)-1H-1,2,4-triazol-5-yl)ethyl)imidazo[1,2-b]pyridazine-8-carboxamide;
2,3-dimethyl-6-((1-methyl-3-(pyrrolidin-1-yl)-1H-1,2,4-triazol-5-yl)ethynyl)-8-(trifluoromethyl)imidazo[1,2-b]pyridazine;
2,3-dimethyl-6-(2-(1-methyl-3-(pyrrolidin-1-yl)-1H-1,2,4-triazol-5-yl)ethyl)-8-(trifluoromethyl)imidazo[1,2-b]pyridazine;
8-isopropyl-2,3-di methyl-6-((1-methyl-3-(pyrrolidin-1-yl)-1H-1,2,4-triazol-5-yl)ethynyl)imidazo[1,2-b]pyridazine;
8-isopropyl-2,3-dimethyl-6-(2-(1-methyl-3-(pyrrolidin-1-yl)-1H-1,2,4-triazol-5-yl)ethyl)imidazo[1,2-b]pyridazine;
8-cyclopropyl-2,3-dimethyl-6-((1-methyl-3-(pyrrolidin-1-yl)-1H-1,2,4-triazol-5-yl)ethynyl)imidazo[1,2-b]pyridazine;
8-cyclobutyl-2,3-dimethyl-6-((1-methyl-3-(pyrrolidin-1-yl)-1H-1,2,4-triazol-5-yl)ethynyl)imidazo[1,2-b]pyridazine;
8-cyclobutyl-2,3-dimethyl-6-(2-(1-methyl-3-(pyrrolidin-1-yl)-1H-1,2,4-triazol-5-yl)ethyl)imidazo[1,2-b]pyridazine;
8-cyclopropyl-2,3-dimethyl-6-(2-(1-methyl-3-(pyrrolidin-1-yl)-1H-1,2,4-triazol-5-yl)ethyl)imidazo[1,2-b]pyridazine;
7-isopropyl-2,3-di methyl-6-((1-methyl-3-(pyrrolidin-1-yl)-1H-1,2,4-triazol-5-yl)ethynyl)imidazo[1,2-b]pyridazine;
7-cyclobutyl-2,3-dimethyl-6-((1-methyl-3-(pyrrolidin-1-yl)-1H-1,2,4-triazol-5-yl)ethynyl)imidazo[1,2-b]pyridazine;
3,8-dimethyl-6-((1-methyl-3-(pyrrolidin-1-yl)-1H-1,2,4-triazol-5-yl)ethynyl)-2-(trifluoromethyl)imidazo[1,2-b]pyridazine;
3,8-dimethyl-6-(2-(1-methyl-3-(pyrrolidin-1-yl)-1H-1,2,4-triazol-5-yl)ethyl)-2-(trifluoromethyl)imidazo[1,2-b]pyridazine;
3-methyl-6-((1-methyl-3-(pyrrolidin-1-yl)-1H-1,2,4-triazol-5-yl)ethynyl)-[1,2,4]triazolo[4,3-b]pyridazine;
3-methyl-6-(2-(1-methyl-3-(pyrrolidin-1-yl)-1H-1,2,4-triazol-5-yl)ethyl)-[1,2,4]triazolo[4,3-b]pyridazine;
7-cyclohexyl-2,3-dimethyl-6-(2-(1-methyl-3-(pyrrolidin-1-yl)-1H-1,2,4-triazol-5-yl)ethyl)imidazo[1,2-b]pyridazine;
7-methoxy-2,3-dimethyl-6-((1-methyl-3-(pyrrolidin-1-yl)-1H-1,2,4-triazol-5-yl)ethynyl)imidazo[1,2-b]pyridazine;
3-methyl-6-((1-methyl-3-(pyrrolidin-1-yl)-1H-1,2,4-triazol-5-yl)ethynyl)-8-(2,2,2-trifluoroethoxy)-2-(trifluoromethyl)imidazo[1,2-b]pyridazine;
3-methyl-6-(2-(1-methyl-3-(pyrrolidin-1-yl)-1H-1,2,4-triazol-5-yl)ethyl)-8-(2,2,2-trifluoroethoxy)-2-(trifluoromethyl)imidazo[1,2-b]pyridazine;
2-chloro-3-methyl-6-(2-(1-methyl-3-(pyrrolidin-1-yl)-1H-1,2,4-triazol-5-yl)ethyl)imidazo[1,2-b]pyridazine;
3-chloro-2-methyl-6-((1-methyl-3-(pyrrolidin-1-yl)-1H-1,2,4-triazol-5-yl)ethynyl)imidazo[1,2-b]pyridazine;
3-chloro-2-methyl-6-(2-(1-methyl-3-(pyrrolidin-1-yl)-1H-1,2,4-triazol-5-yl)ethyl)imidazo[1,2-b]pyridazine;
2-methyl-6-((1-methyl-3-(pyrrolidin-1-yl)-1H-1,2,4-triazol-5-yl)ethynyl)imidazo[1,2-b]pyridazine;
2-methyl-6-(2-(1-methyl-3-(pyrrolidin-1-yl)-1H-1,2,4-triazol-5-yl)ethyl)imidazo[1,2-b]pyridazine;
N,3-dimethyl-6-((1-methyl-3-(pyrrolidin-1-yl)-1H-1,2,4-triazol-5-yl)ethynyl)-2-(trifluoromethyl)imidazo[1,2-b]pyridazine-8-carboxamide; and
N,3-dimethyl-6-(2-(1-methyl-3-(pyrrolidin-1-yl)-1H-1,2,4-triazol-5-yl)ethyl)-2-(trifluoromethyl)imidazo[1,2-b]pyridazine-8-carboxamide.

10. A method for the treatment of schizophrenia and positive, negative and/or cognitive symptoms associated with schizophrenia in a patient in need thereof which method comprises administering therapeutically effective amount of a compound of claim 1.

11. A process for the manufacture of a compound of formula (I) wherein B is $C_2$-alkylene or $C_2$ alkenylene, Y is C—$R^4$ and X is C—$R^7$ comprising:

a) reacting a compound of formula (III)

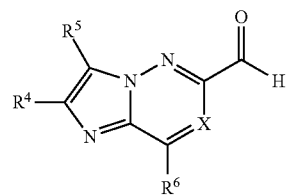

(III)

with b) a compound of formula (Ja)

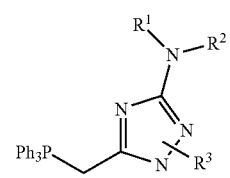

(Ja)

or c) reacting a compound of formula (F)

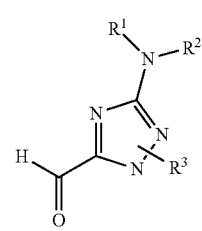

(F)

with
d) a compound of formula (VI)

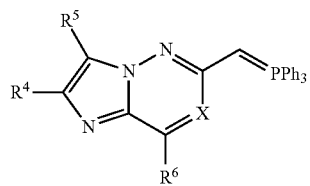
(VI)

to a compound of formula (Ij)

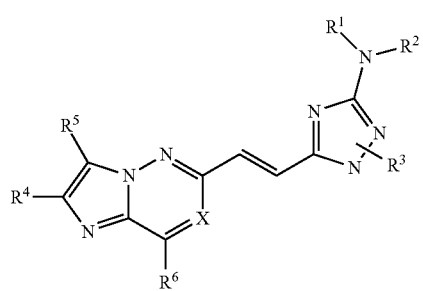
(Ij)

and optionally hydrogenating a compound of formula Ij to afford a compound of formula Ik

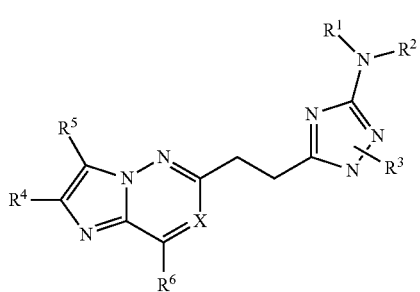
(Ik)

wherein $R^1$, $R^2$, $R^3$, $R^4$, $R^5$ and $R^6$ are as defined in claim 1.

12. A process for the manufacture of a compound of formula (I) wherein B is $C_2$-alkylene or $C_2$-alkynylene, Y is C—$R^4$ and X is C—$R^7$ comprising:
a) reacting a compound of formula (D)

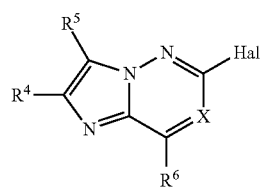
(D)

with
b) a compound of formula (O) or (V)

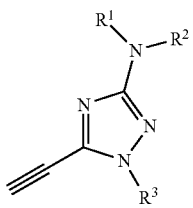
(O)

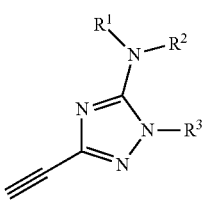
(V)

to afford a compound of formula (Im)

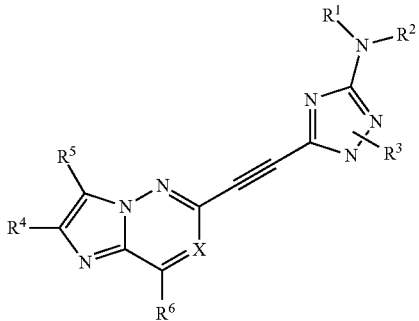

and optionally hydrogenating a compound of formula (Im) to afford a compound of formula (Ik)

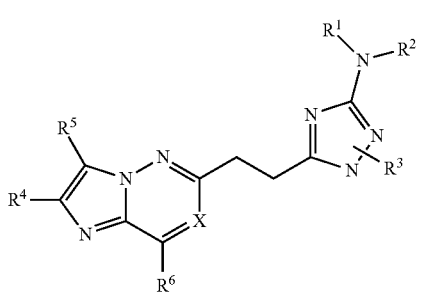
(Ik)

wherein $R^1$, $R^2$, $R^3$, $R^4$, $R^5$ and $R^6$ are as defined in claim 1.

13. A pharmaceutical composition comprising a compound of claim 1 and a therapeutically inert carrier.

14. The compound of claim 8, wherein $R^3$ is methyl.

* * * * *